(12) United States Patent
Yang et al.

(10) Patent No.: US 10,835,711 B2
(45) Date of Patent: Nov. 17, 2020

(54) TELESCOPING NEUROVASCULAR CATHETER WITH ENLARGEABLE DISTAL OPENING

(71) Applicant: INCEPT, LLC, Sunnyvale, CA (US)

(72) Inventors: Yi Yang, San Francisco, CA (US); Farhad Khosravi, Los Altos Hills, CA (US); Joseph Rimsa, Palo Alto, CA (US)

(73) Assignee: Incept, LLC, Sunnyvale, CA (US)

( * ) Notice: Subject to any disclaimer, the term of this patent is extended or adjusted under 35 U.S.C. 154(b) by 0 days.

(21) Appl. No.: 15/443,874

(22) Filed: Feb. 27, 2017

(65) Prior Publication Data
US 2017/0238953 A1    Aug. 24, 2017

Related U.S. Application Data

(63) Continuation of application No. 15/442,393, filed on Feb. 24, 2017, now Pat. No. 10,183,145.
(Continued)

(51) Int. Cl.
*A61M 25/00* (2006.01)
*A61B 17/22* (2006.01)
(Continued)

(52) U.S. Cl.
CPC ......... *A61M 25/0053* (2013.01); *A61B 6/481* (2013.01); *A61B 6/501* (2013.01);
(Continued)

(58) Field of Classification Search
CPC ............... A61B 17/22; A61B 17/3207; A61B 17/320708; A61B 17/320725;
(Continued)

(56) References Cited

U.S. PATENT DOCUMENTS

| 4,319,580 A | 3/1982 | Colley et al. |
| 4,611,594 A | 9/1986 | Grayhack et al. |

(Continued)

FOREIGN PATENT DOCUMENTS

| EP | 0 309 471 | 8/1996 |
| EP | 1 349 486 | 3/2008 |

(Continued)

OTHER PUBLICATIONS

International Search Report and Written Opinion in PCT/US2017/019453, dated Jun. 9, 2017.

(Continued)

*Primary Examiner* — Katherine H Schwiker
(74) *Attorney, Agent, or Firm* — Knobbe, Martens, Olson & Bear, LLP

(57) ABSTRACT

A telescoping catheter is provided such as for distal neurovascular aspiration or access. The catheter includes an elongate, flexible tubular body, having a proximal section with at least one lumen and a distal section which is axially movably positioned within the lumen. A control is provided for advancing the distal section from a first, proximally retracted position within the proximal section to a second extended position, extending distally beyond the proximal section. The distal end of at least one of the proximal and distal sections may be provided with at least one active feature, such as at least one movable jaw or rotatable agitator, to assist in the capture of vascular obstruction. The jaw may be operable in response to application of pulsatile negative pressure through the catheter.

15 Claims, 41 Drawing Sheets

Related U.S. Application Data

(60) Provisional application No. 62/443,595, filed on Jan. 6, 2017, provisional application No. 62/299,418, filed on Feb. 24, 2016.

(51) Int. Cl.

| | | |
|---|---|---|
| *A61B 17/3203* | (2006.01) | |
| *A61B 17/12* | (2006.01) | |
| *A61F 2/95* | (2013.01) | |
| *A61M 25/09* | (2006.01) | |
| *A61F 7/12* | (2006.01) | |
| *A61M 25/01* | (2006.01) | |
| *A61M 39/06* | (2006.01) | |
| *A61M 1/00* | (2006.01) | |
| *A61B 17/3207* | (2006.01) | |
| *A61B 6/00* | (2006.01) | |
| *A61M 1/32* | (2006.01) | |
| *A61M 25/06* | (2006.01) | |
| *A61M 25/10* | (2013.01) | |
| *B29C 41/14* | (2006.01) | |
| *A61L 29/02* | (2006.01) | |
| *A61L 29/04* | (2006.01) | |
| *A61L 29/06* | (2006.01) | |
| *A61L 29/14* | (2006.01) | |
| *A61M 5/00* | (2006.01) | |
| *A61B 17/00* | (2006.01) | |
| *B29C 41/42* | (2006.01) | |
| *B29C 41/02* | (2006.01) | |
| *B29C 41/22* | (2006.01) | |
| *B29C 65/00* | (2006.01) | |
| *B29C 63/20* | (2006.01) | |
| *B29C 63/18* | (2006.01) | |
| *B29C 63/22* | (2006.01) | |
| *A61M 31/00* | (2006.01) | |
| *B29K 27/18* | (2006.01) | |
| *B29K 75/00* | (2006.01) | |
| *B29L 31/00* | (2006.01) | |

(52) U.S. Cl.
CPC .. *A61B 17/12022* (2013.01); *A61B 17/12168* (2013.01); *A61B 17/12186* (2013.01); *A61B 17/22* (2013.01); *A61B 17/2202* (2013.01); *A61B 17/22031* (2013.01); *A61B 17/3203* (2013.01); *A61B 17/32037* (2013.01); *A61B 17/320758* (2013.01); *A61F 2/95* (2013.01); *A61F 7/12* (2013.01); *A61L 29/02* (2013.01); *A61L 29/041* (2013.01); *A61L 29/06* (2013.01); *A61L 29/14* (2013.01); *A61M 1/0035* (2014.02); *A61M 1/0066* (2013.01); *A61M 1/32* (2013.01); *A61M 5/007* (2013.01); *A61M 25/005* (2013.01); *A61M 25/007* (2013.01); *A61M 25/008* (2013.01); *A61M 25/0009* (2013.01); *A61M 25/0012* (2013.01); *A61M 25/0023* (2013.01); *A61M 25/0045* (2013.01); *A61M 25/0074* (2013.01); *A61M 25/0082* (2013.01); *A61M 25/0097* (2013.01); *A61M 25/01* (2013.01); *A61M 25/0102* (2013.01); *A61M 25/0108* (2013.01); *A61M 25/0147* (2013.01); *A61M 25/0662* (2013.01); *A61M 25/09* (2013.01); *A61M 25/10* (2013.01); *A61M 25/1027* (2013.01); *A61M 39/06* (2013.01); *B29C 41/14* (2013.01); *A61B 17/22012* (2013.01); *A61B 2017/00398* (2013.01); *A61B 2017/00526* (2013.01); *A61B 2017/00734* (2013.01); *A61B 2017/00862* (2013.01); *A61B 2017/00867* (2013.01); *A61B 2017/00898* (2013.01); *A61B 2017/00955* (2013.01); *A61B 2017/22025* (2013.01); *A61B 2017/22034* (2013.01); *A61B 2017/22038* (2013.01); *A61B 2017/22062* (2013.01); *A61B 2017/22067* (2013.01); *A61B 2017/22079* (2013.01); *A61B 2017/22084* (2013.01); *A61B 2017/320733* (2013.01); *A61B 2017/320775* (2013.01); *A61B 2217/005* (2013.01); *A61F 2007/126* (2013.01); *A61L 2400/10* (2013.01); *A61L 2400/16* (2013.01); *A61M 1/008* (2013.01); *A61M 25/0052* (2013.01); *A61M 31/005* (2013.01); *A61M 2025/0002* (2013.01); *A61M 2025/0004* (2013.01); *A61M 2025/0046* (2013.01); *A61M 2025/0058* (2013.01); *A61M 2025/0059* (2013.01); *A61M 2025/0079* (2013.01); *A61M 2025/0096* (2013.01); *A61M 2025/0175* (2013.01); *A61M 2039/062* (2013.01); *A61M 2205/0216* (2013.01); *A61M 2205/0266* (2013.01); *A61M 2205/3344* (2013.01); *A61M 2210/12* (2013.01); *B29C 41/02* (2013.01); *B29C 41/22* (2013.01); *B29C 41/42* (2013.01); *B29C 63/18* (2013.01); *B29C 63/20* (2013.01); *B29C 63/22* (2013.01); *B29C 66/52* (2013.01); *B29C 66/522* (2013.01); *B29C 66/5221* (2013.01); *B29K 2027/18* (2013.01); *B29K 2075/00* (2013.01); *B29L 2031/7542* (2013.01)

(58) Field of Classification Search
CPC ............ A61B 17/221; A61B 17/32075; A61B 17/320758; A61B 17/22031; A61B 17/22032; A61B 17/3203; A61B 17/32037; A61B 2017/32032; A61B 17/32035; A61B 17/22041; A61B 17/22067; A61B 2017/320716; A61B 2017/320733; A61B 2017/2212; A61B 2017/2215; A61B 2017/2217; A61B 2017/32041; A61B 2017/22034; A61B 2017/22035; A61B 2017/32035; A61B 2017/22079; A61B 2017/22084; A61B 2017/22038; A61B 2017/22039; A61B 17/22012; A61B 2017/22067; A61M 1/008; A61M 1/0082; A61M 1/0084; A61M 2025/0175; A61M 2025/004; A61M 2025/006; A61M 2039/062
See application file for complete search history.

(56) References Cited

U.S. PATENT DOCUMENTS

| | | |
|---|---|---|
| 4,762,129 A | 8/1988 | Bonzel |
| 4,810,582 A | 3/1989 | Gould et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,234,416 A | 8/1993 | Macaulay et al. |
| 5,243,997 A | 9/1993 | Uflacker |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A * | 5/1995 | Wilk ............... A61B 18/10 |
| | | 606/113 |
| 5,423,846 A | 6/1995 | Fischell |
| 5,439,445 A | 8/1995 | Kontos |

(56) References Cited

U.S. PATENT DOCUMENTS

| | | |
|---|---|---|
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,766,191 A | 6/1998 | Trerotola |
| 5,776,141 A | 7/1998 | Klein et al. |
| 5,827,242 A | 10/1998 | Follmer |
| 5,843,103 A | 12/1998 | Wulfrnan |
| 5,885,209 A | 3/1999 | Green |
| 5,891,114 A | 4/1999 | Chien et al. |
| 5,895,398 A | 4/1999 | Wensel |
| 5,899,892 A | 5/1999 | Mortier et al. |
| 5,916,192 A | 6/1999 | Nita et al. |
| 6,007,530 A | 12/1999 | Dornhofer et al. |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,285,903 B1 | 9/2001 | Rosenthal |
| 6,355,027 B1 | 3/2002 | Le et al. |
| 6,394,976 B1 | 5/2002 | Winston et al. |
| 6,451,005 B1 | 9/2002 | Saitou et al. |
| 6,468,219 B1 | 10/2002 | Njemanze |
| 6,482,217 B1 | 11/2002 | Pintor et al. |
| 6,511,492 B1 | 1/2003 | Rosenbluth |
| 6,524,303 B1 | 2/2003 | Garibaldi et al. |
| 6,533,751 B2 | 3/2003 | Cragg |
| 6,554,820 B1 | 4/2003 | Wendlandt |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,824,550 B1 | 11/2004 | Pintor et al. |
| 6,977,068 B1 | 12/2005 | Nair et al. |
| 7,037,267 B1 | 5/2006 | Lipson et al. |
| 7,104,979 B2 | 9/2006 | Jansen et al. |
| 7,232,452 B2 | 6/2007 | Adams et al. |
| 7,309,334 B2 | 12/2007 | von Hoffm |
| 7,507,229 B2 | 3/2009 | Hewitt et al. |
| 7,537,568 B2 | 5/2009 | Moehring et al. |
| 7,558,622 B2 | 7/2009 | Tran |
| 7,771,358 B2 | 8/2010 | Moehring |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin |
| 7,905,891 B2 | 3/2011 | Self |
| 7,931,659 B2 | 4/2011 | Bose et al. |
| 7,938,820 B2 | 5/2011 | Webster et al. |
| 7,988,646 B2 | 8/2011 | Taber |
| 8,021,351 B2 | 9/2011 | Boldenow et al. |
| 8,048,032 B2 | 11/2011 | Root et al. |
| 8,062,316 B2 | 11/2011 | Patel |
| 8,070,694 B2 | 12/2011 | Galdonik et al. |
| 8,084,246 B2 | 12/2011 | Hoon et al. |
| 8,142,413 B2 | 3/2012 | Root et al. |
| 8,114,032 B2 | 4/2012 | Ferry et al. |
| 8,211,023 B2 | 7/2012 | Swan et al. |
| 8,235,968 B2 | 8/2012 | Tremaglio |
| 8,292,850 B2 | 10/2012 | Root et al. |
| 8,366,735 B2 | 2/2013 | Bose et al. |
| 8,460,312 B2 | 6/2013 | Bose et al. |
| 8,517,955 B2 | 8/2013 | Keast |
| 8,609,426 B2 | 12/2013 | Silver |
| 8,663,259 B2 | 3/2014 | Levine et al. |
| 8,682,411 B2 | 3/2014 | Kassab et al. |
| 8,696,698 B2 | 4/2014 | Chomas |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse |
| 8,932,320 B1 | 1/2015 | Janardhan et al. |
| RE45,380 E | 2/2015 | Root et al. |
| 8,974,411 B2 | 3/2015 | McKinnon |
| 8,992,506 B2 | 3/2015 | Gulachenski |
| 9,014,786 B2 | 4/2015 | Carmeli et al. |
| 9,023,070 B2 | 5/2015 | Levine et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,439,791 B2 | 9/2016 | Vong et al. |
| 9,451,884 B2 | 9/2016 | Palovich |
| 9,451,963 B2 | 9/2016 | Cruise et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |

(56) References Cited

U.S. PATENT DOCUMENTS

| | | |
|---|---|---|
| 9,717,500 B2 | 8/2017 | Tieu et al. |
| 9,724,103 B2 | 8/2017 | Cruise et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 2001/0031981 A1 | 10/2001 | Evans |
| 2002/0016565 A1 | 2/2002 | Zadno-Azizi et al. |
| 2002/0026145 A1 | 2/2002 | Bagaoisan et al. |
| 2002/0091372 A1 | 7/2002 | Cragg |
| 2002/0156460 A1 | 10/2002 | Ye |
| 2002/0169467 A1 | 11/2002 | Heitzmann |
| 2002/0177899 A1 | 11/2002 | Eum et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0195546 A1 | 10/2003 | Solar et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1 | 10/2004 | Kellett |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0059957 A1 | 3/2005 | Campbell |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0262350 A1 | 10/2008 | Unger |
| 2008/0312639 A1 | 12/2008 | Weber |
| 2009/0030400 A1 | 1/2009 | Bose et al. |
| 2009/0043330 A1 | 2/2009 | To |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel |
| 2009/0312699 A1 | 12/2009 | Pudelko |
| 2010/0049168 A1 | 2/2010 | Parker et al. |
| 2010/0057051 A1 | 3/2010 | Howat et al. |
| 2010/0114017 A1* | 5/2010 | Lenker ............. A61B 17/12118 |
| | | 604/96.01 |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1* | 6/2011 | Chomas ................. A61F 2/013 |
| | | 623/1.12 |
| 2011/0152998 A1 | 6/2011 | Berez et al. |
| 2011/0172700 A1 | 7/2011 | Bose et al. |
| 2011/0230859 A1 | 9/2011 | Galdonik et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131710 A1 | 5/2013 | Carmeli |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0155932 A1 | 6/2014 | Bose et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0273920 A1 | 9/2014 | Smith |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0343537 A1 | 11/2014 | Eversull et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0173782 A1 | 6/2015 | Garrison |
| 2015/0335857 A1 | 11/2015 | Ishikawa |
| 2015/0359547 A1* | 12/2015 | Vale ....................... A61B 17/22 |
| | | 606/115 |
| 2016/0008572 A1 | 1/2016 | Di Caprio |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1* | 5/2016 | Holochwost ........... A61B 17/22 |
| | | 606/159 |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206322 A1 | 7/2016 | Fitz et al. |
| 2016/0220741 A1* | 8/2016 | Garrison ............... A61M 1/008 |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |

(56) References Cited

U.S. PATENT DOCUMENTS

| | | |
|---|---|---|
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0238950 A1 | 8/2017 | Yang et al. |
| 2017/0238951 A1 | 8/2017 | Yang et al. |
| 2017/0239440 A1 | 8/2017 | Yang et al. |
| 2017/0239441 A1 | 8/2017 | Yang et al. |
| 2017/0239447 A1 | 8/2017 | Yang et al. |
| 2017/0246014 A1 | 8/2017 | Rapaport et al. |
| 2017/0252536 A1 | 9/2017 | Yang et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Panian |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Bagaoisan et al. |
| 2018/0193026 A1 | 7/2018 | Yang |
| 2018/0207399 A1 | 7/2018 | Chou et al. |
| 2018/0228502 A1 | 8/2018 | Shaffer |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2019/0336149 A1 | 11/2019 | Yang |
| 2019/0336727 A1 | 11/2019 | Yang |
| 2019/0366041 A1 | 12/2019 | Yang |
| 2020/0001046 A1 | 1/2020 | Yang |
| 2020/0008820 A1 | 1/2020 | Aboytes et al. |
| 2020/0009301 A1 | 1/2020 | Yee |

FOREIGN PATENT DOCUMENTS

| | | |
|---|---|---|
| EP | 2 069 528 | 3/2013 |
| JP | 2006-102222 | 4/2006 |
| WO | WO 1995/009659 | 4/1995 |
| WO | WO 2000/000100 | 1/2000 |
| WO | WO 09/132218 | 10/2009 |

OTHER PUBLICATIONS

Simon et al., *Hydrodynamic comparison of the Penumbra system and commonly available syringes in forced-suction thrombectomy*, J. Neuro Intervent Surg 2014, 6, pp. 205-211.

Simon et al., *Exploring the efficacy of cyclic vs. static aspiration in a cerebral thrombectomy model: an initial proof of concept study*, J. Neuro Intervent Surg 2014, 6 pp. 677-683.

Spiotta et al., Evolution of thrombectomy approaches and devices for acute stroke: a technical review, J. Neuro Intervent Surg 2015, 7, pp. 2-7.

Merit Medical Systems Acquired Distal Access's SPINR Platform, Jul. 15, 2015, Digital Access, LLC; Merit Medical Systems, 5 pages.

Guidezilla Guide Extension Catheter, Boston Scientific 510k Submission, Feb. 20, 2017, 5 pages.

U.S. Appl. No. 15/862,488, Thromboresistant Coatings for Aneurysm Treatment Devices, filed Jan. 4, 2018.

U.S. Appl. No. 15/442,393 (U.S. Pat. No. 10,183,145), Enhanced Flexibility Neurovascular Catheter, filed Feb. 24, 2017 (Jan. 22, 2019).

U.S. Appl. No. 15/443,841, Method of Pulsatile Neurovascular Aspiration With Telescoping Catheter, filed Feb. 27, 2017.

U.S. Appl. No. 15/443,838 (U.S. Pat. No. 10,179,224), Enhanced Flexibility Neurovascular Catheter With Tensile Support, filed Feb. 27, 2017 (Jan. 15, 2019).

U.S. Appl. No. 15/443,877 (U.S. Pat. No. 10,183,146), Method of Making an Enhanced Flexibility Neurovascular Catheter, filed Feb. 27, 2017 (Jan. 22, 2019).

U.S. Appl. No. 15/443,948, (U.S. Pat. No. 10,441,745) Neurovascular Catheter With Enlargeable Distal End, filed Feb. 27, 2017 (Oct. 15, 2019).

U.S. Appl. No. 16/542,657, Method of Making an Enhanced Flexibility Neurovascular Catheter, filed Aug. 16, 2019.

U.S. Appl. No. 15/444,038 (U.S. Pat. No. 10,183,147) Neurovascular Catheter Extension Segment, filed Feb. 27, 2017 (Jan. 22, 2019).

U.S. Appl. No. 16/503,899, Sealed Neurovascular Extendable Catheter, dated Jul. 5, 2019.

U.S. Appl. No. 16/503,886, Vacuum Transfer Tool for Extendable Catheter, filed Jul. 5, 2019.

U.S. Appl. No. 16/398,626, Devices and Methods for Removing Obstructive Material From an Intravascular Site, filed Apr. 30, 2019.

U.S. Appl. No. 16/400,263, Neurovascular Catheter Having Atraumatic Angled Tip, filed May 1, 2019.

U.S. Appl. No. 16/570,084, Enhanced Flexibility Neurovascular Catheter With Tensile Support, dated Sep. 13, 2019.

U.S. Appl. No. 16/683,718, Devices and Methods for Removing Obstructive Material from an Intravascular Site, filed Nov. 14, 2019.

U.S. Appl. No. 16/704,330, Neurovascular Aspiration Catheter with Elliptical Aspiration Port, filed Dec. 5, 2019.

U.S. Appl. No. 16/589,563, Devices and Methods for Removing Obstructive Material from an Intravascular Site, filed Oct. 1, 2019.

U.S. Appl. No. 16/728,469, Neurovascular Access with Dynamic Assistance, filed Dec. 27, 2019.

* cited by examiner

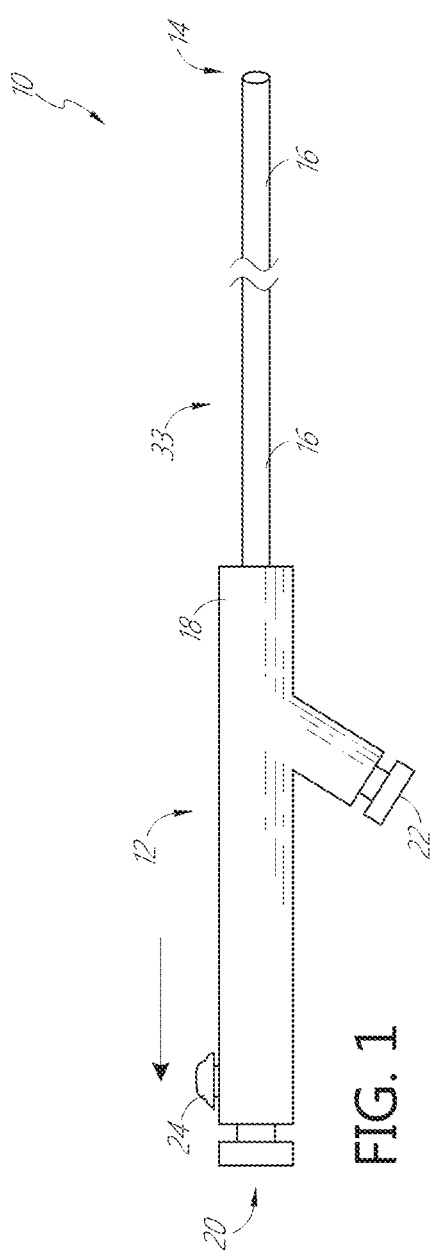
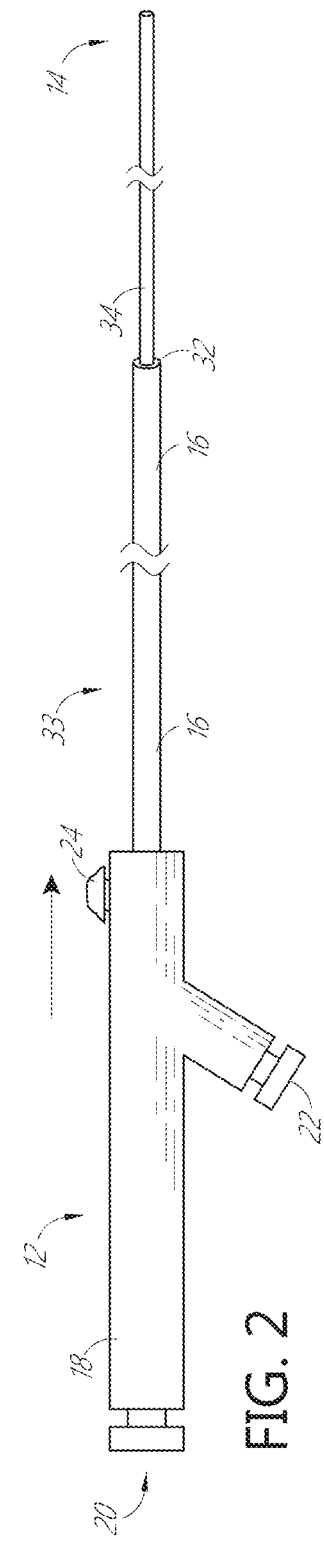
FIG. 1
FIG. 2

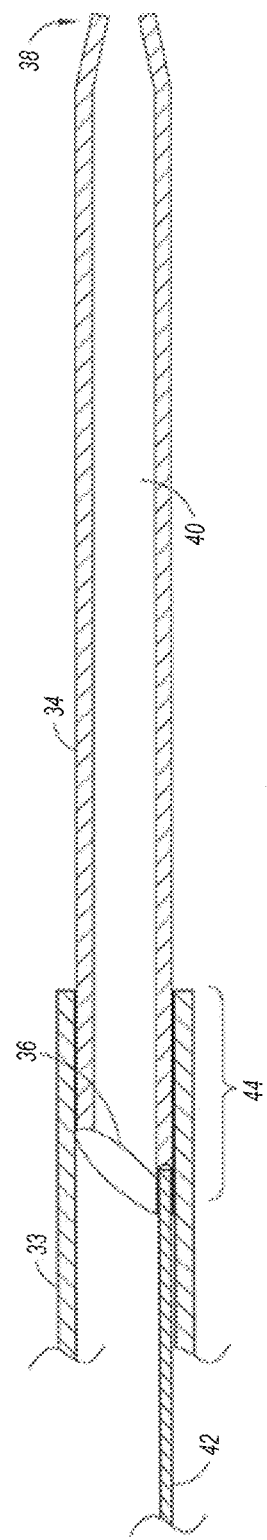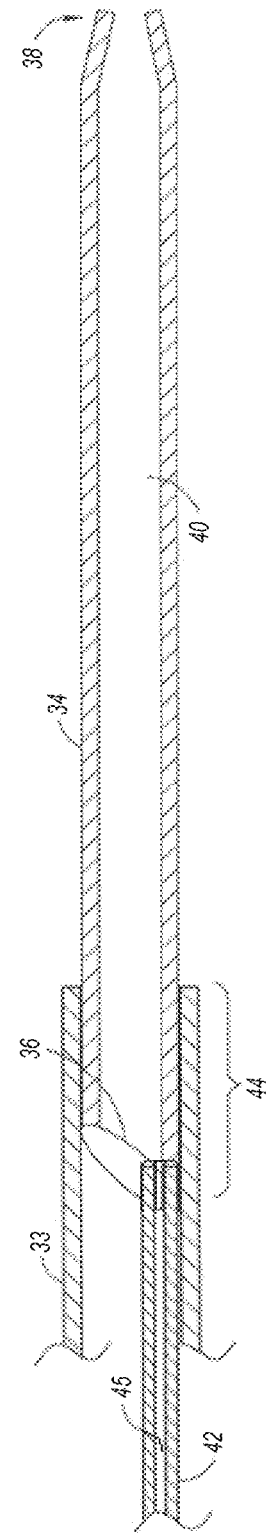

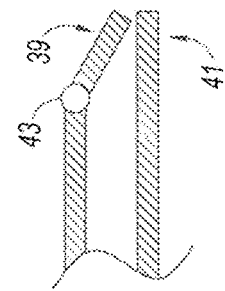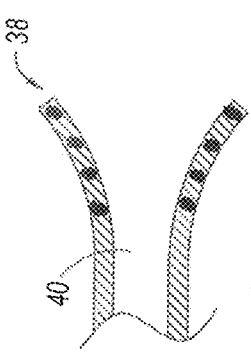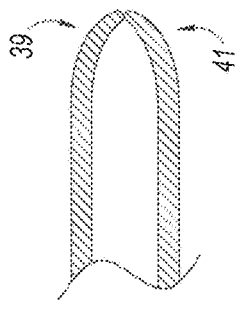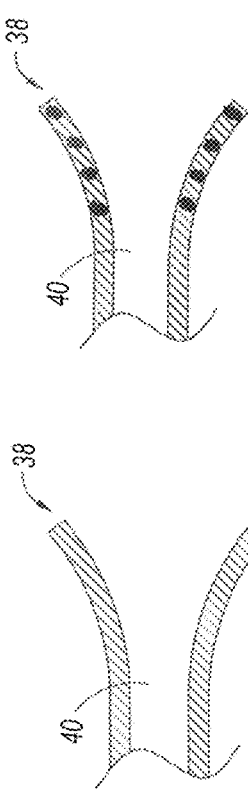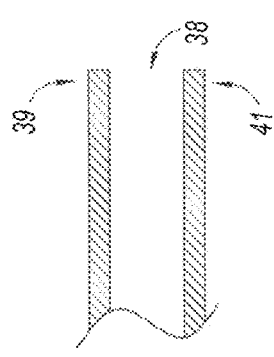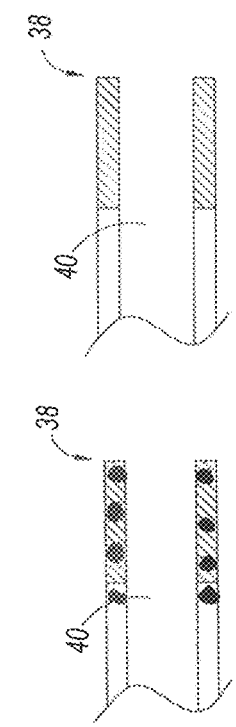

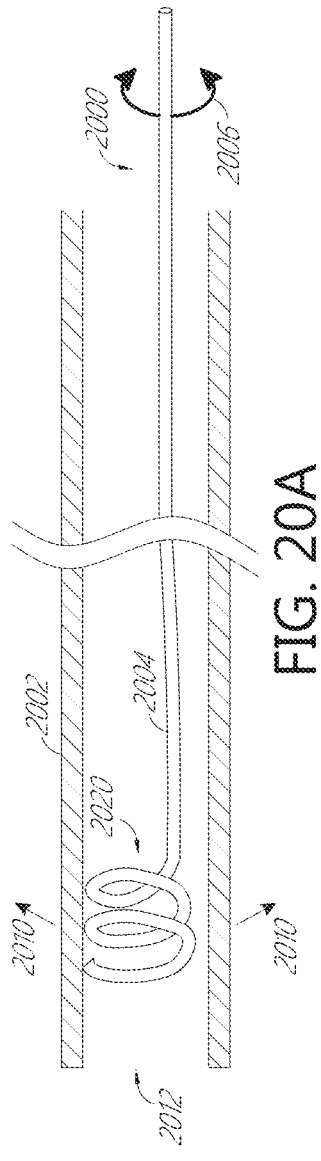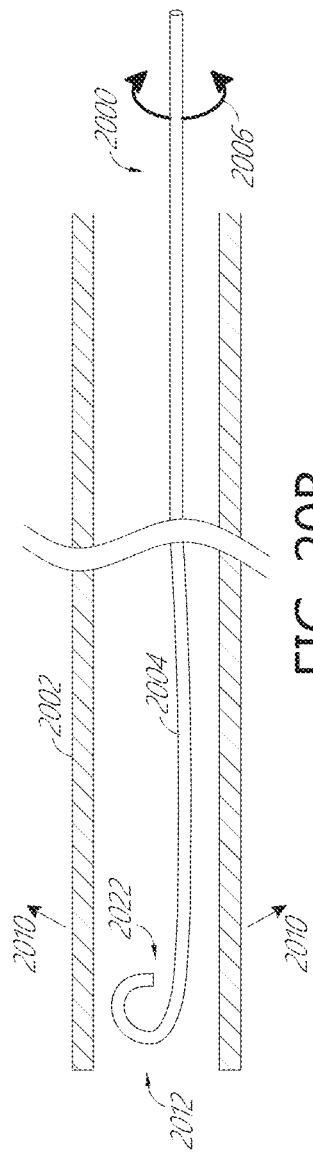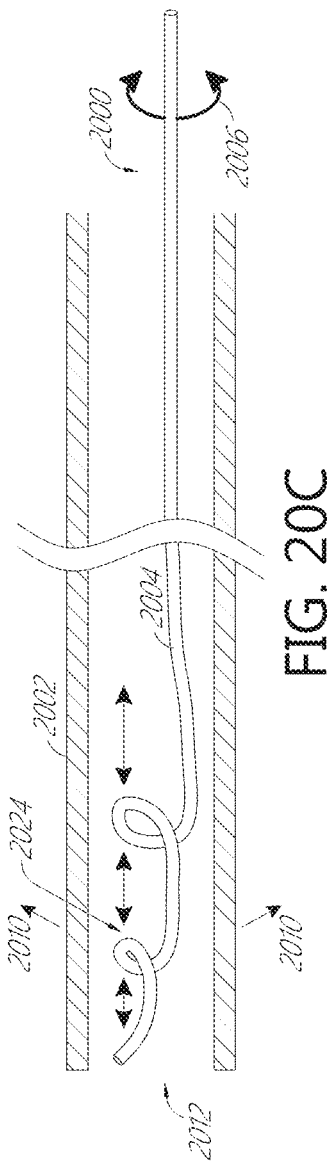

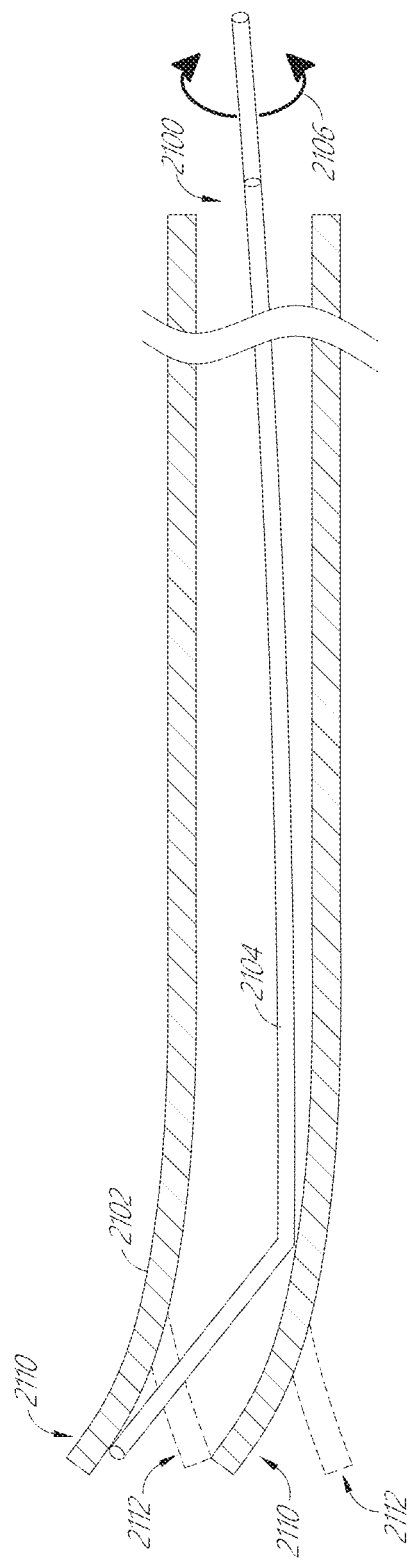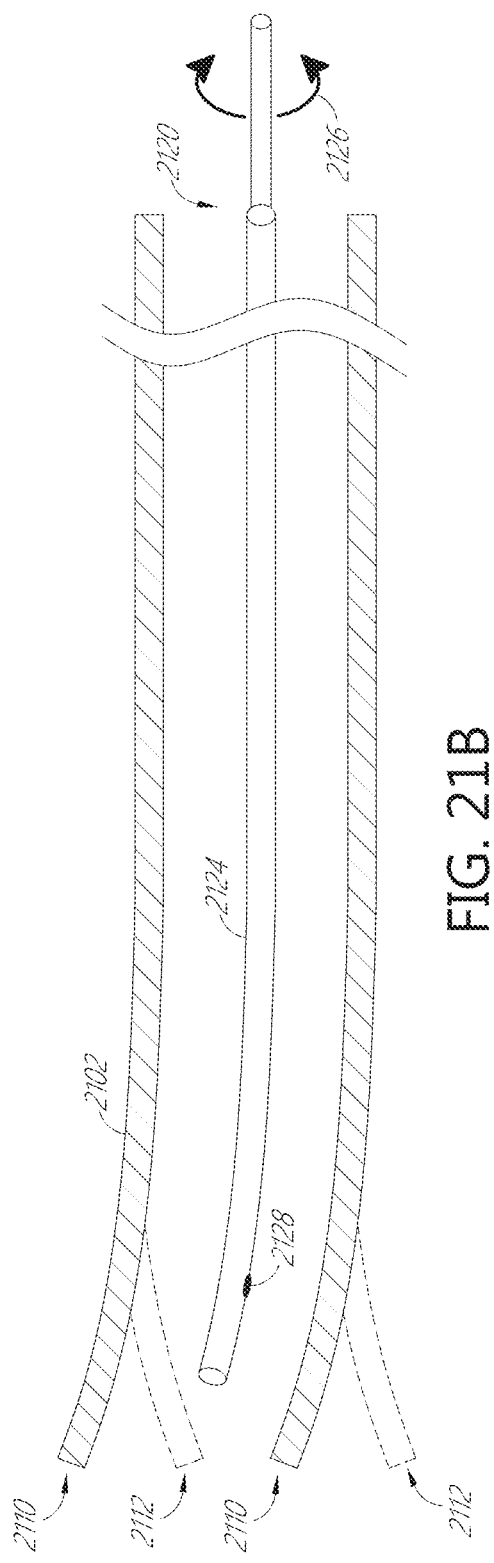
FIG. 21A
FIG. 21B

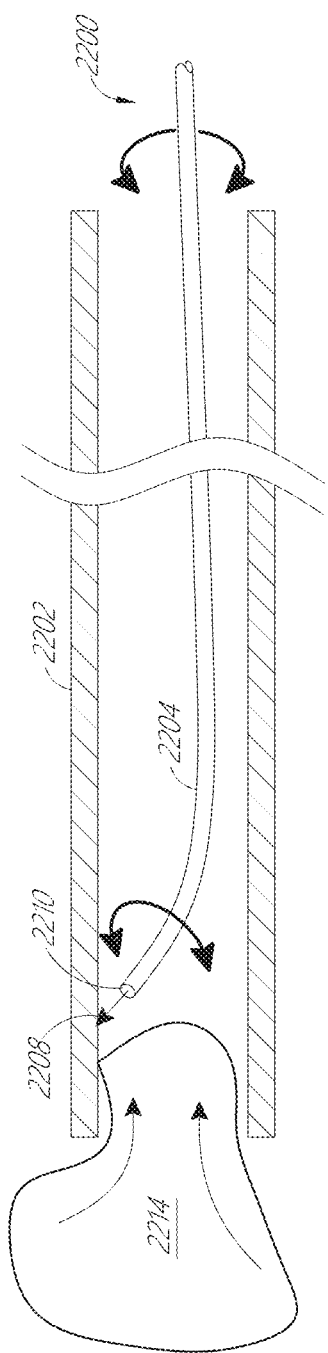
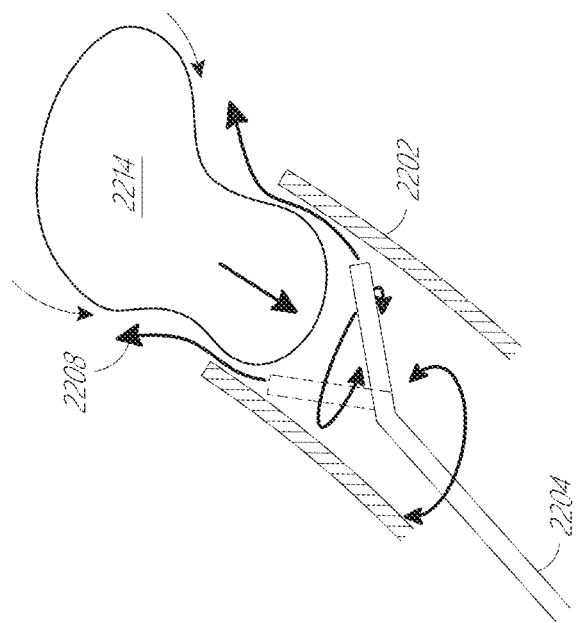
FIG. 22A
FIG. 22B

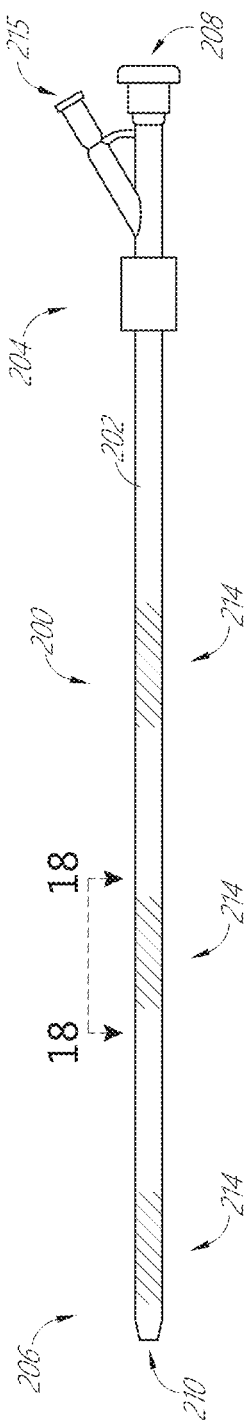
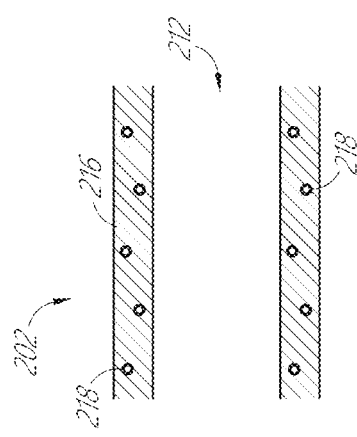
FIG. 38
FIG. 39

TELESCOPING NEUROVASCULAR CATHETER WITH ENLARGEABLE DISTAL OPENING

CROSS-REFERENCE TO RELATED APPLICATIONS

This application is a continuation application of U.S. patent application Ser. No. 15/442,393, filed Feb. 24, 2017, which claims the benefit of U.S. Provisional Application No. 62/299,418, filed Feb. 24, 2016, and U.S. Provisional Application No. 62/443,595, filed Jan. 6, 2017, the entirety of these applications are hereby incorporated by reference herein.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase®, for treating acute stroke. A randomized, double-blind trial, the National Institute of Neurological Disorders and t-PA Stroke Study, revealed a statistically significant improvement in stoke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy.

Finally, balloons or stents have been used to create a patent lumen through the clot when clot removal or dissolution was not possible.

Notwithstanding the foregoing, there remains a need for new devices and methods for treating vasculature occlusions in the body, including acute ischemic stroke and occlusive cerebrovascular disease.

SUMMARY OF THE INVENTION

There is provided in accordance with one aspect, a telescoping catheter, comprising: an elongate, flexible tubular body, comprising a proximal section having at least one lumen and a distal section axially movably positioned within the lumen; and a control for advancing the distal section from a first, proximally retracted position within the proximal section to a second, extended position, extending distally beyond the proximal section; and an active tip on the distal end of the distal section, comprising a distal opening that is movable between a smaller and a larger configuration.

In one aspect of present disclosure, the control comprises a pull wire extending through the proximal section. In another aspect of present disclosure, the distal section is distally advanceable to extend beyond the proximal section for a distance of at least about 10 cm. In yet another aspect of present disclosure, the distal section is distally advanceable to extend beyond the proximal section for a distance of at least about 25 cm.

In one aspect of present disclosure, the distal opening is movable in response to movement of a control wire. In another aspect of present disclosure, the distal opening is movable between a smaller and a larger configuration in response to application of vacuum to the lumen. In yet another aspect of present disclosure, the size of the distal opening is changed by lateral movement of a side wall on the distal section. In yet another aspect of present disclosure, the distal opening comprises at least one movable jaw. In another aspect of present disclosure, the distal end of the distal section comprises a duck bill valve configuration.

In one aspect of present disclosure, the telescoping catheter may further comprise a controller for applying intermittent vacuum to the lumen. The controller may be configured to apply pulses of vacuum to the lumen spaced apart by spaces of neutral pressure. The controller may be configured to alternate between applying pulses of higher negative pressure and lower negative pressure. The distal tip of the catheter may axially reciprocate in response to application of pulses of vacuum to the lumen.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

FIG. 1 is a side elevational schematic view of an intracranial aspiration catheter in accordance with the present invention, with a distal segment in a proximally retracted configuration.

FIG. 2 is a side elevational view as in FIG. 1, with the distal segment in a distally extended configuration.

FIGS. 3A-3B are cross-sectional elevational views of a distal end of catheter 10, with the distal section 34 fully extended.

FIGS. 4A-4C schematically illustrate different cutting tip configurations.

FIGS. 4D-4E and 4J-4K schematically illustrate a distal dynamic funnel tip configuration.

FIGS. 20A-20C depict agitators with various distal tip configurations.

FIGS. 21A-21B illustrate a moving or wiggling distal tip of a catheter in response to activating the agitator.

FIGS. 22A-22B illustrate media injection from a moving or wiggling distal tip of an agitator.

FIG. 38 is a side elevational schematic view of a transformable catheter in accordance with the present invention.

FIG. 39 is a cross-sectional view taken along the lines 18-18 of FIG. 38, showing heating elements within the catheter sidewall.

DETAILED DESCRIPTION OF THE PREFERRED EMBODIMENT

Figure 4F:
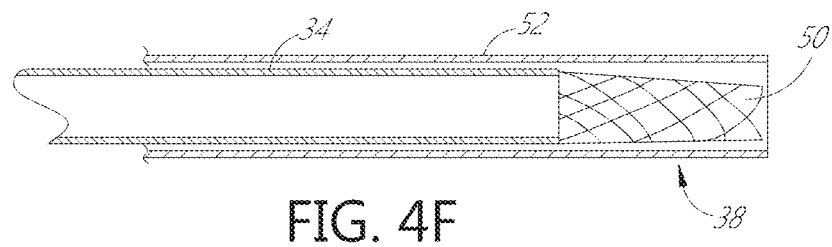
FIGS. 4F-4G illustrate a dynamic flared tip having a first restraint system.

Referring to FIG. 1, there is disclosed a catheter 10 in accordance with one aspect of the present invention. Although primarily described in the context of an axially extendable distal segment aspiration catheter with a single central lumen, catheters of the present invention can readily be modified to incorporate additional structures, such as permanent or removable column strength enhancing mandrels, two or more lumen such as to permit drug, contrast or irrigant infusion or to supply inflation media to an inflatable balloon carried by the catheter, or combinations of these features, as will be readily apparent to one of skill in the art in view of the disclosure herein. In addition, the present invention will be described primarily in the context of removing obstructive material from remote vasculature in the brain, but has applicability as an access catheter for delivery and removal of any of a variety of diagnostics or therapeutic devices with or without aspiration.

The catheters disclosed herein may readily be adapted for use throughout the body wherever it may be desirable to distally advance a low profile distal catheter segment from a larger diameter proximal segment. For example, axially extendable catheter shafts in accordance with the present invention may be dimensioned for use throughout the coronary and peripheral vasculature, the gastrointestinal tract, the urethra, ureters, Fallopian tubes and other lumens and potential lumens, as well. The telescoping structure of the present invention may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

In the illustrated embodiment, the tubular body 16 is divided into at least a fixed proximal section 33 and an axially extendable and retractable distal section 34 separated at a transition 32.

Referring to FIGS. 3A and 3B, there is illustrated a cross-sectional view of the distal segment 34 shown extended distally from the proximal segment 33 in accordance with the present invention. Distal segment 34 extends between a proximal end 36 and a distal end 38 and defines at least one elongate central lumen 40 extending axially therethrough. Distal end 38 may be provided with one or more movable side walls or jaws 39, which move laterally in the direction of an opposing side wall or jaw 41 under the influence of aspiration, to enable the distal end 38 to bite or break thrombus or other material into smaller particles, to facilitate aspiration through lumen 40. Both walls 39 and 41 may be movable towards and away from each other to break up thrombus as is discussed further below. For certain applications, the proximal section 33 may also or alternatively be provided with one or two opposing jaws, also responsive to vacuum or mechanical actuation to break up thrombus.

The inner diameter of the distal section 34 may be between about 0.030 inches and about 0.112 inches, between about 0.040 inches and about 0.102 inches, between about 0.045 inches and about 0.097 inches, between about 0.050 inches and about 0.092 inches, between about 0.055 inches and about 0.087 inches, between about 0.060 inches and about 0.082 inches, between about 0.062 inches and about 0.080 inches, between about 0.064 inches and about 0.078 inches, between about 0.066 inches and about 0.076 inches, between about 0.068 inches and about 0.074 inches, or between about 0.070 inches and about 0.072 inches.

The inner diameter and the outer diameter of the distal section 34 may be constant or substantially constant along its longitudinal length. Alternatively, the distal section 34 may be tapered near its distal end. The distal section 34 may be tapered at less than or equal to about 5 cm, about 10 cm, about 15 cm, about 20 cm, about 23 cm, about 25 cm, about 30 cm, about 31 cm, about 35 cm, about 40 cm, about 45 cm, about 50 cm, about 60 cm, or about 70 cm from its distal end.

The inner diameter of the distal section 34 may be tapered or decreased near the distal end by less than or equal to about 95%, about 90%, about 85%, about 80%, about 75%, about 70%, about 65%, about 60%, about 55%, about 50%, about 45%, about 40%, about 35%, about 30%, about 25%, about 20%, about 10%, or about 5%. The inner diameter of the distal section 34 may be tapered or decreased near the distal end by greater than or equal to about 95%, about 90%, about 85%, about 80%, about 75%, about 70%, about 65%, about 60%, about 55%, about 50%, about 45%, about 40%, about 35%, about 30%, about 25%, about 20%, about 10%, or about 5%. The tapered inner diameter of the distal section 34 may be by less than or equal to about 0.11 inches, about 0.1 inches, about 0.090 inches, about 0.080 inches, about 0.070 inches, about 0.065 inches, about 0.060 inches, about 0.055 inches, about 0.050 inches, about 0.045 inches, about 0.040 inches, about 0.035 inches, about 0.030 inches, about 0.025 inches, about 0.020 inches, about 0.015 inches, or about 0.010 inches.

The length of the distal section 34 may be between about 13 cm and about 53 cm, between about 18 cm and about 48 cm, between about 23 cm and about 43 cm, or between about 28 cm and about 38 cm. The length of the distal section 34 may be less than or equal to about 20 cm, about 25 cm, about 30 cm, about 33 cm, about 35 cm, about 40 cm, about 41 cm, about 45 cm, about 50 cm, about 55 cm, about 60 cm, about 70 cm, or about 80 cm. The length of the distal section 34 may depend on the degree of tapering of the internal diameter of the distal section 34.

The proximal end 36 of distal section 34 is provided with a proximally extending pull wire 42. Pull wire 42 extends proximally throughout the length of the tubular body 16, to control 24 which may be carried by manifold 18. Axial movement of control 24 produces a corresponding axial movement of distal section 34 with respect to proximal section 33 as has been discussed. Alternatively, the proximal end of pull wire 42 may exit through a port on manifold 18, such that it may be manually grasped and pulled or pushed by the clinician to extend or retract the distal section 34. The length of the pull wire 42 may be between about 700 mm and about 1556 mm, between about 800 mm and about 1456 mm, between about 850 mm and about 1406 mm, between about 900 mm and about 1356 mm, between about 950 mm and about 1306 mm, between about 1000 mm and about 1256 mm, between about 1020 mm and about 1236 mm, between about 1040 mm and about 1216 mm, between about 1060 mm and about 1196 mm, between about 1080 mm and about 1176 mm, between about 1100 mm and about 1156 mm, between about 1110 mm and about 1146 mm, or between about 1120 mm and about 1136 mm.

Upon distal advance of pull wire 42 to its limit of travel, an overlap 44 remains between the proximal end 36 of distal section 34 and the proximal section 33. This overlap 44 is configured to provide a seal to enable efficient transmission of vacuum from proximal section 33 to distal section 34. Overlap 44 may be provided with any of a variety of additional features to facilitate a seal, such as a gasket, coating or tightly toleranced sliding fit. Preferably the clearance between the OD of the distal section 34 and ID of the proximal section 33, at least in the vicinity of transition 32, will be no more than about 0.005 inches and preferably no more than about 0.003 inches to provide an effective seal in a blood environment.

Following positioning of the distal end of proximal section 33 within the vasculature, such as within the cervical carotid artery, the control 24 is manipulated to distally advance distal section 34 deeper into the vasculature. For this purpose, the pull wire 42 will be provided with sufficient column strength to enable distal advance of the distal tip 38 as will be discussed below.

The pull wire 42 and distal section 34 may be integrated into a catheter as illustrated in FIGS. 1 and 2. Alternatively, distal section 34 and pull wire 42 may be configured as a stand-alone catheter extension device as is discussed in greater detail below. The catheter extension device may be introduced into the proximal end of proximal section 33 after placement of proximal section 33 and advanced distally there through as illustrated in FIG. 3A, to telescopically extend the reach of the aspiration system.

Referring to FIG. 3B, the pull wire 42 may comprise a tubular wall having an axially extending central lumen 45. The central lumen 45 permits introduction of media such as lubricants, drugs, contrast agents or others into the distal section 34. In addition, the central lumen 45 extending through pull wire 42 permits introduction of an agitator as is discussed in greater detail below.

Referring to FIGS. 4A through 4C, the distal tip 38 may be provided any of a variety of structures which produce an active movement such as a biting action in response to the application of an activation force such as a vacuum in lumen 40. Alternatively, an axially movable control wire may be connected with respect to a side wall of the distal tip 38, to enable cutting action under positive mechanical force. FIG. 4A illustrates a distal tip 38 in an open configuration, while FIG. 4B illustrates distal tip 38 with opposing side walls 39 and 41 drawn together by the negative pressure in aspiration lumen 40. This may be accomplished by providing a tapered thickness in side walls 39 and 41, or a groove or living hinge which facilitates lateral movement of at least one of side wall 39 or 41.

Alternatively, referring to FIG. 4C, a pivot point or hinge 43 may be provided to enable lateral movement of side wall 39 to operate as a jaw. Two opposing side walls may be moveable medially and laterally with bilateral symmetry like a duck bill valve. Three or more jaws may be provided, such as three triangular jaws separated at about 120° spacing which under an aspiration pulse close to form a pyramid closed tip.

In some implementations of the present invention, the distal tip 14 is preferably provided with the capability to dilate beyond the nominal diameter of distal section 34. This provides a conical funnel like tip with an enlarged distal opening, to facilitate introduction of thrombotic material into the lumen 40. See FIGS. 4D-4K. The diameter at the distal opening of the fully opened funnel exceeds the diameter of a cylindrical extension of the adjacent tubular body by at least about 10%, preferably at least about 25% or 45% or more. This may be accomplished by providing the distal end 14 with an expandable material, or a plurality of laterally movable jaws or petals such as at least about three or five or six or more petals that are advanceable radially inwardly into a coaptive orientation, and radially outwardly to provide a flared inside diameter of aspiration lumen 40 which increases in the distal direction.

The flexible petals may be retained in a radially inwardly inclined configuration such as by application of negative pressure via lumen 40 during transluminal navigation of the distal section 34. Upon removal of the negative pressure, the panels may incline radially outwardly in response to a preset bias. Application of pulsatile vacuum may thereafter cause the panels to close radially inwardly to perform the biting function described previously.

The distal funnel opening may be actuated in a variety of other ways as will be apparent to those of skill in the art, such as by providing a pull wire or axially slideable outer or inner sleeve to open and close the funnel in response to mechanical movement of the wire or sleeve. Alternatively the funnel opening may be controlled by rotation of a control wire or tubular sleeve relative to the distal section 34, to activate an iris or spiral mechanism such as a helical ribbon or wire carried by the distal tip.

The normal state of the distal funnel may be a cylindrical configuration, and a mechanical, thermal or electrical actuator may be utilized to enlarge the distal funnel opening. Alternatively, the normal state of the funnel may be conical, and a mechanical, thermal or electrical actuator may be utilized to reduce the diameter such as for transluminal navigation. The petals or other wall of the funnel or elements disposed within the wall of the funnel may comprise a shape memory material such as a shape memory polymer or metal alloy such as nitinol, which may be laser cut from tube stock or woven into a fine mesh. The geometry of the funnel may be transformed by application of heat, such as body heat, or heat from a heat source carried by the catheter such as an electrical resistance wire within the wall or adjacent the catheter tip. Heat may alternatively be applied from a heat source introduced by way of central lumen 40, such as a heated fluid, or a removable heater such as an elongate flexible body carrying a resistance coil. Transformation of the funnel from one configuration to the other may alternatively be accomplished by reducing the temperature of the funnel below body temperature such as by introducing a cooled fluid into thermal communication with the funnel tip or providing the catheter or a removable cooling catheter with a Joule-Thomson expansion chamber located near the distal end.

In an alternate configuration, the sidewall of the funnel is provided with an inflatable balloon in the form of a ring or hoop, in communication with an inflation lumen extending throughout the length of the catheter. Introduction of inflation media inflates the annular balloon, transforming the configuration of the funnel tip from a reduced diameter to an enlarged diameter.

In an alternate configuration, the distal tip is biased into the funnel configuration, and restrained into a cylindrical configuration such as for transluminal navigation. When the funnel tip is desired to be enlarged, the restraint can be removed. The restraint may comprise an outer tubular covering membrane or loop configured to be removed by pulling a pull wire in a proximal direction. Alternatively, the restraint may be a bioabsorbable material, which dissolves following a preset amount of time that exceeds the anticipated time from vascular access to reach the final intravascular position.

Referring to FIGS. 4J-4K, the distal flared tip may comprise embedded elastic elements (e.g., a coil, struts or cage) such as spring steel, Nitinol or others known in the art that bias the tip into the flared configuration. The elastic elements such as in the form of a Nitinol cage may alternatively reside on the ID of the catheter. The polymer tip restrains the elastic elements to provide a cylindrical exterior configuration for transluminal navigation as seen in FIG. 4J. Softening the polymer (e.g., a hydrophilic blend) such as by body heat or moisture allows the elastic elements to transform the tip into the funnel configuration as seen in FIG. 4K. Alternatively, a conical NiTi cage at the tip is coated with a double hydrophilic non-cross linked glue. As the catheter advances the glue dissolves and gradually flares the tip into a funnel. The polymer tip may be formed without embedded elastic components and instead comprise a coextrusion with multiple layers, varying thickness in multiple layers, blending hydrophilic components at different ratios to control flaring. Multiple axially extending pull wires may be embedded through extruded lumen extending axially throughout the catheter wall. The wires are pushed or pulled to open/close the catheter distal end to flare or collapse. Funnel-shaped, underexpanded NiTi stent can be deployed at the tip area straddling between high and low durometer regions but greater length into high durometer region. Once ready to engage a clot, the stent can be pushed distally further into the low durometer tip. After complete clot retrieval the stent is pulled back into high durometer region, collapsing the funnel. This is an example of an active on-demand funneling tip.

Figure 4G:
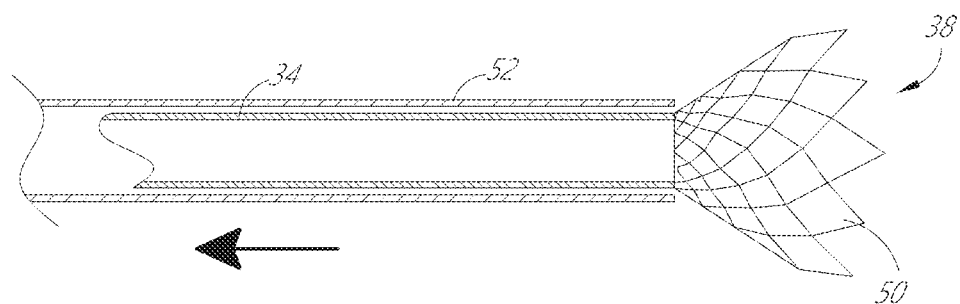

Referring to FIG. 4F, there is illustrated a cross-sectional view of a distal end of a tubular catheter body such as distal section 34. The tubular body is provided with a distal tip 38 in the form of a self expandable (e.g., NiTinol) mesh 50, constrained by an outer tubular restraint 52. Restraint 52 may comprise a proximately retractable tubular body extending proximally to a control on the proximal manifold; a peel away sheath carried by an elongate proximally retractable pull wire, or other mechanism disclosed elsewhere herein. As shown in FIG. 4G, proximal retraction of tubular restraint 52 with respect to tubular body 34, or distal advance of tubular body 34 with respect to restraint 52 exposes and releases the mesh 50 to self expand to a funnel shape to facilitate capture and removal of intravascular debris.

Figure 4H:
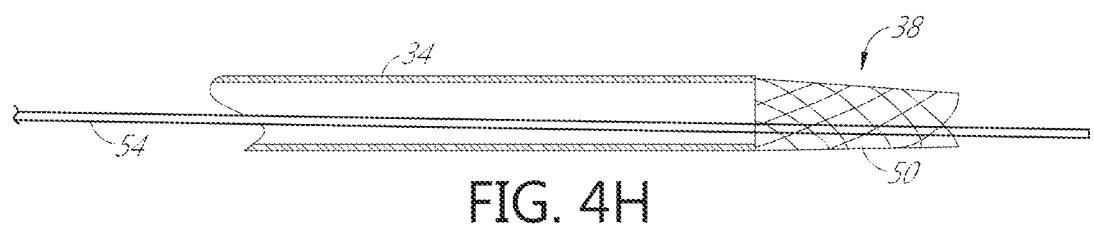
FIGS. 4H-4I illustrate a dynamic flared tip having an alternative restraint system.
Figure 4I:
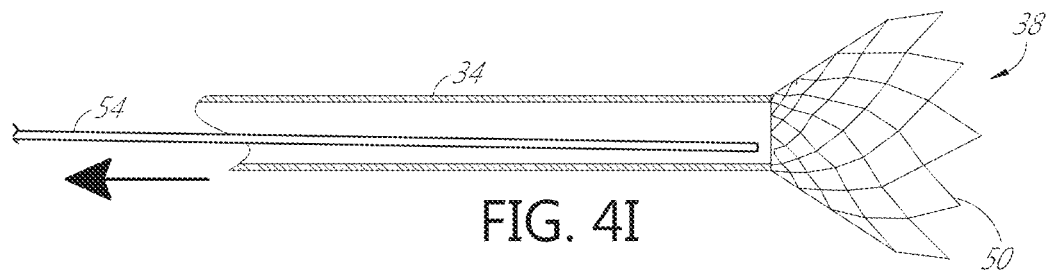

Referring to FIGS. 4H and 4I, the self expandable conical mesh 50 is restrained by interweaving an internal restraint wire 54. Restraint wire 54 may be a procedure guide wire, or a dedicated restraint wire. Proximal retraction of the restraint wire 54 releases the mesh 50, to self expanded to a final, funnel configuration. Release of the mesh 50 may be accomplished in a variety of alternative ways, such as bio absorbable materials, and electrolytic detachment.

The proximal end 12 of catheter 10 is additionally provided with a manifold 18 having one or more access ports as is known in the art. Generally, manifold 18 is provided with a proximal port such as a guidewire port 20 in an over-the-wire construction, and at least one side port such as aspiration port 22. Alternatively, the aspiration port 22 may be omitted if the procedure involves removal of the guidewire proximally from the guidewire port 20 following placement of the aspiration catheter, and aspiration through the guidewire port. Additional access ports and lumen may be provided as needed, depending upon the functional capabilities of the catheter. Manifold 18 may be injection molded from any of a variety of medical grade plastics, or formed in accordance with other techniques known in the art.

Manifold 18 may additionally be provided with a control 24, for controlling the axial position of the distal segment 34 of the catheter. Control 24 may take any of a variety of forms depending upon the mechanical structure and desired axial range of travel of the distal segment 34. In the illustrated embodiment, control 24 comprises a slider switch which is mechanically axially movably linked to the distal segment such that proximal retraction of the slider switch 24 produces a proximal movement of the distal segment 34. This retracts the distal segment 34 into the proximal section 33 as illustrated in FIG. 1. Distal axial advancement of the slider switch 24 produces a distal axial advance of the distal segment 34, as illustrated in FIGS. 2 and 3.

Any of a variety of controls may be utilized, including switches, buttons, levers, rotatable knobs, pull/push wires, and others which will be apparent to those of skill in the art in view of the disclosure herein. The control will generally be linked to the distal segment by a control wire 42.

Alternatively, the proximal section 33 and distal section 34 may be provided as separate devices, in which construction the proximal control may be omitted. The distal end of proximal section 33 may be provided with one or more jaws as has been discussed previously herein, for morcellating or otherwise breaking thrombus or other obstruction into pieces or otherwise facilitating aspiration. The proximal section 33 may additionally be mechanically coupled to or adapted for coupling to a source of vibrational or rotational movement, such as to provide the intermittent or pulsatile movement discussed elsewhere herein to facilitate navigation into the vasculature.

Using axial reciprocation, and/or rotation, and/or biting action of the distal jaws, the clinician may be able to reach the obstruction using proximal section 33. See, for example, FIG. 5 in which proximal section 33 is able to reach an obstruction in the left carotid siphon. If, however, the proximal section 33 is not able to advance sufficiently close to the obstruction, a separate telescoping distal section 34 may be introduced into the proximal section 33 and advanced therethrough and beyond, as illustrated in FIGS. 2 and 6-10, to reach the obstruction.

The cerebral circulation is regulated in such a way that a constant total cerebral blood flow (CBF) is generally maintained under varying conditions. For example, a reduction in flow to one part of the brain, such as in acute ischemic stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

Figure 5:
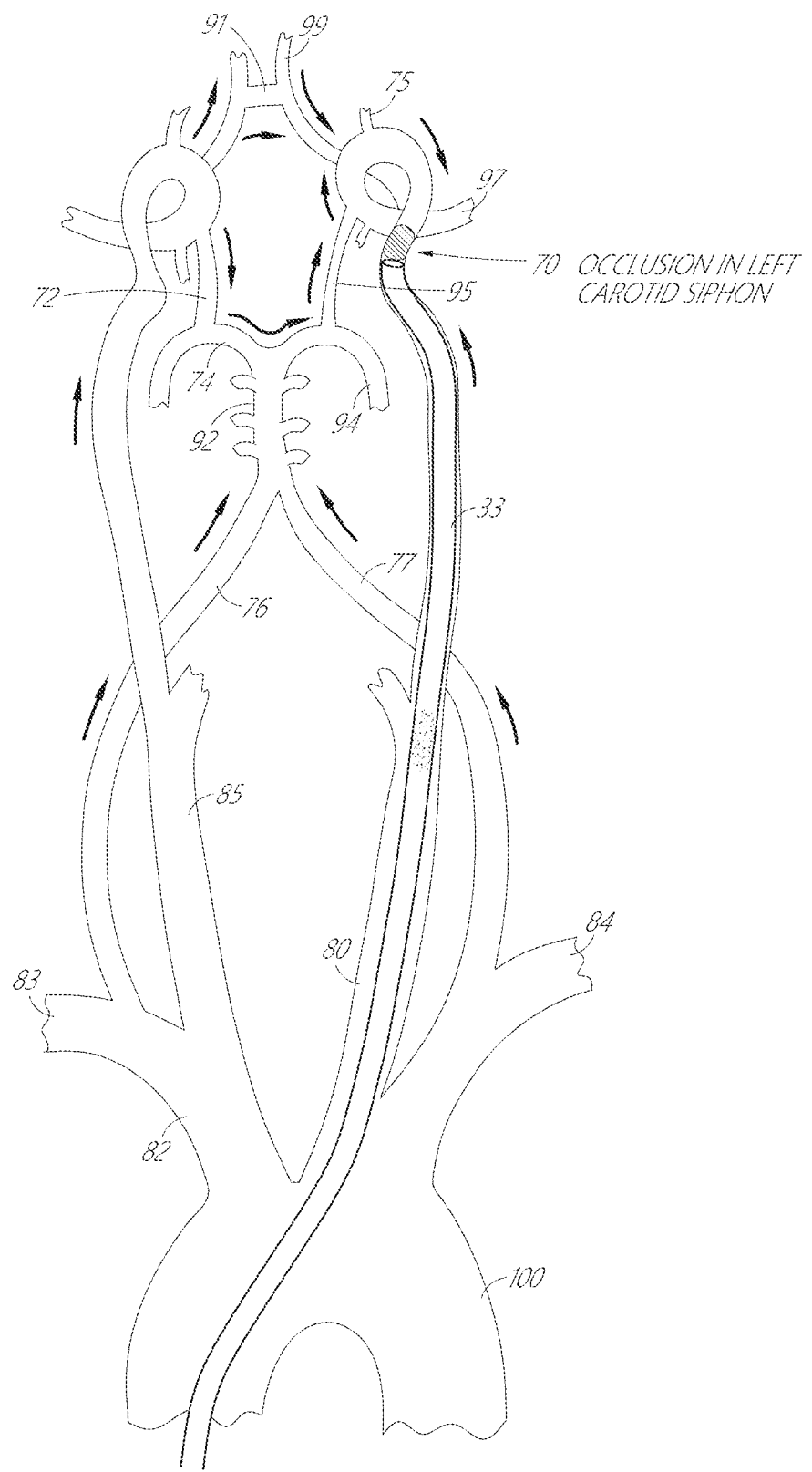
FIG. 5 depicts cerebral arterial vasculature including the Circle of Willis, and an access catheter positioned at an occlusion in the left carotid siphon artery.

FIG. 5 depicts cerebral arterial vasculature including the Circle of Willis. Aorta 100 gives rise to right brachiocephalic artery 82, left common carotid artery (CCA) 80, and left subclavian artery 84. The brachiocephalic artery 82 further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

When an occlusion occurs acutely, for example, in left carotid siphon 70, as depicted in FIG. 5, blood flow in the right cerebral arteries, left external carotid artery 78, right vertebral artery 76 and left vertebral artery 77 increases, resulting in directional change of flow through the Circle of Willis to compensate for the sudden decrease of blood flow in the left carotid siphon. Specifically, blood flow reverses in right posterior communicating artery 72, right PCA 74, left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal the occlusion to provide perfusion to the ischemic area distal to the occlusion.

As illustrated in FIG. 5, the proximal segment of catheter 10 is transluminally navigated along or over the guidewire, to the proximal side of the occlusion. Transluminal navigation may be accomplished with the distal section 34 of the catheter in the first, proximally retracted configuration. This enables distal advance of the proximal section 33 until further progress is inhibited by small and/or tortuous vasculature. Alternatively, the distal section 34 is a separate device, and is not inserted into the proximal section 33 until it is determined that the proximal section 33 cannot safely reach the occlusion. In the example illustrated in FIG. 5, the occlusion may be safely reached by the proximal section 33, without the need to insert or distally extend a distal section 34.

The distal end of the proximal section 33 of aspiration catheter 10 is inserted typically through an incision on a peripheral artery over a guidewire and advanced as far as deemed safe into a more distal carotid or intracranial artery, such as the cervical carotid, terminal ICA, carotid siphon, MCA, or ACA. The occlusion site can be localized with cerebral angiogram or IVUS. In emergency situations, the catheter can be inserted directly into the symptomatic carotid artery after localization of the occlusion with the assistance of IVUS or standard carotid doppler and TCD.

If it does not appear that sufficient distal navigation of the proximal section 33 to reach the occlusion can be safely accomplished, the distal section 34 is inserted into the proximal port 20 and/or distally extended beyond proximal section 33 until distal tip 38 is positioned in the vicinity of the proximal edge of the obstruction.

Figure 6:
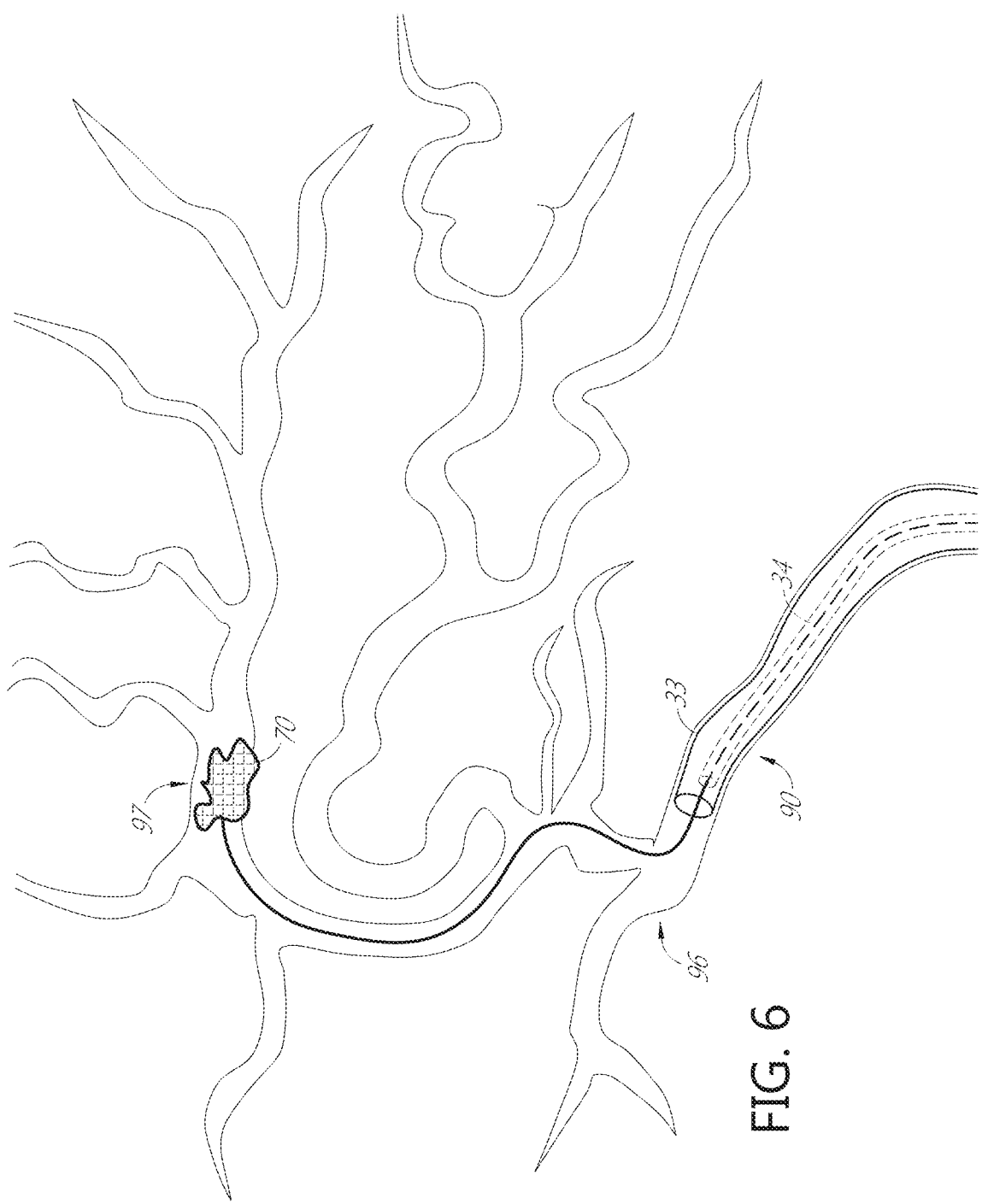
FIGS. 6 through 9 show a sequence of steps involved in positioning of the catheter and aspirating obstructive material from the middle cerebral artery.
Figure 7:
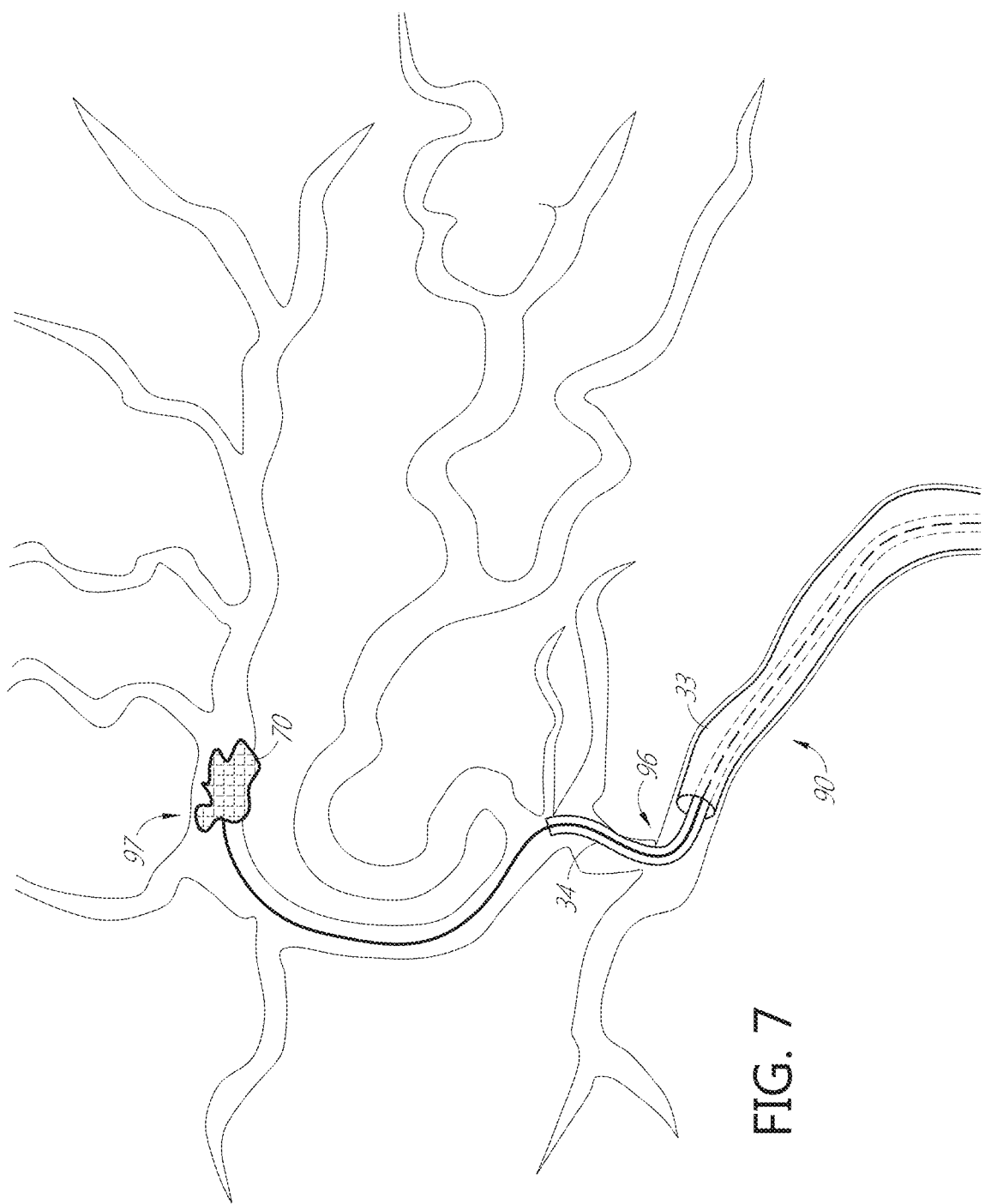
Figure 8:
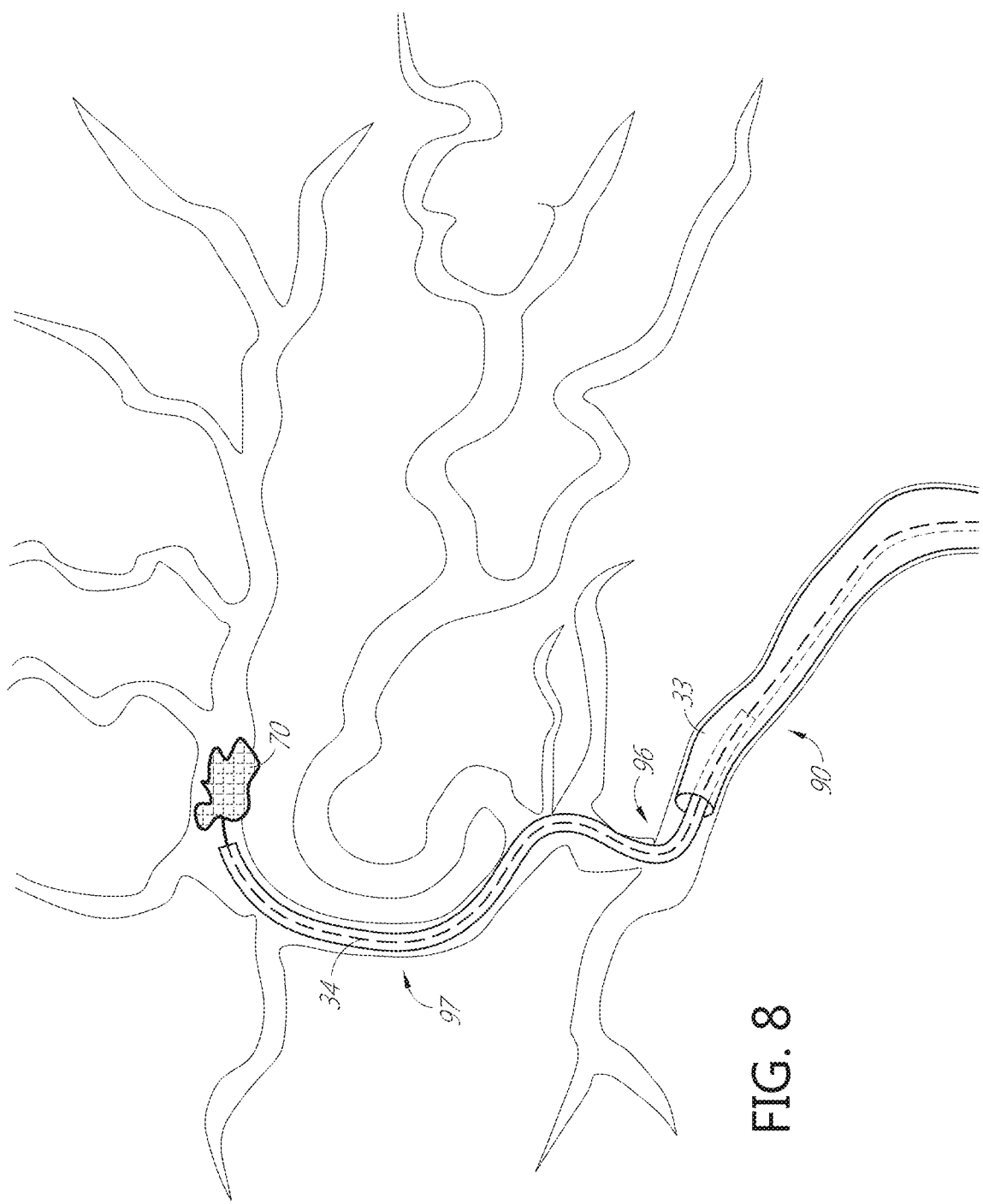

Referring to FIG. 6, an obstruction 70 is lodged in the middle cerebral artery 97. Proximal section 33 is positioned in the ICA and not able to navigate beyond a certain point such as at the branch 96 to the MCA artery 97. The proximal section 33 may be provided with a distal section 34 carried there in. Alternatively, a separate distal section 34 may be introduced into the proximal end of proximal section 33 once the determination has been made that the obstruction 70 cannot be reached directly by proximal section 33 alone. As seen in FIGS. 7 and 8, the distal section 34 may thereafter be transluminally navigated through the distal tortuous vasculature between proximal section 33 and the obstruction 70.

Figure 9:
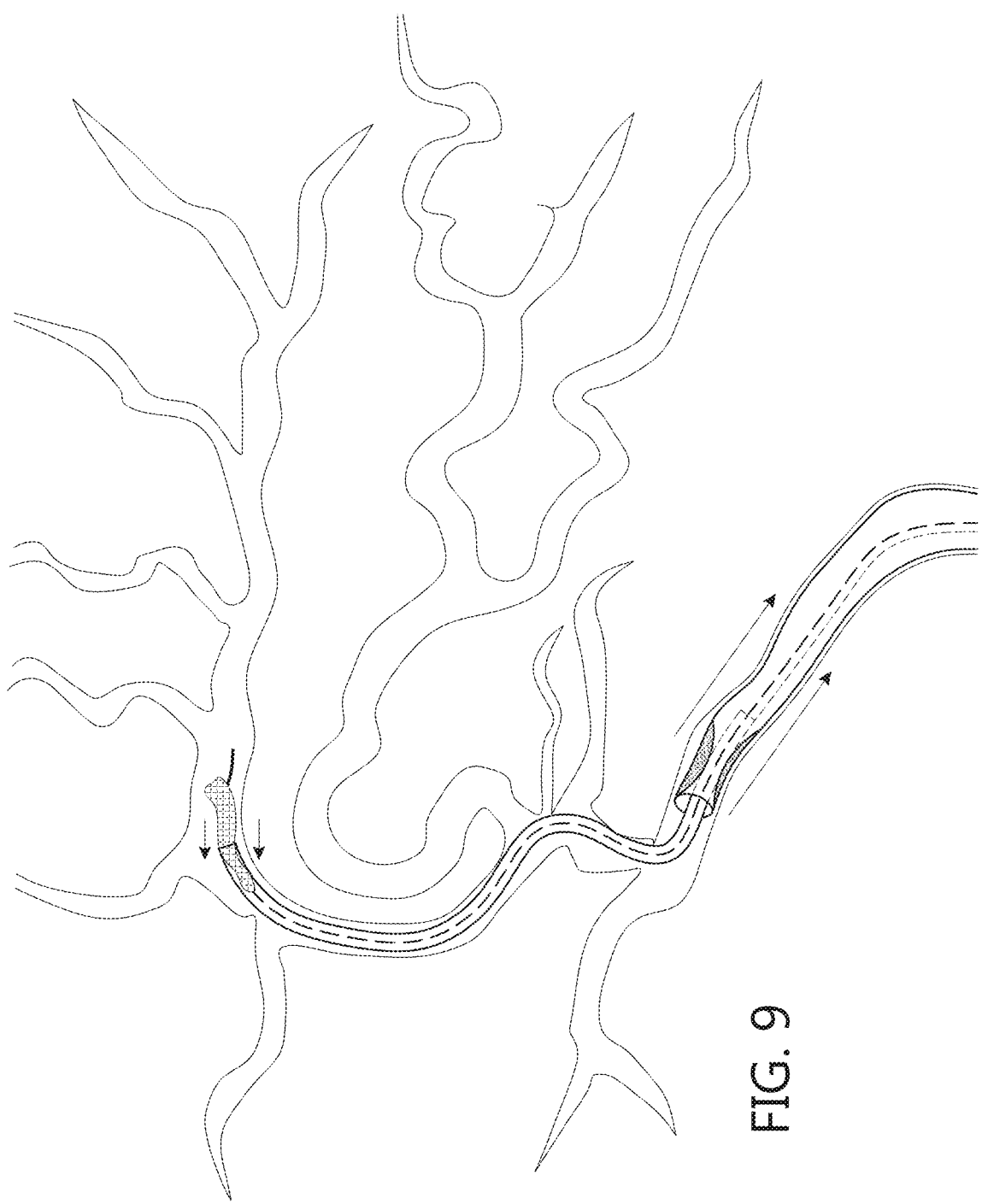
Figure 10:
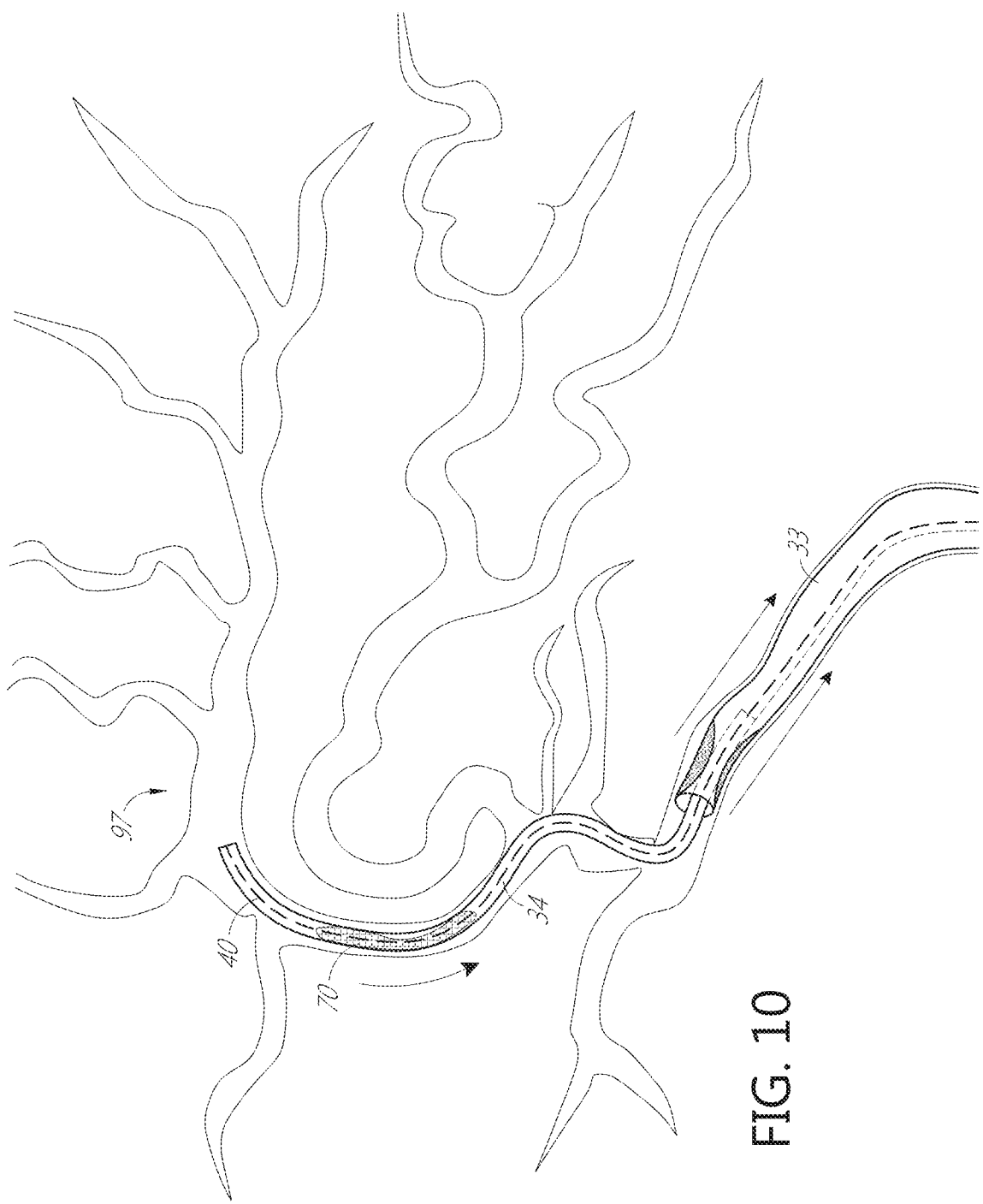
FIG. 10 illustrates removal of the catheter following aspiration of obstructive material.

Referring to FIG. 9, the obstruction 70 may thereafter be drawn into distal section 34 upon application of constant or pulsatile negative pressure with or without the use of jaws or other activation on the distal end of distal section 34 as discussed elsewhere herein. Once the obstruction 70 has either been drawn into distal section 34, or drawn sufficiently into distal section 34 that it may be proximately withdrawn from the body, proximal section 33 and distal section 34 are thereafter proximally withdrawn.

Aspiration may be applied via lumen 40, either in a constant mode, or in a pulsatile mode. Preferably, pulsatile application of vacuum will cause the distal tip 38 to open and close like a jaw, which facilitates reshaping the thrombus or biting or nibbling the thrombus material into strands or pieces to facilitate proximal withdrawal under negative pressure through lumen 40. Application of aspiration may be accompanied by distal advance of the distal tip 38 into the thrombotic material.

Pulsatile application of a vacuum may oscillate between positive vacuum and zero vacuum, or between a first lower negative pressure and a second higher negative pressure. Alternatively, a slight positive pressure may be alternated with a negative pressure, with the application of negative pressure dominating to provide a net aspiration through the lumen 40. Pulse cycling is discussed in greater detail in connection with FIG. 25.

The proximal manifold and/or a proximal control unit (not illustrated) connected to the manifold may enable the clinician to adjust any of a variety of pulse parameters including pulse rate, pulse duration, timing between pulses as well as the intensity of the pulsatile vacuum.

The distal section may thereafter be proximally retracted into proximal section 33 and the catheter proximally retracted from the patient. Alternatively, proximal retraction of the catheter 10 may be accomplished with the distal section 34 in the distally extended position. A vasodilator, e.g., nifedipine or nitroprusside, may be injected through a second lumen to inhibit vascular spasm induced as a result of instrumentation.

Pressure may be monitored by a manometer carried by the catheter or a wire positioned in a lumen of the catheter. A pressure control and display may be included in the proximal control unit or proximal end of the catheter, allowing suction within the vessel to be regulated.

Focal hypothermia, which has been shown to be neuroprotective, can be administered by perfusing hypothermic oxygenated blood or fluid. Moderate hypothermia, at approximately 32 to 34° C., can be introduced during the fluid infusion. Perfusion through a port on manifold 18 can be achieved by withdrawing venous blood from a peripheral vein and processing through a pump oxygenator, or by withdrawing oxygenated blood from a peripheral artery, such as a femoral artery, and pumping it back into the carotid artery.

If continuous and/or intermittent suction fails to dislodge the occlusion, a thrombolytic agent, e.g., t-PA, can be infused through central lumen 40 or a second lumen to lyse any thrombotic material with greater local efficacy and fewer systemic complications. Administration of thrombolytic agent, however, may not be recommended for devices which are inserted directly into the carotid artery due to increased risk of hemorrhage.

The intensity of intermittent or pulsatile vacuum applied to lumen 40 may be adjusted to cause the distal tip 38 of the catheter 10 to experience an axial reciprocation or water hammer effect, which can further facilitate both transluminal navigation as well as dislodging or breaking up the obstruction. Water hammer, or more generally fluid hammer, is a pressure surge or wave caused when a fluid in motion is forced to stop or change direction suddenly, creating a momentum change. A water hammer commonly occurs when a valve closes suddenly at the end of a pipeline system, and a pressure wave propagates in the pipe. A pressure surge or wave is generated inside the lumen 40 of the aspiration catheter 10 when a solenoid or valve closes and stops the fluid flow suddenly, or other pulse generator is activated. As the pressure wave propagates in the catheter 10, it causes the catheter 10 to axially vibrate. Since vibration can reduce surface friction between the outer diameter of the catheter 10 and the inner diameter of the vessel wall, it enables catheter to track through tortuous anatomies as well as assist capturing thrombus.

Referring to FIGS. 11A-11F, the cerebral circulation 1100 is simplified for the ease of demonstrating procedural steps. A thrombotic occlusion 1102 is in the right middle cerebral artery (RMCA) 1104. The RMCA 1104 branches from the right internal carotid artery (RICA) 1106. The RICA 1106 branches from the right common carotid artery (RCCA) (not shown). The RICA 1106 comprises cerebral 1108 (most distal from the aorta 100), cavernous 1110, and petrous 1112 (most proximal from the aorta 100) segments. The RCCA branches from the brachiocephalic artery. The brachiocephalic artery branches from the arch 1114 of the aorta 100.

Figure 11A:
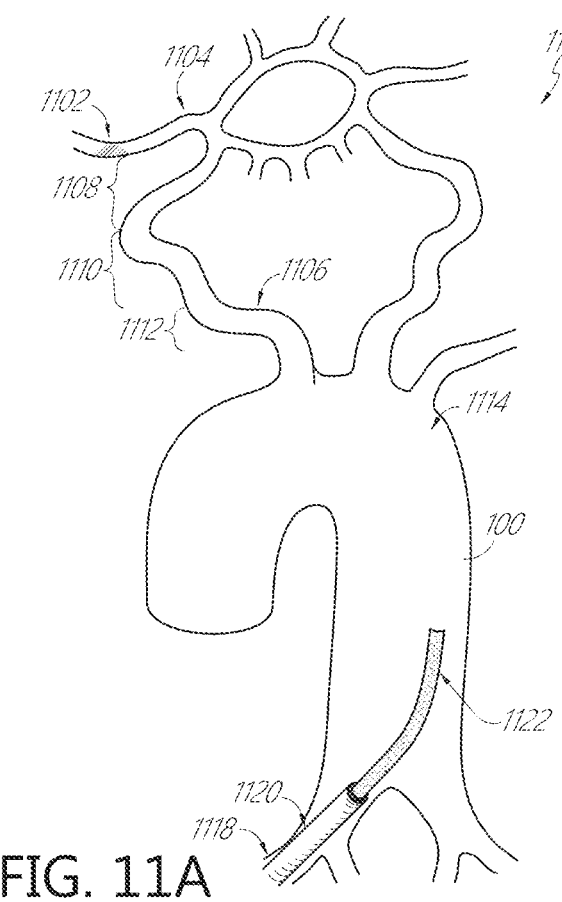
FIGS. 11A-11F depict a sequence of steps to access a neurovascular occlusion for aspiration.

The procedural steps for aspirating a thrombotic occlusion are described as follows. Referring to FIG. 11A, an introducer sheath 1120 is introduced at the femoral artery 1118. The outer diameter of the introducer sheath 1120 may be equal to or less than about 12 F, 11 F, 10 F, 9 F, 8 F, 7 F, or 6 F. Then, a guide sheath 1122 is inserted through the introducer sheath 1120. The outer diameter of the guide sheath 1122 may be equal to or less than about 9 F, 8 F, 7 F, 6 F, 5 F, 4 F, or 3 F, and the inner diameter of the introducer sheath 1120 may be greater than the outer diameter of the guide sheath 1122.

Figure 11B:
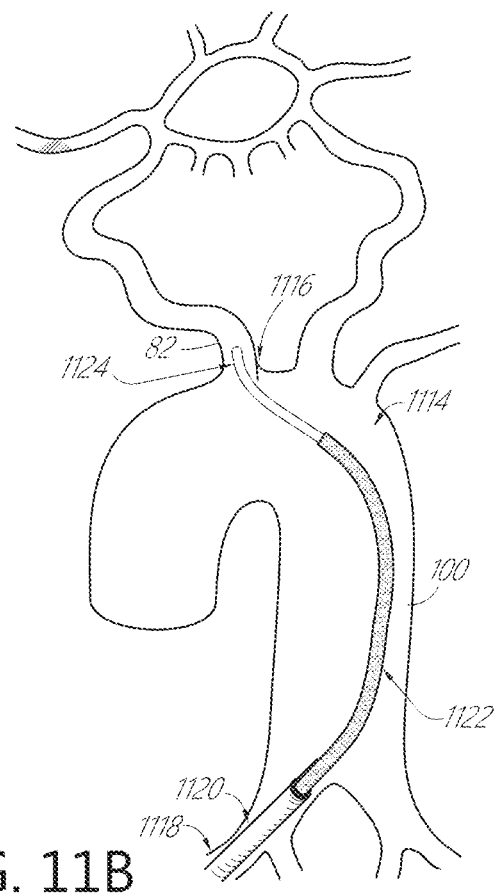

Referring to FIG. 11B, an insert catheter 1124 is inserted through the guide sheath 1122. The outer diameter of the insert catheter 1124 may be equal to or less than about 9 F, 8 F, 7 F, 6 F, 5 F, 4 F, or 3 F, and the inner diameter of the guide sheath 1122 may be greater than the outer diameter of the insert catheter 1124. In some cases, a first guidewire 1126 may be introduced through the insert catheter 1124 (not shown in FIG. 11B). Then, the guide sheath 1122, the insert catheter 1124, and optionally the first guidewire 1126 are tracked up to the aortic arch 1114. The insert catheter 1124 is used to engage the origin of a vessel. In FIG. 11B, the insert catheter 1124 engages the origin 1116 of the brachiocephalic artery 82. An angiographic run is performed by injecting contrast media through the insert catheter 1124. In the cases where the first guidewire 1126 is used before the angiographic run, the first guidewire 1126 is removed prior to injecting the contrast media.

Figure 11C:
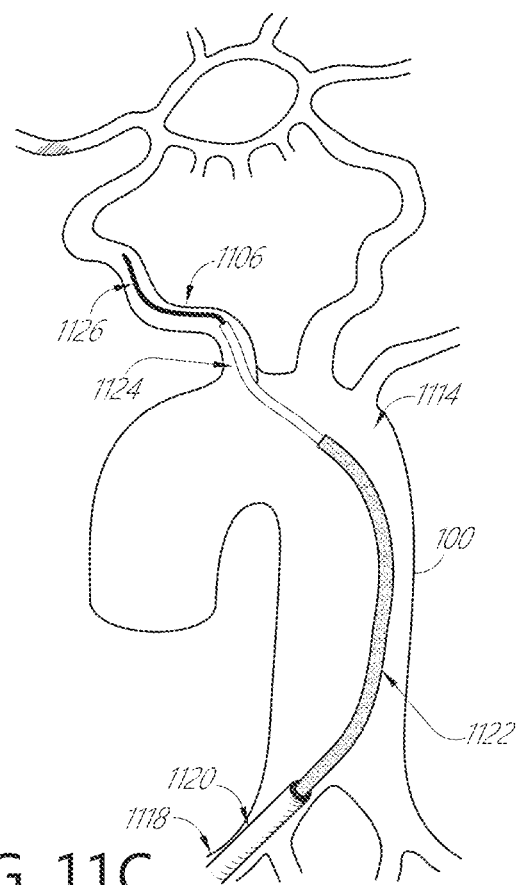
Figure 11D:
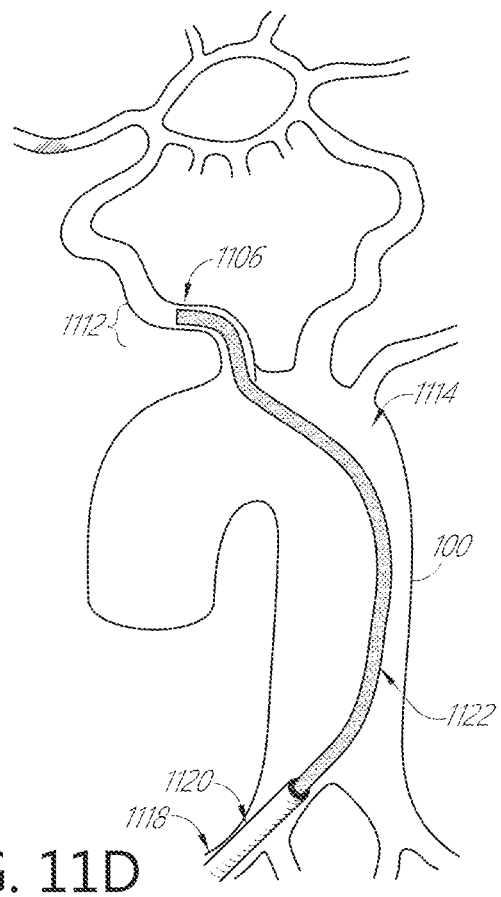

Referring to FIG. 11C, the first guidewire 1126 is inserted through the lumen of the insert catheter 1124. Then, the first guidewire 1126, the insert catheter 1124, and the guide sheath 1122 are advanced together to the ICA 1106. Referring to FIG. 11D, due to the stiffness of a typical guide sheath 1122 currently available in the market (e.g., Neuron MAX System produced by Penumbra Inc.), the most distal vessel that the guide sheath 1122 could navigate to is the petrous segment 1112 of the ICA 1106. Once the first guidewire 1126, the insert catheter 1124, and the guide sheath 1122 are advanced to the ICA 1106, both the first guidewire 1126 and the insert catheter 1124 are removed.

Figure 11E:
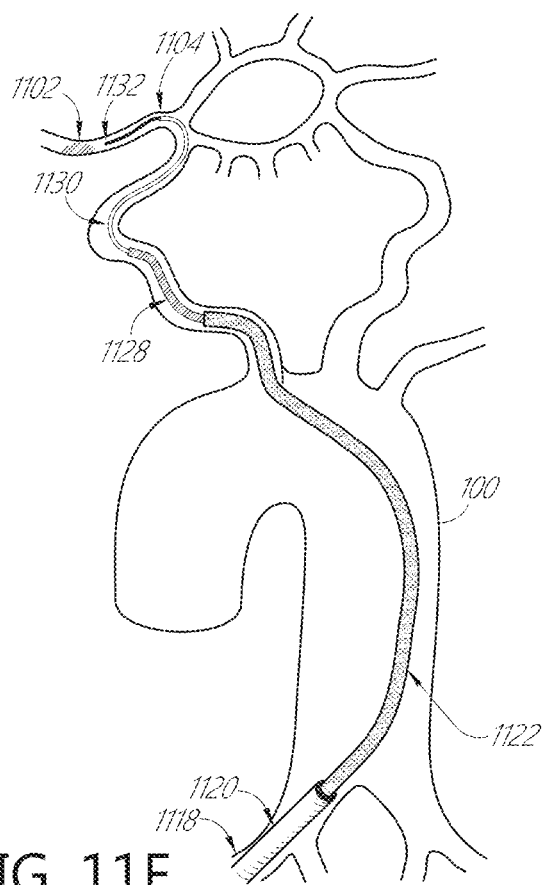

Referring to FIG. 11E, a second guidewire 1132 loaded inside the central lumen of a reperfusion catheter 1130 (e.g., 3 Max), which is loaded inside the central lumen of an aspiration catheter 1128 (e.g., ACE 68), are introduced through the guide sheath 1122. The diameter of the second guidewire 1132 may be equal to or less than about 0.03", about 0.025", about 0.02", about 0.016", about 0.014", about 0.01", or about 0.005". The inner diameter of the reperfusion catheter 1130 may be greater than the outer diameter of the second guidewire 1132. The inner diameter of the aspiration catheter 1128 may be greater than the outer diameter of the reperfusion catheter 1130. The inner diameter of the guide sheath 1122 may be greater than the outer diameter of the aspiration catheter 1128. Then, the second guidewire 1132 is advanced distally and positioned at the proximal end of the clot 1102 in the MCA 1104.

Figure 11F:
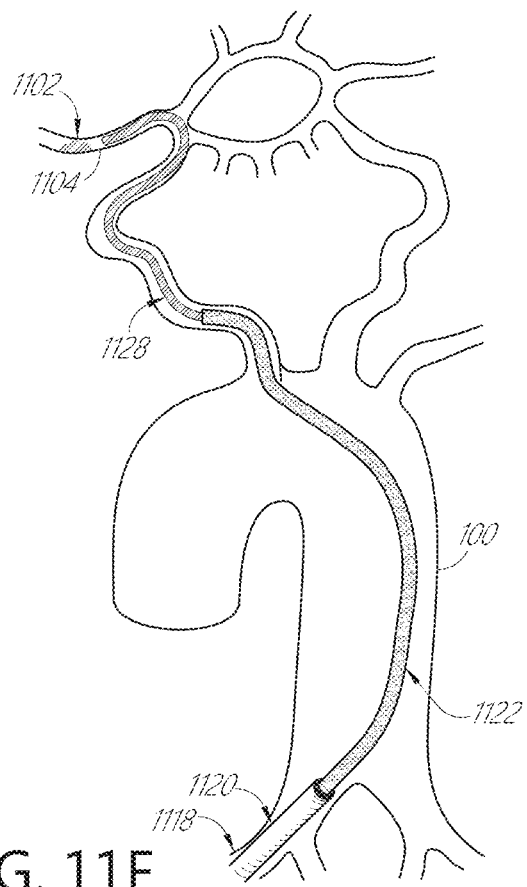

Referring to FIG. 11F, the aspiration catheter 1128 is tracked over the reperfusion catheter 1130 and the second guidewire 1132 to the proximal end of the clot 1102 in the MCA 1104. Both the second guidewire 1132 and the reperfusion catheter 1130 are removed. A vacuum pressure is then applied at the proximal end of the aspiration catheter 1128 to aspirate the clot 1102 through the central lumen of the aspiration catheter 1128.

A preferable, simplified method for aspirating a thrombotic occlusion in accordance with the present invention is described in connection with FIGS. 12A-12F. As illustrated in FIGS. 12A-12F, the cerebral circulation 1200 is simplified for the ease of demonstrating procedural steps. The alternative steps for aspirating a thrombotic occlusion make use of a transitional guidewire and a transitional guide sheath. The transitional guidewire has a soft and trackable distal segment with a smaller diameter so that the transitional guidewire may be advanced deeper than the guidewire 1126 described in FIG. 11C. In addition, the transitional guide sheath has a soft and trackable distal segment such that the transitional guide sheath may be advanced deeper than the guide sheath 1122 described in FIG. 11D. Using a transitional guidewire and a transitional guide sheath that can be advanced to an area near the clot eliminates the need to use a second guidewire or a reperfusion catheter to reach the clot.

Figure 12A:
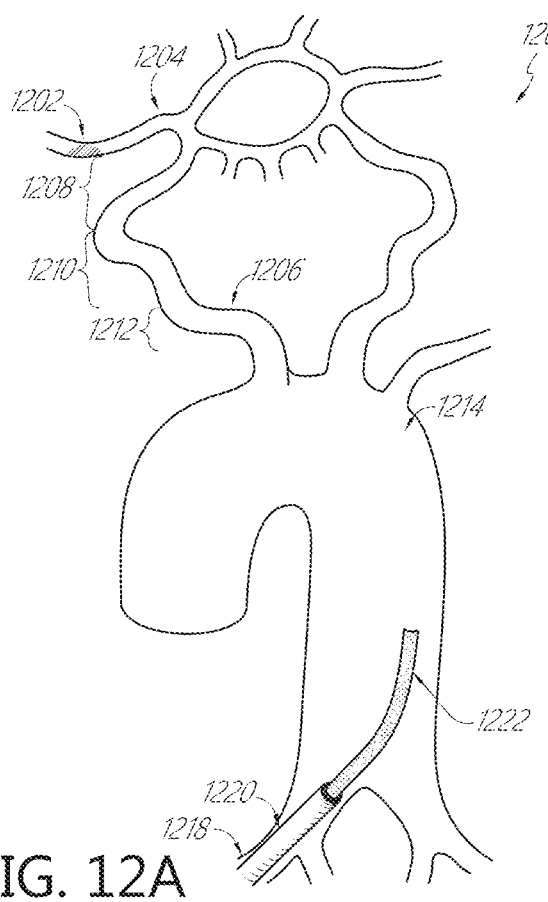
FIGS. 12A-12F depict an alternative sequence of steps in accordance with an aspect of the present invention involved in accessing a neurovascular occlusion for aspiration.
Figure 12B:
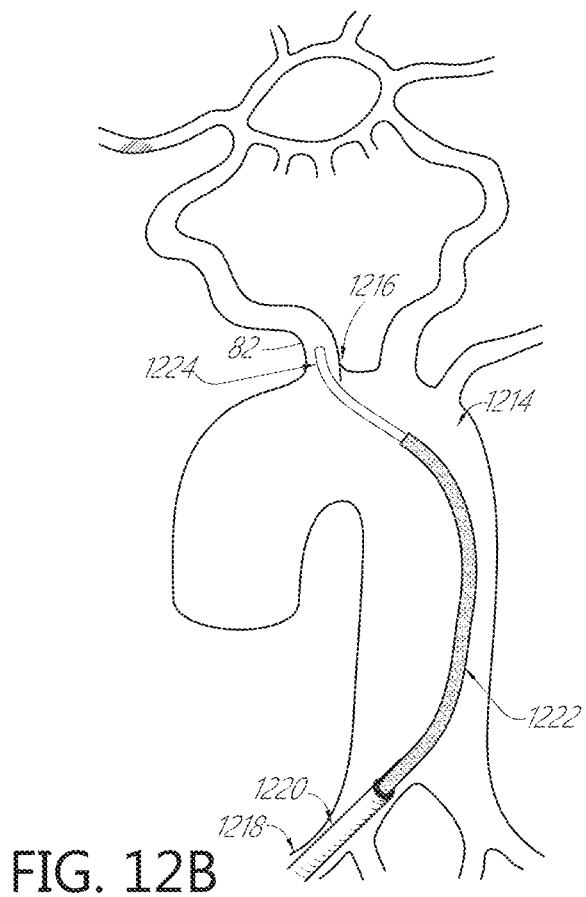

Referring to FIG. 12A, an introducer sheath 1220 is introduced at the femoral artery 1218. The outer diameter of the introducer sheath 1220 may be equal to or less than about 12 F, 11 F, 10 F, 9 F, 8 F, 7 F, or 6 F. Then, a transitional guide sheath 1222 such as the combination access and aspiration catheter discussed in greater detail below is inserted through the introducer sheath 1120 at the femoral artery 1218. The outer diameter of the guide sheath 1222 may be equal to or less than about 9 F, 8 F, 7 F, 6 F, 5 F, 4 F, or 3 F. Referring to FIG. 12B, an insert catheter 1224 is inserted through the transitional guide sheath 1222. The outer diameter of the insert catheter 1224 may be less than about 9 F, 8 F, 7 F, 6 F, 5 F, 4 F, or 3 F, and the inner diameter of the transitional guide sheath 1222 may be greater than the outer diameter of the insert catheter 1224. In some cases, a first guidewire may be introduced through the insert catheter 1224 (not shown in FIG. 12B). The diameter of the proximal section of the first guidewire may be equal to or less than about 0.079", about 0.066", about 0.053", about 0.038", about 0.035", about 0.030", or about 0.013".

The transitional guide sheath 1222, the insert catheter 1224, and optionally the first guidewire are tracked up to the aortic arch 1214. See FIG. 12B. The insert catheter 1224 may be used to select the origin of a vessel. In FIG. 12B, the insert catheter 1224 engages the origin 1216 of the brachiocephalic artery 82. An angiographic run may be performed by injecting contrast media through the insert catheter 1224. In the cases where the first guidewire is used before the angiographic run, the first guidewire is preferably removed prior to injecting the contrast media.

Figure 12C:
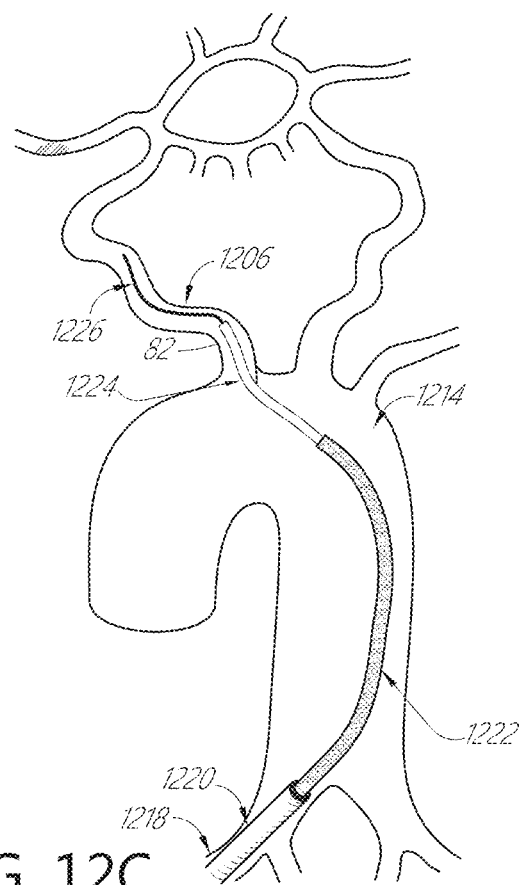
Figure 12D:
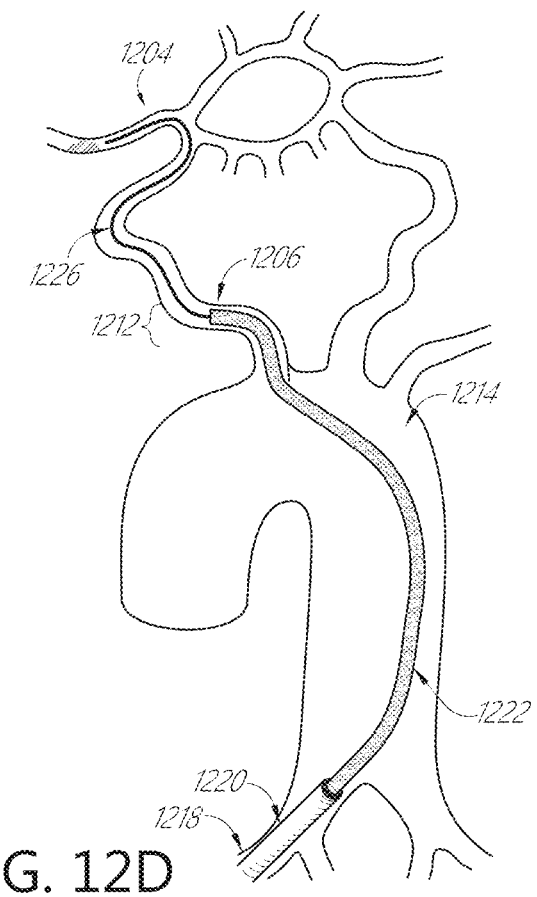

Referring to FIG. 12C, the transitional guidewire 1226 is inserted through the lumen of the insert catheter 1224 or guide sheath 1222. The diameter of at least a portion of the transitional guidewire 1226 (e.g., proximal diameter) is substantially similar to that of the first guidewire 1126. The diameter of at least a portion of the transitional guidewire 1226 (e.g., distal diameter) may be smaller than that of the first guidewire 1126 and may have a diameter along a proximal segment of at least about 0.030" and in one implementation about 0.038". A transition begins within the range of from about 15 cm-30 cm from the distal end, and typically no more than about 20 cm or 25 cm from the distal end, distally of which the diameter tapers down to no more than about 0.018" and in one implementation about 0.016". Referring to FIG. 12D, if utilized, the insert catheter 1224 may be removed because it is too stiff to be advanced to the MCA 1204. In certain implementations of the invention, the transitional guidewire 1226 provides sufficient back up support that the combination access and aspiration catheter 1224 may be advanced directly over the transitional guidewire without any intervening devices. Then, the transitional guidewire 1226 is advanced to the MCA 1204. The transitional guidewire 1226 has a distal segment that has a smaller diameter than that of the first guidewire 1126 described in FIG. 11C. The distal segment of the transitional guidewire 1226 comprises a soft and atraumatic tip and can be tracked to the remote neurovasculature such as the MCA 1204, which is distal to the petrous segment 1212 of the ICA 1206.

Figure 12E:
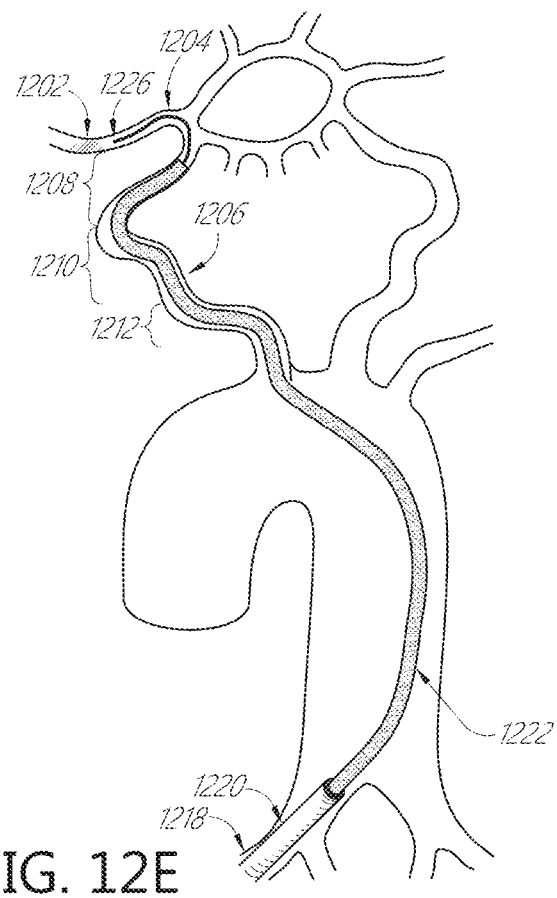

Referring to FIG. 12E, the transitional guide sheath 1222 is advanced to or beyond the cavernous segment 1210 or the cerebral 1208 segment of the ICA 1206. Unlike the guide sheath 1122 described in FIG. 11D, the transitional guide sheath 1222 may be advanced to the cavernous segment 1210 or the cerebral 1208 segment of the ICA 1206 beyond the petrous segment 1212 because the transitional guide sheath 1222 has a soft yet trackable distal segment described in further detail below, for example in connection with FIG. 30. The larger proximal diameter and stiffer body of the transitional guidewire 1226 may provide better support for the transitional guide sheath 1222 to track through the vasculature.

Figure 12F:
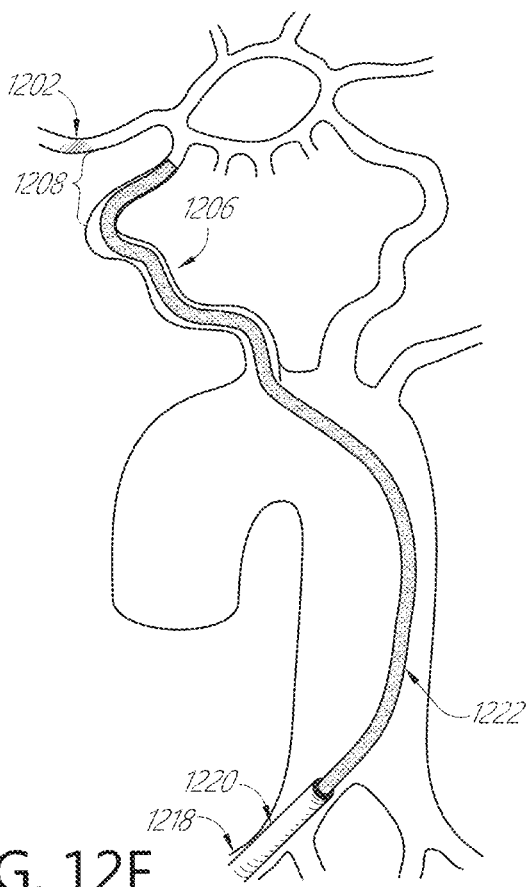

Referring to FIG. 12F, after the transitional guide sheath 1222 is advanced to the cerebral segment 1208 of the ICA 1206, the transitional guidewire 1226 is removed. Then, a vacuum pressure is applied at the proximal end of the transitional guide sheath 1222 to aspirate the clot 1202 through the central lumen of the transitional guide sheath 1222. The inner diameter of the transitional guide sheath 1222 may be equal to about or greater than about 0.100", about 0.088", about 0.080", about 0.070", or about 0.060". The inner diameter of the transitional guide sheath 1222 is larger than the aspiration catheter 1128 described in FIG. 11E, which translates to more effective aspiration. The cross-sectional area of the central lumen of the transitional guide sheath 1222 may be almost twice as large as that of the largest aspiration catheter 1128 currently available.

If the guide sheath 1222 is not able to track deep enough into the distal vasculature to reach the clot or other desired target site, a telescopic extension segment as discussed elsewhere herein may be introduced into the proximal end of sheath 1222 and advanced distally to extend beyond the distal end of the sheath 1222 and thereby extend the reach of the aspiration system. In one implementation of the invention, the extension segment has an ID of about 0.070".

If thrombotic material is not able to be drawn into the sheath 1222 or extension segment under constant vacuum, pulsatile vacuum may be applied as discussed below. If pulsatile vacuum does not satisfactorily capture the clot, an agitator may be advanced through the sheath 1222 and extension segment to facilitate drawing the clot into the central lumen. Additional details of the agitator and its use are disclosed below.

Figure 13:
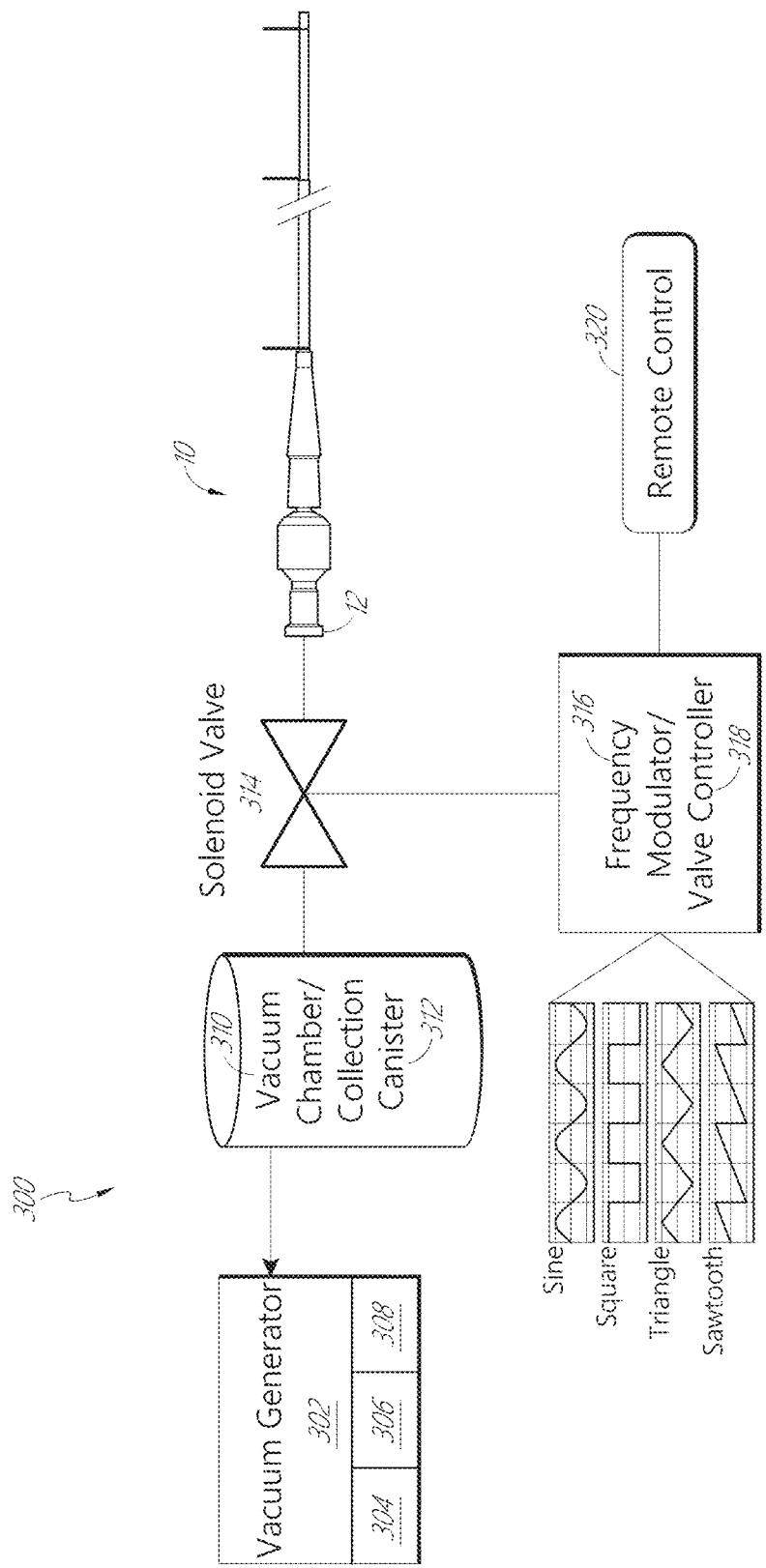
FIG. 13 illustrates an aspiration system configured to apply pulsatile negative pressure through the aspiration catheter.

A pulsatile vacuum pressure aspirator may be used in order to improve effectiveness of aspiration for vascular thrombectomy and to improve catheter trackability through tortuous vasculatures. FIG. 13 shows an embodiment of a pulsatile vacuum pressure aspirator 300 that applies intermittent or pulsatile vacuum to lumen 40. In the illustrated embodiment, the pulsatile vacuum pressure aspirator 300 is in fluid connection with the proximal end 12 of the catheter 10 and comprises vacuum generator 302, vacuum chamber 310, collection canister 312, solenoid valve 314, frequency modulator 316, valve controller 318, and remote controller 320.

Vacuum generator 302 comprises a vacuum pump 304, a vacuum gauge 306, and a pressure adjustment control 308. The vacuum pump 304 generates vacuum. The vacuum gauge 306 is in fluid connection with the vacuum pump 304 and indicates the vacuum pressure generated by the pump 304. The pressure adjustment control 308 allows the user to set to a specific vacuum pressure. Any of a variety of controls may be utilized, including switches, buttons, levers, rotatable knobs, and others which will be apparent to those of skill in the art in view of the disclosure herein.

Vacuum chamber 310 is in fluid connection with the vacuum generator 302 and acts as a pressure reservoir and/or damper. Collection canister 312 is in fluid connection with the vacuum chamber 310 and collects debris. The collection canister 312 may be a removable vial that collects debris or tissues, which may be used for pathologic diagnosis. Vacuum chamber 310 and collection canister 312 may be separate components that are in fluid connection with each other or a merged component. In the illustrated embodiment, the vacuum chamber 310 and the collection canister 312 is a merged component and is in fluid connection with the vacuum generator 302.

Solenoid valve 314 is located in the fluid connection path between a luer or other connector configured to releasably connect to an access port of the catheter 10 and the vacuum chamber 310/collection canister 312. The solenoid valve 314 controls the fluid flow from the catheter 10 to the vacuum chamber 310/collection canister 312.

Pulsatile vacuum pressure aspirator 300 may comprise frequency modulator 316 for control of the solenoid valve 314. The frequency modulator 316 generates different electrical wave frequencies and forms, which are translated into the movement of the solenoid valve 314 by the valve controller 318. The wave forms generated from the frequency modulator 316 comprise sinusoidal, square, and sawtooth waves. The wave forms generated from the frequency modulator 316 typically have frequencies less than about 500 Hz, in some modes of operation less than about 20 Hz or less than about 5 Hz. The wave forms have duty cycles ranging from 0%, in which the solenoid valve 314 is fully shut, to 100%, in which the solenoid valve 314 is fully open.

Valve controller 318 modulates the solenoid valve 314 on and off. The valve controller 318 may be electrically or mechanically connected to the solenoid valve 314. Any of a variety of controls may be utilized, including electrical controllers, switches, buttons, levers, rotatable knobs, and others which will be apparent to those of skill in the art in view of the disclosure herein. The valve controller 318 may be mechanically controlled by users or may be electrically controlled by the frequency modulator 316. The frequency modulator 316 and the valve controller 318 may be separate components that are electrically or mechanically connected or a merged component.

Remote control 320 enables physicians to control the frequency modulator 316 and/or the valve controller 318 for various purposes, such as turning the valve on/off, selecting different wave frequencies, and selecting different wave forms, while manipulating the catheter 10 at the patient side. Remote control 320 may be in wired or wireless communication with aspirator 300.

By tuning frequency, duty cycle, and wave form, one skilled in the art may match or approximate the resonating frequency to the natural frequency of the catheter. This may further enhance the efficacy of aspiration. The natural frequency of the catheter is typically less than about 260 Hz.

Figure 14:
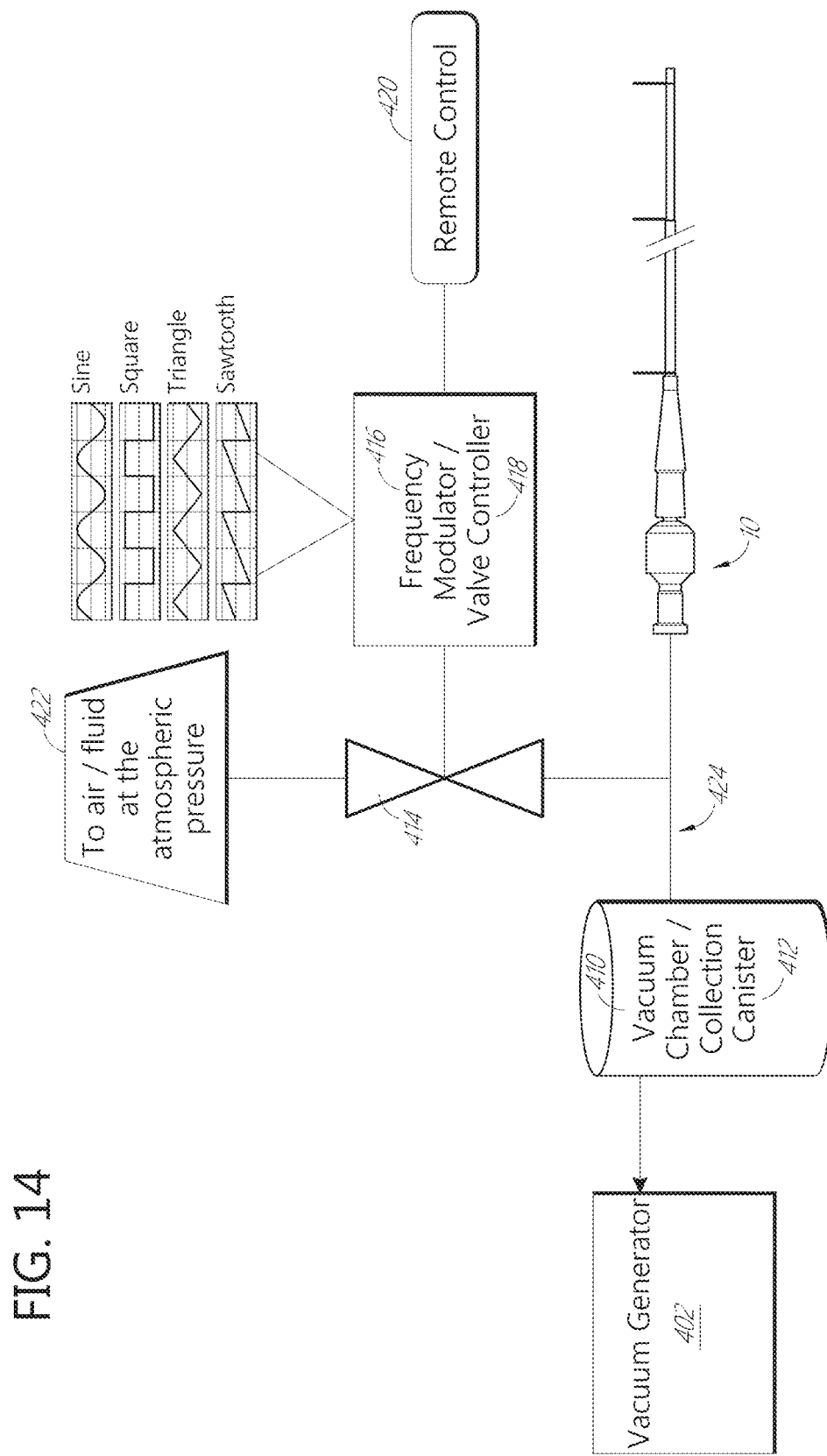
FIG. 14 illustrates an alternative aspiration system configured to apply pulsatile negative pressure through the aspiration catheter.

In another embodiment, shown in FIG. 14, an alternative aspiration system may comprises a vacuum generator 402, a frequency modulator 416, a valve controller 418, and a remote controller 420. In this embodiment, the solenoid valve 414 is positioned in and fluidly connects between the air/fluid reservoir 422 at the atmospheric pressure and the aspiration line 424 connecting the catheter 10 to the vacuum chamber 410/collection canister 412. Unlike the first embodiment in FIG. 13, this system modulates pressure in the catheter 10 by allowing pressure to vary from vacuum to atmospheric pressure. When the solenoid valve 414 is open to the air/fluid reservoir 422 at the atmospheric pressure, the vacuum pressure in the aspiration line 424 decreases to the atmospheric pressure. When the solenoid valve 414 is closed, it increases the vacuum pressure in the aspiration line 424.

Figure 15:
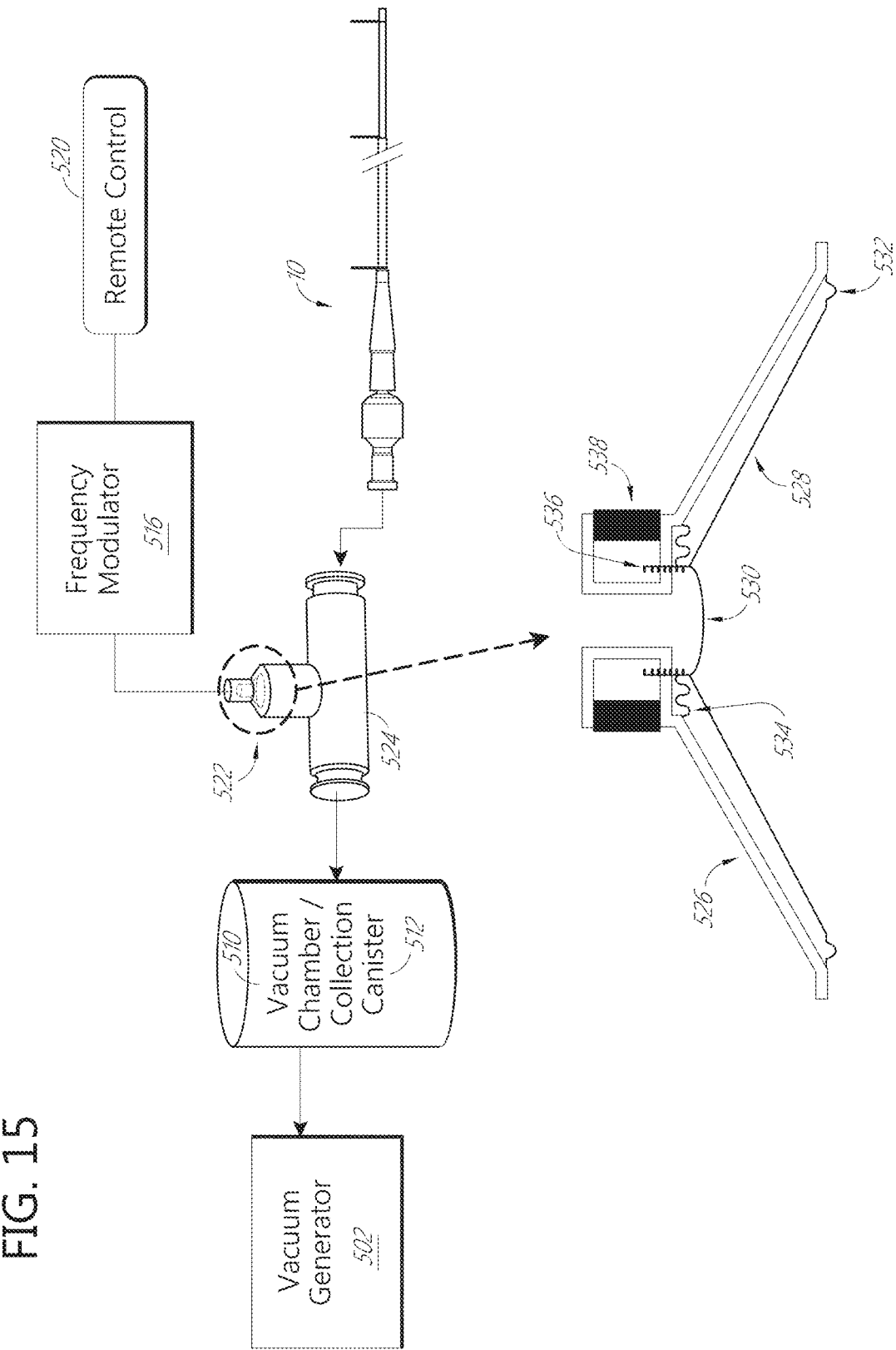
FIG. 15 illustrates a further alternative aspiration system configured to apply mechanical vibration through the aspiration catheter.

In yet another embodiment, shown in FIG. 15, an electromagnetic actuated diaphragm 522 is attached to the aspiration line 524 connecting the catheter 10 to the vacuum chamber 510/collection canister 512. The electromagnetic actuated diaphragm 522, which is similar to that of a speaker driver, generates acoustic pressure waves in the catheter 10. The diaphragm 522 typically has a structure similar to a speaker driver and comprises frame 526, cone 528, dust cap 530, surround 532, spider or damper 534, voice coil 536 and magnet 538. Strength of the acoustic pressure waves may be modulated by the strength of the magnet 538. The frequency modulator 516 connected to the remote control 520 is electrically connected to the diaphragm 522 and generates different electrical wave frequencies and forms, which are translated by the diaphragm 522 into acoustic pressure waves in the aspiration line 524 and the catheter 10.

Tortuous vasculature is a common reason for failure to treat vasculature occlusions in the body due to inability to track the catheter to the location of the disease. Navigating catheters through tortuous anatomy such as neurovasculature can be a challenge. The catheter has to be very soft as not to damage the vessel wall. At the same time, it also has to be able to negotiate multiple tight turns without kinking. In addition, it has to have sufficient column strength to transmit force axially for advancing through the vasculature. All these performance characteristics are competing design requirements. It is difficult to optimize one performance characteristic without sacrificing the others.

Reducing friction between the inner diameter of the vessel and the outer diameter of the catheter can minimize axial force required to advance catheter through tortuous vasculature. Therefore, the column strength of the catheter may be traded off for optimizing other performance requirements of the catheter. An example of a method to reduce friction between the inner diameter of the blood vessel and the outer diameter of the catheter is to apply a thin layer of coating, usually hydrophilic in nature, to the outer diameter of the catheter to reduce its surface friction coefficient while in vivo.

In addition or as an alternative to the water hammer construction discussed above, axial mechanical vibration or shock waves may be propagated to or generated at the distal end of the catheter using a variety of vibration generators, such as spark gap generators, piezoelectric pulse generators, electric solenoids, rotational shaft (wire) having one or more bends or carrying an eccentric weight, or any of a variety of other impulse generating sources well understood for example in the lithotripsy arts. Mechanical shock wave or pulse generators may be built into the proximal manifold 18, and or mechanically coupled to the manifold or proximal catheter shaft as desired. Preferably, controls are provided on the manifold or on a proximal control coupled to the manifold, to enable the clinician to vary the intensity and time parameters of the mechanical pulses. Shock waves may be propagated along the proximal section 33 to assist in translumenal advance, and/or distal section 34 by way of pull wire 42, depending upon the desired clinical performance.

Figure 16:
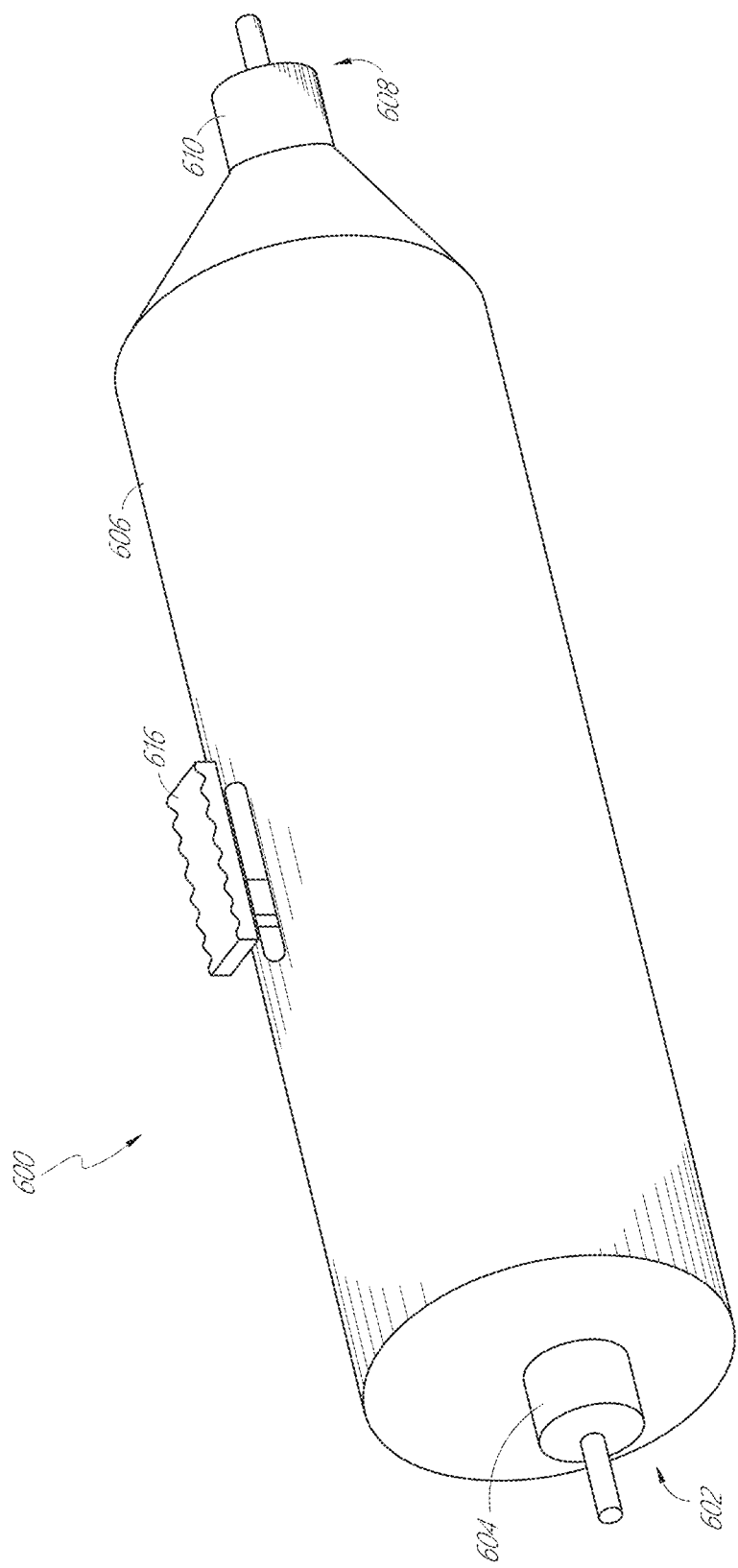
FIGS. 16 and 17 illustrate a further alternative aspiration system configured to apply mechanical vibration through the aspiration catheter.
Figure 17:
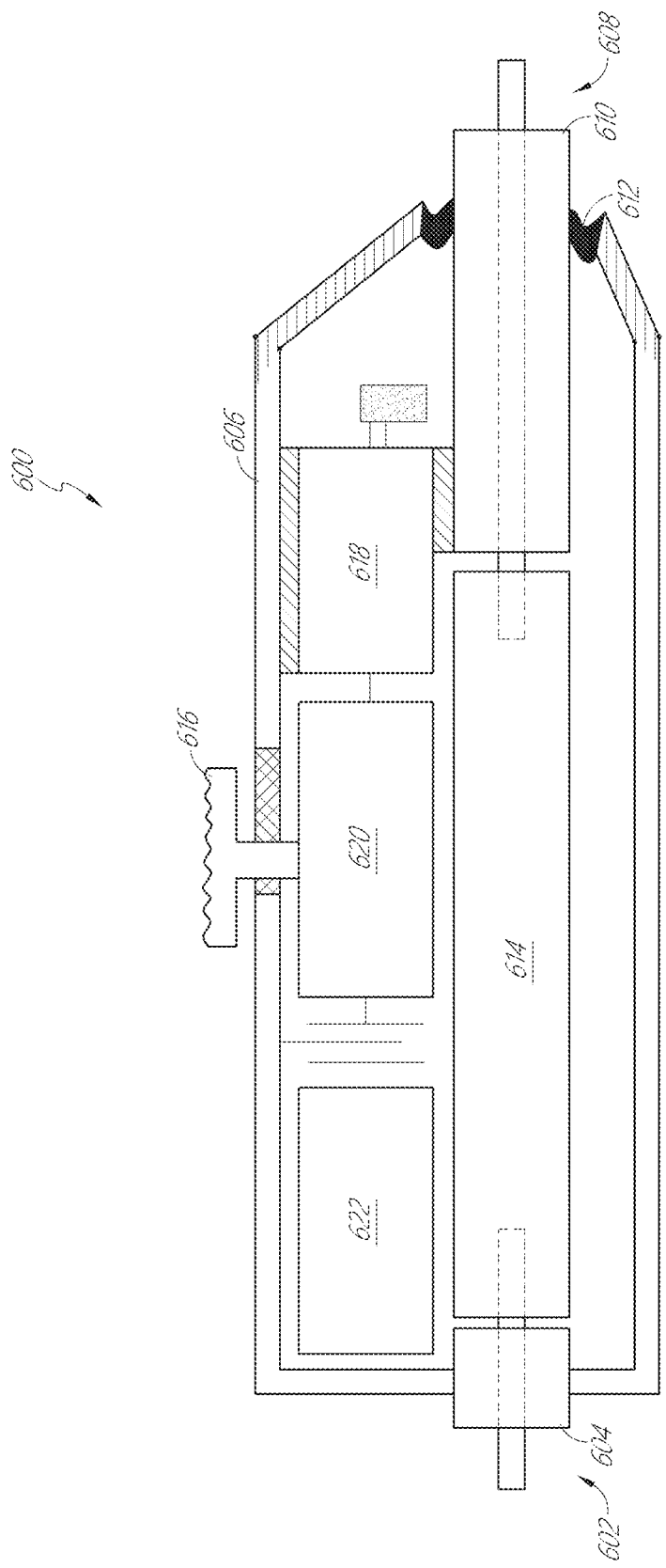

In an embodiment shown in FIGS. 16 and 17, the distal end 608 of a vibrating device 600 is placed in fluid connection with the proximal end 12 of the catheter 10 (not illustrated) and generates transverse and/or longitudinal vibration in the catheter 10. By inducing transverse vibration in the catheter 10, it reduces effective contact surface area between the vessel and the catheter 10, which in turn reduces surface friction force between the inner diameter of the vessel and the outer diameter of the catheter. In addition, by inducing longitudinal vibration in the catheter 10, the vibrating device 600 breaks static friction between the inner diameter of the vessel and the outer diameter of the catheter 10, which reduces overall surface friction. By reducing the friction between the inner diameter of the vessel and the outer diameter of the catheter 10, the vibrating device 600 improves catheter trackability through tortuous vasculatures.

In the illustrated embodiment, the proximal end 602 of the vibrating device 600 may be connected to a vacuum pressure source such as a vacuum generator. The proximal connector 604 is attached to the housing 606. In at least one embodiment, the proximal connector 604 may be a luer connector. The distal end 608 of the vibrating device 600 is connected to the catheter 10. The distal connector 610 is held in place by a flexible seal 612 that is attached to the housing 606. In at least one embodiment, the distal connector 610 may be a luer connector. The flexible seal 612 allows the distal connector 610 to move longitudinally as well as transversely. The flexible tubing links the proximal connector 604 and the distal connector 610, creating an aspiration channel 614 for the fluid to travel through.

The vibrating device has a controller 616 to turn on/off the vibrating action as well as to vary its frequency. In this embodiment, the controller 616 is drawn as a sliding switch. Any of a variety of controls may be utilized, including electrical controllers, switches, buttons, levers, rotatable knobs, and others which will be apparent to those of skill in the art in view of the disclosure herein.

A vibration generator such as a motor 618 has an eccentrically mounted inertial weight on its shaft generating vibration. Any of a variety of motors may be used, including an electric motor, an electro-magnetic actuator, and a piezoelectric transducer. The frequency of the vibration is related to the RPM of the motor 618. A driving circuit 620 is connected to the motor 618 and the controller 616 and drives the motor 618 at different RPMs based on the manipulation of the controller 616. In the illustrated embodiment, the circuit 620 drives the motor 618 at different RPMs based on the position of the sliding switch. A battery 622 is connected to and powers the driving circuit 620 and the motor 618.

The motor 618 may be mounted perpendicularly to the length of the aspiration channel 614 to create longitudinal vibration. Also, a mechanical cam may be attached to the motor 618 to create larger magnitude longitudinal reciprocating motion. The frequency range generated by the electric motor is typically less than about 85 Hz. To achieve sonic frequencies in the range from about 85 Hz to about 260 Hz, one might replace the electric motor with an electro-magnetic actuator. To achieve ultrasonic frequencies in the range of about 20 Hz to about 1.6 MHz, one might employ a piezoelectric transducer.

Figure 18:
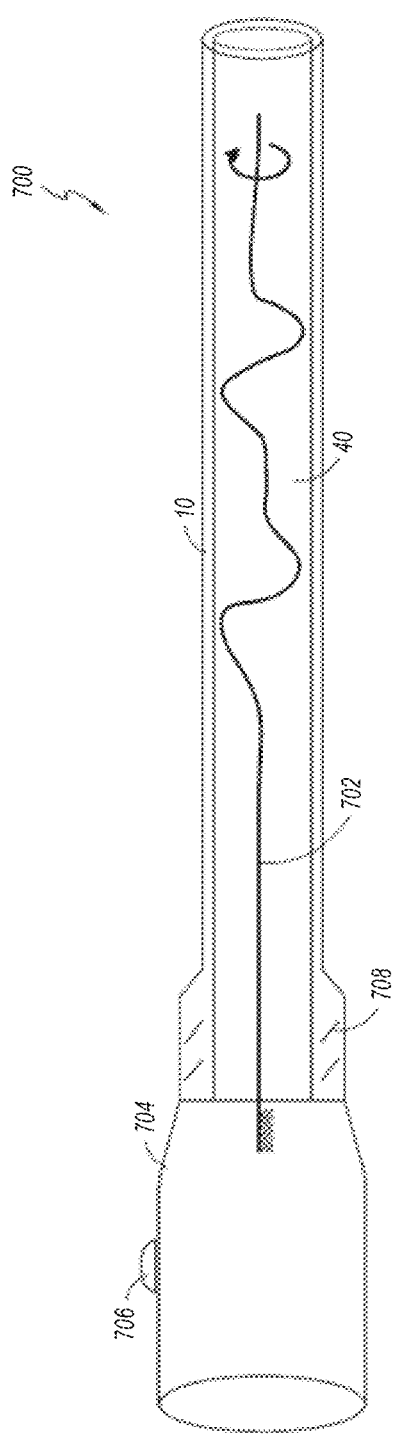
FIG. 18 illustrates a further alternative aspiration system having an agitator configured to apply mechanical vibration at a vibration zone on the aspiration catheter.

In yet another embodiment, shown in FIG. 18, an agitator such as stylet 702 is permanently or removably inserted into a lumen 40 of the catheter 10 and rotated to generate vibration in the catheter 10 and thus improve catheter trackability through tortuous vasculatures. The stylet 702, whose outer diameter is within the range of from about 0.005 inches (about 0.127 mm) to about 0.035 inches (about 0.889 mm), may have at least one bend or at least one weight. The peak to peak transverse distance between the bends will be less than the inner diameter of the catheter 10 when positioned within the catheter. The bends or weights of the stylet 702 may be positioned at different locations along the entire length of the catheter 10 or contained within a vibration zone within the distal most 50% or 30% or 10% of the length of the catheter depending upon desired performance, with the purpose to create the most desirable vibration when tracking the catheter 10 through the distal vasculature.

Alternatively, the stylet 702 may have an asymmetric weight such as a bead at a distal vibration zone or at its distal end. The stylet 702 may comprise a monofilament or braided or woven filaments or wires.

In another alternative, the stylet 702 may have a heater (e.g., an electric coil) at its distal end that facilitates the dissolution of the thrombus or changes the size of the thrombus that is aspirated into the catheter.

The proximal end of the stylet is attached to a motor driver 704 capable of generating rotational and or axially reciprocating motion at various frequencies to form a motor driver-stylet assembly 700. The assembly 700 has a controller 706 to turn on/off the rotating action as well as to vary its frequency. In this embodiment, the controller 706 is drawn as an on/off button. Any of a variety of controls may be utilized, including electrical controllers, switches, buttons, levers, rotatable knobs, and others which will be apparent to those of skill in the art in view of the disclosure herein. The proximal luer 708 or other connector of the catheter 10 reversibly attaches the catheter 10 to the motor driver 804.

Once the catheter 10 has reached its intended location, the entire motor driver-stylet assembly 700 may be detached and removed from the catheter 10 leaving a central aspiration lumen.

In patients with vertebral artery occlusions, treatment with angioplasty can result in complications due to embolization of the occlusive lesion downstream to the basilar artery. Emboli small enough to pass through the vertebral arteries into the larger basilar artery are usually arrested at the top of the basilar artery, where it bifurcates into the posterior cerebral arteries. The resulting reduction in blood flow to the ascending reticular formation of the midbrain and thalamus produces immediate loss of consciousness. The devices described herein can be used to remove thromboembolic material from the vertebral artery or more distally such as in M1, M2, or M3 arteries.

Figure 19:
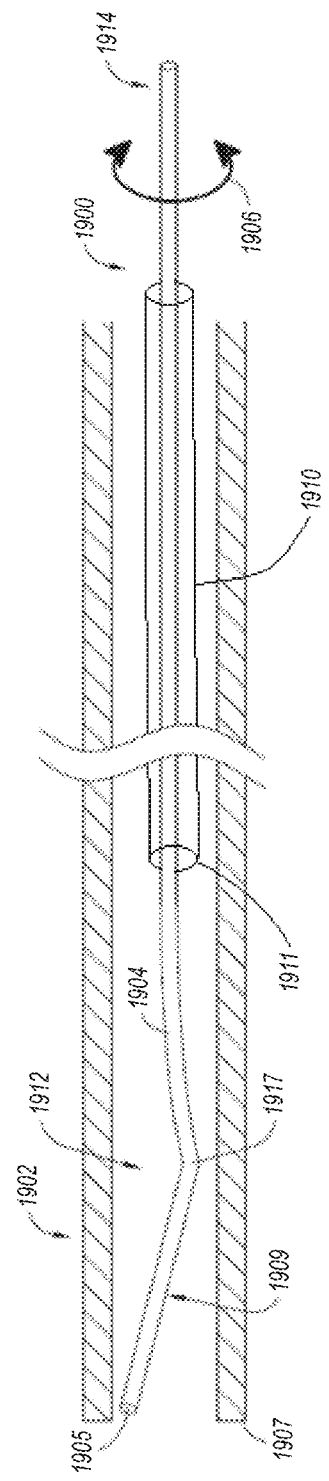
FIG. 19 depicts a simplified agitator such as a hypo tube supported wire placed in a catheter to create a vibration zone.

Agitators for providing vibratory assistance for navigation and/or assisting in the capture and aspiration of debris are described further in connection with FIGS. 19-24. Referring to FIG. 19, an agitator 1900 may comprise an elongate, flexible body such as a wire or hypo tube having a proximal, control end and a distal, active zone or end. The hypo tube agitator has an inside lumen extending longitudinally that allows infusion of media. Referring to FIG. 19, an agitator 1900 comprises a wire or hypo tube 1904, introduced into the proximal end of a catheter 1902 and advanced to the distal end 1907 of the catheter 1902. The distal tip 1905 of the agitator 1900 may be placed at, beyond, or inside the distal end of the catheter 1902. The agitator 1900 can be either preloaded into the catheter 1902 and inserted into the patient's body together with the catheter 1902 or added after the catheter 1902 has been placed. When loaded inside the catheter 1902, the agitator 1900 may extend substantially longitudinally along the length of the catheter 1902. The agitator 1900 may further comprise a controller at the proximal end to axially adjust the distal tip position. The controller of the agitator 1900 may be used to axially adjust the position of the distal tip 1905 when the agitator 1900 is introduced into a variable length catheter such as that discussed in connection with FIG. 3.

In one implementation of the invention, the agitator and drive system are configured as a stand-alone device. Once the distal section 34 (FIG. 3B) has been positioned within a few (e.g., no more than about 3 or 2) centimeters of the obstruction, the distal end of agitator 1900 may be introduced into the proximal end of central lumen 45 of pull wire 42. Agitator 1900 may thereafter be distally advanced so that a distal segment of agitator 1900 extends beyond the distal end of pull wire 42, and into the distal section 34. The portion of the agitator 1900 contained within lumen 45 of pull wire 42 is restrained from any significant lateral motion. However, the distal portion of agitator 1900 which extends beyond the distal end of pull wire 42 is relatively laterally unconstrained and is able to agitate thrombus to facilitate drawing the thrombus into and through the distal section 34. Once the thrombus has been drawn proximally under vacuum and with activation of the agitator as needed, to reach the step up in ID at the proximal end of distal section 34, the risk of clogging is greatly reduced.

The agitator 1900 may be rotated manually or via a motor 1906 driven from the catheter 1902's proximal end to rotate or translate the distal end of the agitator 1900. The driver 1906 may be connected to the proximal end of the agitator 1900 either permanently or removably. The driver 1906 may be a manual driver that is manually controlled such as a guidewire torquer. The driver 1906 may be a motorized driver. The motorized driver may be manually controlled with respect to one or more factors such as rotational direction (CCW/CW), speed, duration, etc. The motorized driver may be automatically controlled with respect to one or more factors such as direction (CCW/CW), speed, duration, etc. In one mode, the rotational direction of the agitator is periodically reversed.

The automatically controlled driver may comprise an actuator, and actuating the actuator may execute a pre-programmed series of steps. The actuator may be a button, a dial, a knob, a switch, a lever, a valve, a slide, a keypad, or any combinations thereof. The driver 1906 may also be under synchronized control, in which the driver 1906 drives the agitator 1900 in synchronization with aspiration and media injection. The agitator 1900 may be configured to promote motion at the distal end to help engage and move the clot.

Media may be infused into/around the clot area to help liberate the clot from the vasculature.

The agitator 1900 comprises a distal end 1912, a proximal end 1914 and a distal tip 1905. The proximal end 1914 of the agitator 1900 has a cross-section and/or wall thickness that is large enough to transmit the torque required to rotate the distal end 1912 of the agitator 1900 when placed in the catheter 1902, within the curved vasculature. The outer diameter of the agitator 1900 may be from about 0.25 mm to about 0.65 mm, from about 0.3 mm to about 0.6 mm, from about 0.35 mm to about 0.55 mm, from about 0.4 mm to about 0.5 mm, from about 0.42 mm to about 0.48 mm, or from about 0.44 mm to about 0.46 mm. In case of the hypo tube 1904, the wall thickness of the hypo tube 1904 may be from about 0.01 mm to about 0.29 mm, from about 0.05 mm to about 0.25 mm, from about 0.1 mm to about 0.2 mm, from about 0.12 mm to about 0.18 mm, from about 0.13 mm to about 0.17 mm, or from about 0.14 mm to about 0.16 mm.

The agitator 1900 may additionally be provided with a guide tube 1910, such as a hypo tube, to allow the agitator to spin, or axially or rotationally reciprocate, while constraining a proximal drive segment of the agitator 1900 against lateral motion. A distal end 1911 of guide tube 1910 may be positioned within about 25 cm or within about 20 cm or 15 cm or less of the distal end of the agitator 1900, depending upon desired performance. The distal section of the agitator 1900, extending beyond distal end 1911 of guide tube 1910, is laterally unconstrained within the ID of distal segment 34 and available to agitate and facilitate aspiration of material into and through the central lumen.

The diameter of the agitator 1900 may be constant along its longitudinal length. The diameter of the agitator 1900 may increase or decrease along its longitudinal length to coincide with features of the catheter 1902. In one implementation, the diameter of the agitator 1900 decreases in the distal direction along its longitudinal length by at least one step or tapered zone to provide increasing flexibility.

Figure 20D:
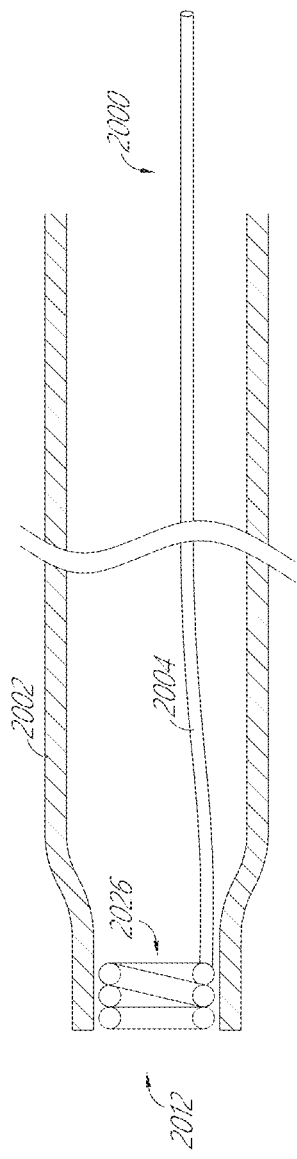
FIGS. 20D-20E depict an agitator positioned within a swellable polymer distal funnel tip.
Figure 20E:
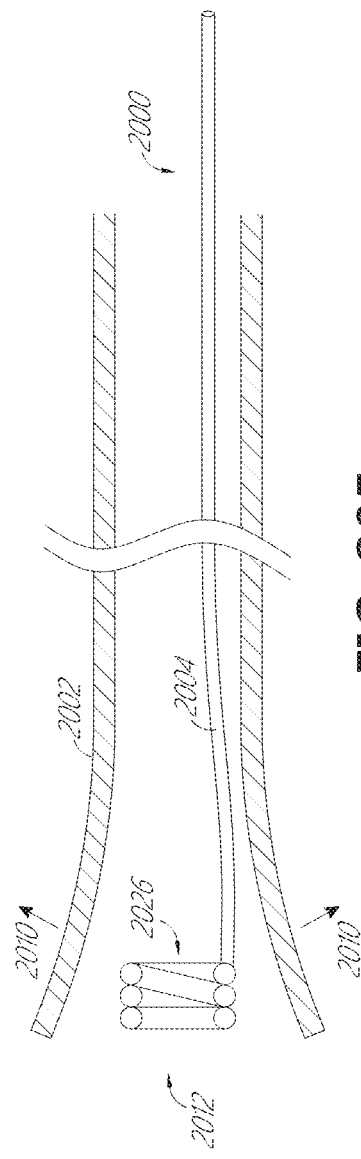

The distal end 1912 of the agitator 1900 may be straight. Alternatively, the distal end 1912 of the agitator 1900 may be curved or formed into different shapes to interact with the clot. FIG. 19 illustrates a bend 1917 spaced apart from the distal tip 1905 by a motion segment 1909 having a length of from about 1 mm to about 15 mm. FIGS. 20A-20C depict more complex exemplary shapes of the motion segment 1909 of the agitator 1900. FIGS. 20D-20E depict an agitator positioned within a swellable polymer distal funnel tip.

The agitator 1900 may be comprise a single, uniform material or multiple materials. The materials of the agitator 1900 may be processed (e.g., heat treatment/annealing) to give varying properties for the local performance requirements. The agitator 1900 may be structured to provide flexibility while exhibiting high torque transmission. The agitator 1900 may made of Nitinol, 304 Stainless Steel, 316 LVM Stainless Steel, PTFE, Parylene, or any combinations thereof. At least a portion of the surface of the agitator 1900 may be coated. The entire length of the agitator 1900 may be coated. The coating on the agitator 1900 may provide lubrication between the ID wall of the catheter 1902 and the agitator 1900. In a case that an intermediate hypotube is placed between the wall of the catheter 1902 and the agitator 1900, e.g., constraining tube 1910 or tubular pull wire 42, the coating on the agitator 1900 may provide lubrication between the intermediate hypotube and the proximal drive portion of the agitator 1900. The coating materials of the wire or hypo tube 1904 include PTFE, Parylene, Teflon, or any combinations thereof.

Any of the ID or OD of any of the catheter shafts or other catheter components disclosed herein may be provided with a lubricious coating or may be made from a lubricious material. For example, a hydrophilic polymer such as Poly-acrylamide, PEO, thermoplastic starch, PVP, copolymers of hydrophilic polymer can be extruded with hydrophobic polymers such as PEO soft segmented polyurethane blended with Tecoflex. The lubricious coating or the lubricious material may include surface modifying additive (SMA) during melt processing. The lubricious coating or the lubricious material contributes to at least ease of navigation, lower ID skin friction, or better clot removal. In some embodiments, post processing wire ebeam, Gamma, UV, etc. additionally may be desirable to expose to moisture, temperature, etc. Catheters may be made from PEO impregnated polyurethanes such as Hydrothane, Tecophilic polyurethane for both OD and ID lubricity and inherent thromboresistant property without requiring a secondary coating process.

Referring to FIG. 20A, an agitator 1900 comprises a wire or hypo tube 2004, as illustrated in the figure, and the distal end 2012 of the agitator 1900 may comprise a coil 2020 to grip a corked clot and wiggle the distal end 2010 of the catheter 2002 and the clot during rotation 2006. The coil 2020 may be a tight, offset coil, and may comprise at least one and optionally two or three or more complete revolutions.

Referring to FIG. 20B, the distal end 2012 of the agitator 1900 may comprise a hook 2022 to grip and emulsify a clot. The hook 2022 may be concave proximally, or may extend transversely to the axis of the agitator body, extending in a circumferential orientation. Referring to FIG. 20C, the distal end 2012 of the agitator 1900 may comprise a loose coil or spring 2024. The loose coil or spring 2024 may expand (lengthen) and contract (shorten) with a change in direction of rotation.

Referring to FIGS. 20D-20E, the distal end 2012 of the agitator 2000 may comprise a coil 2026 to grip a corked clot and wiggle the distal end 2010 of the catheter 2002 and the clot during rotation. In addition, the distal end 2010 of the catheter 2002 may include a polymer sidewall that reforms by hydration. The coil 2026 maintains a guide wire lumen during placement of the catheter. The polymer enables the distal end 2010 of the catheter 2002 to expand to a funnel shape after absorption of serum from blood. See FIG. 20E.

Referring to FIGS. 21A-21B, the distal tip 2110 of the catheter 2102 may move or wiggle by interacting with the agitator 1900. As illustrated in the figures, the agitator 1900 comprises a wire or hypo tube 2104. When the distal end of the agitator 1900 rotates (e.g., via a driver 2106), the motion segment 1909 and distal tip 1905 of the agitator interact with the side wall of the catheter 2102 which wiggles as shown by broken lines 2112. The length of the motion segment, stiffness of the agitator 1900 and rotational velocity determines the interaction with the wall of the catheter 2102 and the amount of wiggle transmitted to the catheter 2101 with rotation of the agitator 1900.

Alternatively, the distal tip 2110 of the catheter 2102 may move or wiggle by pulsed media jets existing one or more holes near the distal end of the hypo tube 2124. The hypo tube 2124 has an inside lumen extending along the longitudinal length of the hypo tube 2124. One or more side holes 2128 may be placed near the distal end of the hypo tube 2124 and allow fluid communication between the lumen of the hypo tube 2124 and the outside of the hypo tube 2124 (i.e., the lumen of the catheter 2102). Media (e.g. saline) may be introduced under pressure into the proximal end of the hypo tube 2124, through the lumen of the hypo tube 2124, and then through the one or more holes of the hypo tube 2124. When media is injected into the hypo tube 2124 in a pulsed manner, pulsed media jets eject from the holes of the hypo tube 2124 and transmit forces on the wall of the catheter 2102, resulting in a wiggle motion of the catheter 2102. The hypo tube 2124 may additionally rotate (e.g., via a driver 2106) to facilitate a wiggle motion of the catheter 2102.

Referring to FIGS. 22A-22B, the hypo tube 2204 may have one or more holes 2210 and is bent near its distal portion to provide a motion segment 1909. Media (e.g. saline, a drug, a lubricant such as polyethylene glycol) is injected from the proximal end 2200, through the inside lumen, and out of the holes 2210 of the hypo tube 2204 (direction of media ejection shown as 2208). Vacuum is applied to the central lumen at the proximal end 2200 of the catheter 2202 such that media ejecting from the holes 2210 of the hypo tube 2204 is drawn proximally along the central lumen of the catheter 2202 toward its proximal end 2200.

As the hypo tube 2204 rotates, the hypo tube 2204 ejects media and simultaneously makes the distal tip of the catheter 2202 wriggle. When the distal tip of the catheter 2202 wriggles by the rotation of the hypo tube 2204, the wriggle of the catheter 2202 may push the clot 2214 from side to side, and the hypo tube 2204 simultaneously ejects media at the interface between the clot 2214 and the catheter 2202, providing a lubricious avenue for the clot 2214 to release and flow into the catheter 2202.

With or without injection of media, rotation of the motion segment 1909 helps to break up or reshape the thrombus and facilitate entry into the aspiration lumen. In certain situations, the clot can be aspirated completely within the central lumen. In other situations, the clot may only be able to be partially drawn into the central lumen, such as illustrated in FIG. 22B. In this situation, rotation of the agitator may be stopped with application of vacuum remaining on to retain the clot on the distal end of the catheter. The catheter may then be proximally withdrawn, pulling the clot along with it, into the access sheath and out of the proximal vascular access point.

Figure 23A:
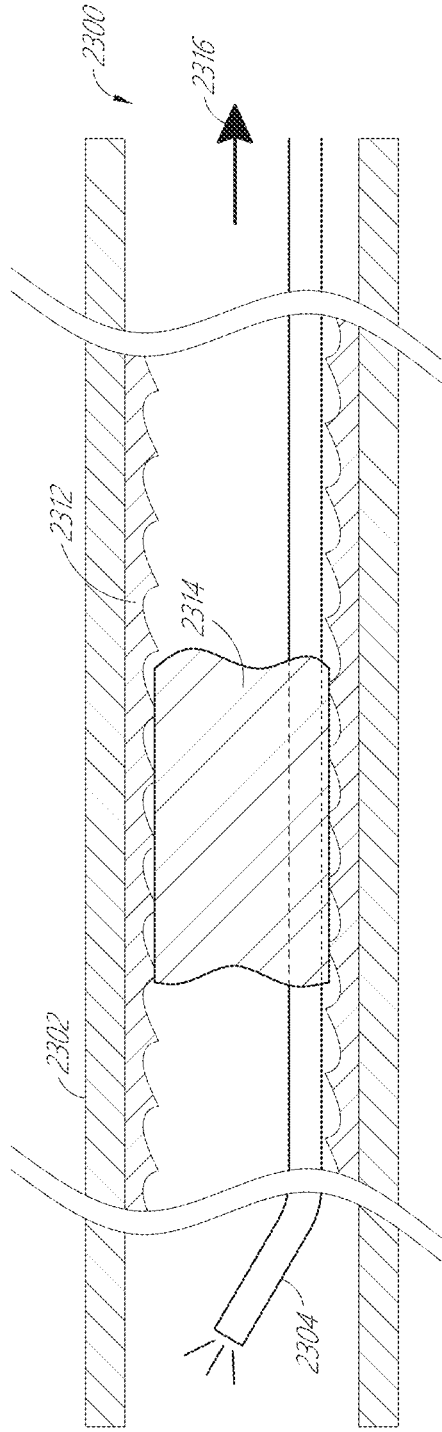
FIGS. 23A-23B illustrate media injection from a distal tip of an agitator to assist aspiration.
Figure 23B:
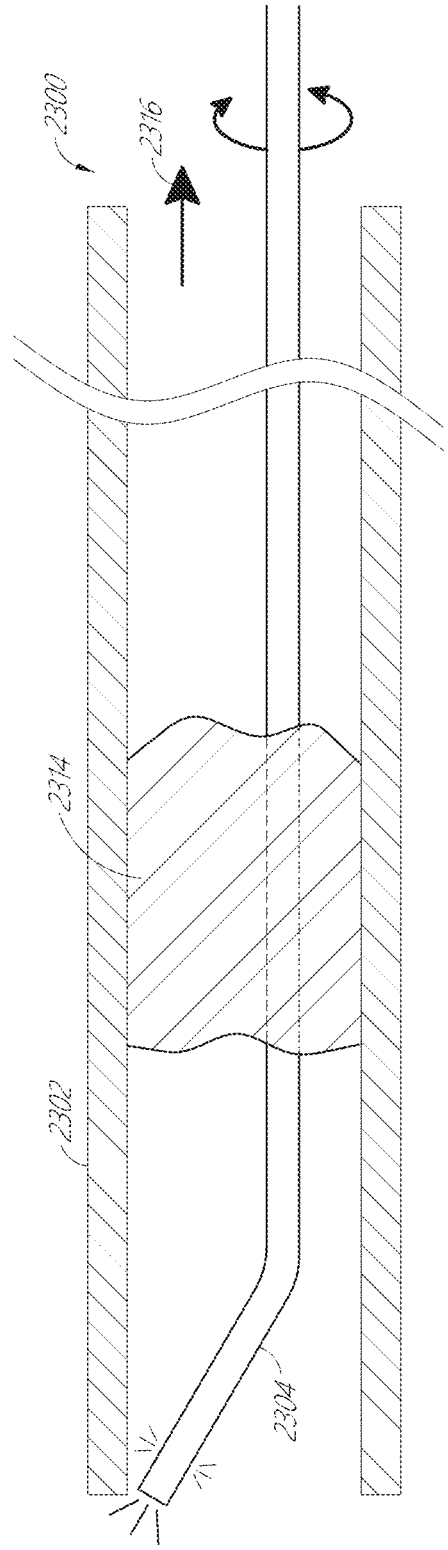

Referring to FIGS. 23A-23B, the hypo tube 2304 may have one or more holes along its surface more proximal from the distal end to facilitate the movement or flow of the clot 2314 inside the catheter 2302 toward its proximal end 2300. Vacuum 2316 is applied at the proximal end 2300 of the catheter 2302 to move the removed clot 2314 from the distal end to the proximal end 2300 of the catheter 2302. As shown in FIG. 23A, the holes may provide a thin film 2312 around the inside of the wall of the catheter 2302 to facilitate the flow of media and/or the clot 2314 and minimize any clogging of the clot 2314. As shown in FIG. 23B, the hypo tube 2304 may have one or more holes to provide media jets ejecting radially from the hypo tube 2304 to grab, pull, and/or emulsify the clot 2314 as the clot 2314 passes by the one or more holes on the surface of the hypo tube 2304.

Figure 24:
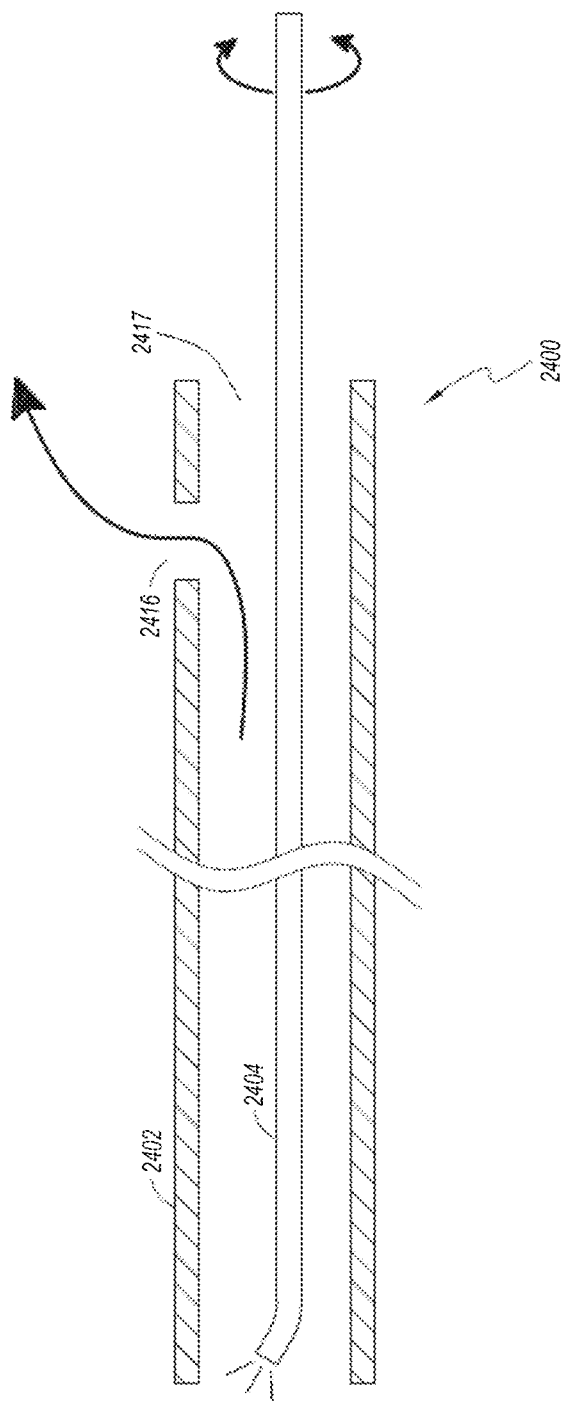
FIG. 24 depicts a proximal aspiration port carried by a catheter.

Referring to FIG. 24, a vacuum port 2416 may be provided near the proximal end 2400 of the catheter 2402 such as on the manifold for releasable connection to a vacuum source to aspirate the clot from the vasculature. This allows the vacuum port 2416 to be distinct from the proximal port 2417 for receiving the agitator 1900. This can minimize the risk that the movement or control of the wire or hypo tube 2404 at its proximal end may be adversely affected by vacuum, aspirated clot, and/or media. The vacuum port may be connected to the catheter 2400 via a rotating hemostasis valve, discussed below.

Figure 25A:
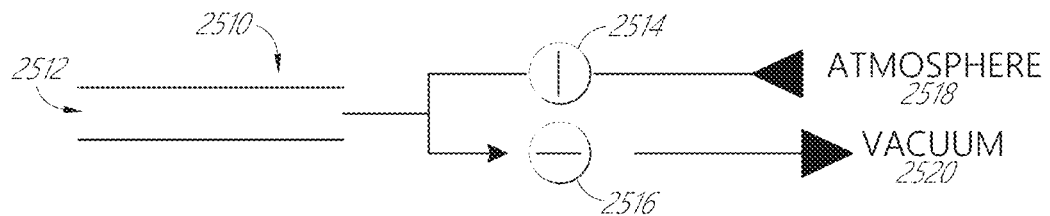
FIGS. 25A-25C depict a pulsed aspiration cycle according to an embodiment.
Figure 25B:
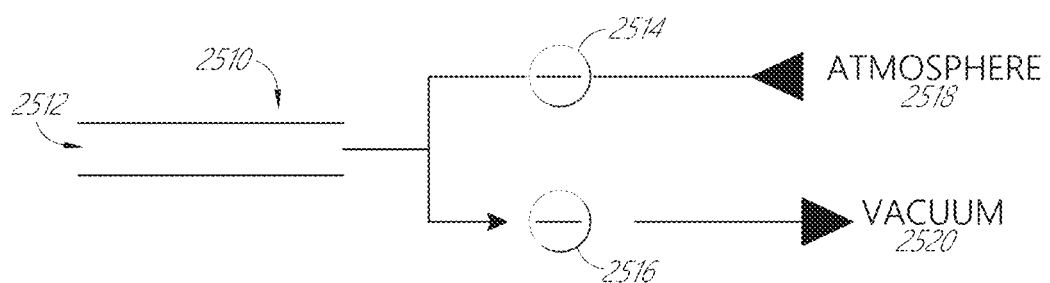
Figure 25C:
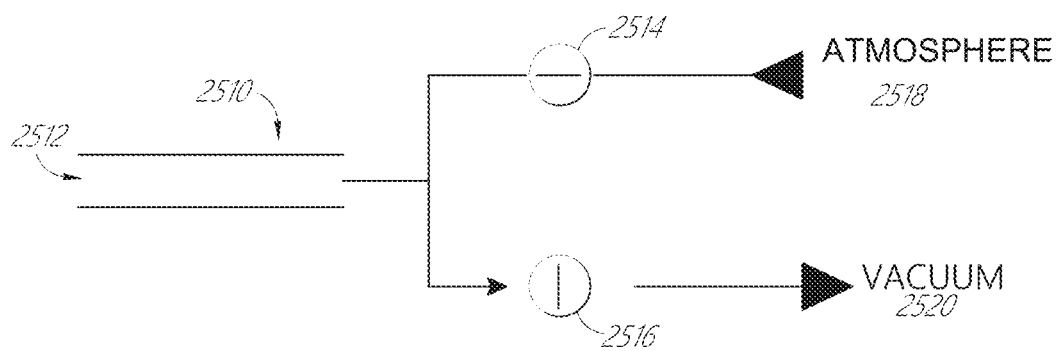

Referring to FIGS. 25A-25C, experiments showed that an interrupted vacuum can help aspirating a corked clot stuck at the distal end 2512 of the catheter 2510 by loosening the clot and reshaping it to fit into the catheter 2510 after each vacuum and release cycle. Merely stopping the vacuum is not sufficient to loosen the clot. Completely releasing (venting to atmospheric pressure) the vacuum and allowing the clot to relax before reapplying a vacuum is found to aspirate the corked clot most efficiently. The period of each vacuum and release cycle may be equal to or greater than about 0.1, 0.5, 1, 2, 3, 4, 5, 6, 7, 8, 9, or 10 seconds.

FIGS. 25A-25C show a logical progression of the vacuum and release cycle as applied to the catheter 2510. A release line 2518 and a vacuum line 2520 are connected to or near the proximal end of the catheter 2510. The release line 2518 is in communication with atmospheric pressure on its proximal end and has a release valve 2514 configured to open or close the fluid communication between the catheter 2510 and the vacuum. The vacuum line 2520 is connected to vacuum on its proximal end and has a vacuum valve 2516 configured to open or close the fluid communication between the catheter 2510 and the vacuum.

In the first step as shown in FIG. 25A, the release valve 2514 is closed, and the vacuum valve 2516 is open such that the vacuum is applied to the catheter 2510 to aspirate the clot. Then, as shown in FIG. 25B, the release valve 2514 is opened while the vacuum valve 2516 stays open. Because the release line 2518 and the vacuum line 2520 are in fluid communication, either directly or via at least a portion of the catheter 2510, the vacuum is applied mainly through the release line 2518, dropping vacuum applied to the catheter. Finally, as shown in FIG. 25C, the vacuum valve 2516 is shut off, allowing the vacuum to be completely released and the clot to relax. Then, another cycle from FIG. 25A to FIG. 25C begins by closing the release valve 2514 and opening the vacuum valve 2516.

Figure 26:
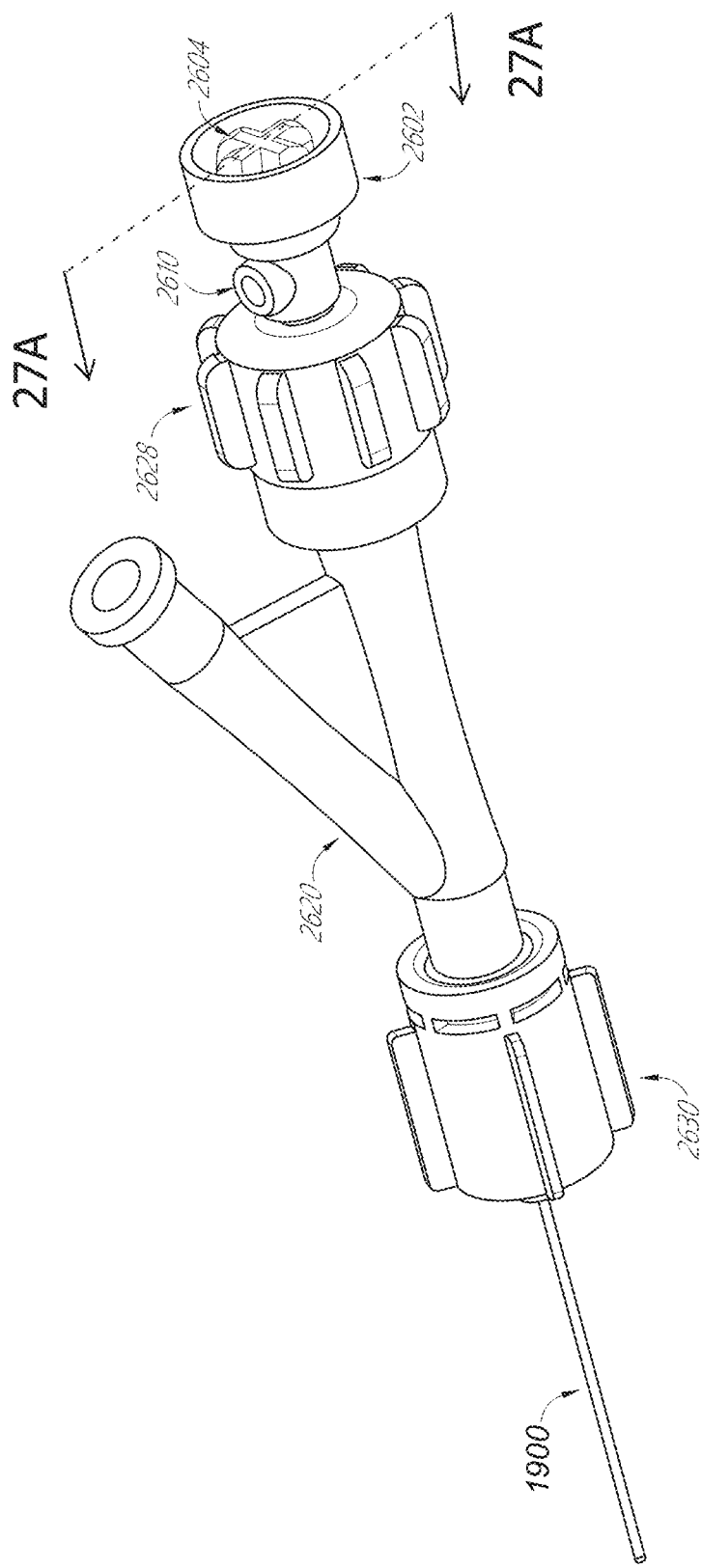
FIG. 26 depicts a perspective view of a rotating hemostasis valve and a proximal drive assembly.
Figure 27A:
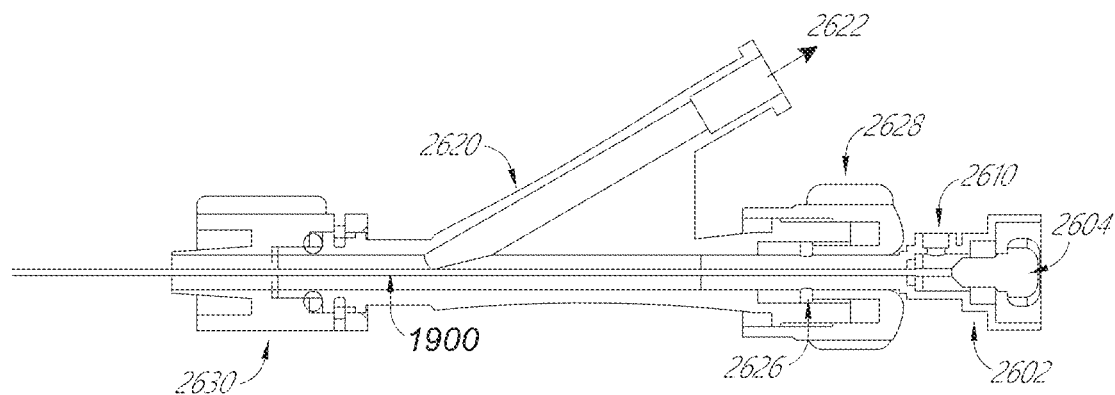
FIG. 27A illustrates a longitudinal cross-sectional elevational view taken along the line 27A-27A in FIG. 26.
Figure 27B:
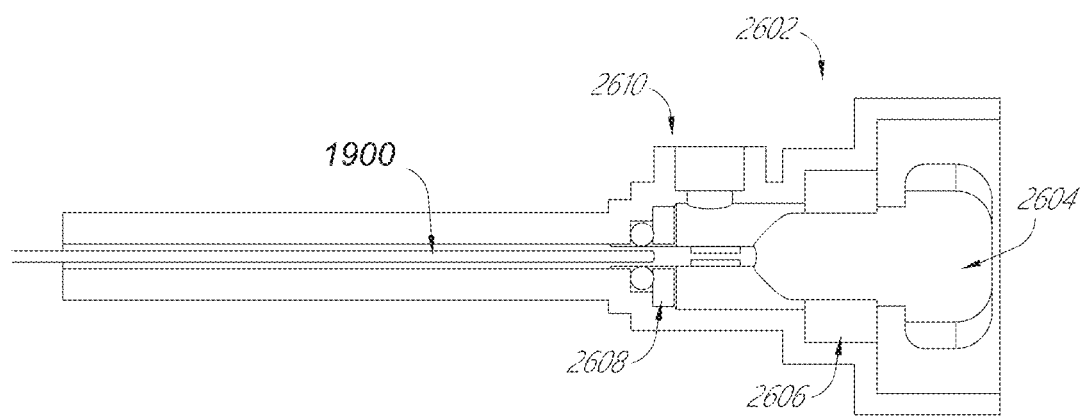
FIG. 27B illustrates an enlarged longitudinal cross-sectional elevational view of the proximal drive assembly 2602 from FIG. 27A.
Figure 28:
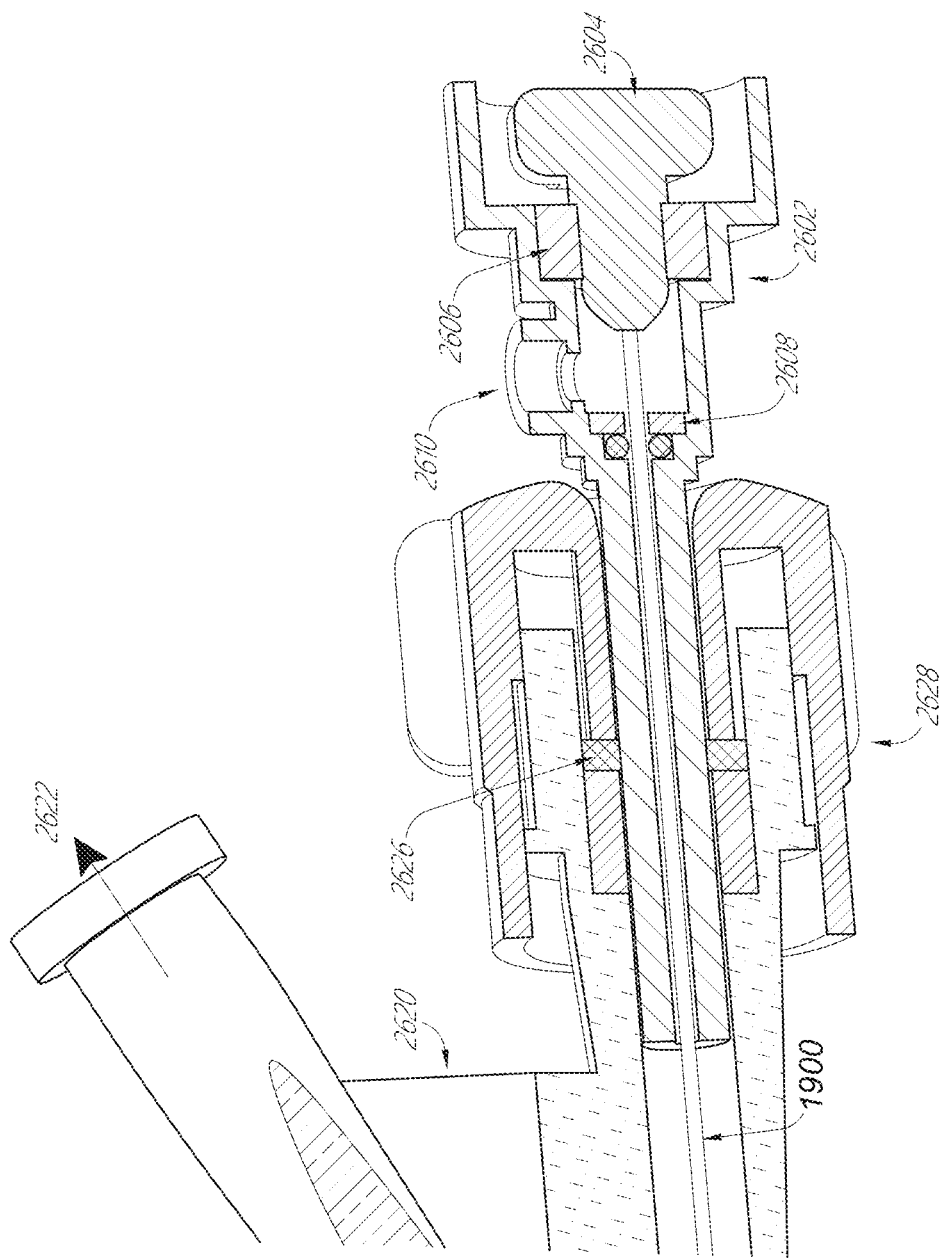
FIG. 28 depicts a cross-sectional perspective view of the proximal portion of FIG. 26.

Referring to FIG. 26, there is illustrated a proximal drive assembly and/or the rotating hemostasis valve to provide the interface for driving the agitator 1900, providing the port for injecting media, and the aspiration port. Referring to FIGS. 26, 27A, 27B, and 28, the proximal drive assembly 2602 and the rotating hemostasis valve 2620 may be releasably or permanently coupled to the proximal end of the agitator 1900. The proximal portion of the agitator 1900 passes proximally through a lumen of the rotating hemostasis valve 2620 and then that of the proximal drive assembly 2602. The proximal end of the agitator 1900 may terminate inside the lumen of the proximal drive assembly 2602. The distal portion of the proximal drive assembly 2602 is inserted into the proximal end of the rotating hemostasis valve 2620. In another embodiment, the proximal drive assembly 2602 may be integrated into the rotating hemostasis valve 2620.

The rotating hemostasis valve (RHV) 2620 comprises a distal connector 2630 at its distal end, which is configured to couple the rotating hemostasis valve to the proximal end of the catheter (not shown). The distal connector 2630 may be a luer connector. The rotating hemostasis valve 2620 comprises a central lumen along its longitudinal length, through which a proximal section of agitator 1900 passes. The rotating hemostasis valve 2620 further comprises an aspiration port 2622, which bifurcates from the central lumen of the rotating hemostasis valve 2620 and provides the aspiration flow path. The rotating hemostasis valve 2620 comprises a RHV seal 2626 and a proximal rotating collar 2628 at its proximal end. The proximal rotating collar 2628 controls the opening and closing of the RHV seal 2626. The user (e.g., physician) can either open or close the RHV seal 2626 by rotating the proximal rotating collar 2628. The RHV seal 2626, when closed, does not allow fluid communication between the inside lumen distal of the RHV seal 262 and the inside lumen proximal of the RHV seal 262. At the same time, the RHV seal 262 does not hamper the longitudinal movement of the distal portion of the proximal drive assembly 2602 inside the rotating hemostasis valve 2629.

Experiments showed that as the wire or hypo tube 1900 is rotated back and forth (i.e., oscillating), the distal end of the agitator 1900 changes its position relative to the catheter. The distal end of the agitator 1900 was shown to foreshorten/lengthen as the wire or hypo tube 2624 wound/unwound within the catheter due to the rotation of the agitator 1900 or the increase/decrease in media injection pressure. The proximal rotating collar 2628 and the RHV seal 2626 permit the user (e.g., physician) to account for this variance in length and advance/withdraw the agitator 1900 relative to the catheter and fix it in place by simply moving the proximal drive assembly 2602 in/out of the rotating hemostasis valve 2629. If the agitator 1900 is preloaded into the catheter, the distance may be initially set at a nominal position. In another embodiment, the proximal rotating collar 2628 of the rotating hemostasis valve 2620 may be part of the proximal drive assembly 2602.

The proximal drive assembly 2602 comprises a proximal drive connector 2604, to which the driver is connected, and a media injection port 2610, into which media is injected. The proximal drive assembly also comprises a bearing 2606, which allows free rotation of the proximal drive connector 2604 with respect to the proximal drive assembly 2602. The proximal drive connection 2604 may be coupled to the proximal end of the agitator 1900 such that the rotation of the proximal drive connector 2604 is translated to the rotation of the wire or hypo tube 1900. The proximal drive assembly further comprises a drive tube seal 2608, which prevents fluid communication between the inside lumen (of the proximal drive assembly 2602) distal of the drive tube seal 2608 and the inside lumen proximal of the drive tube seal 2608.

Figure 29:
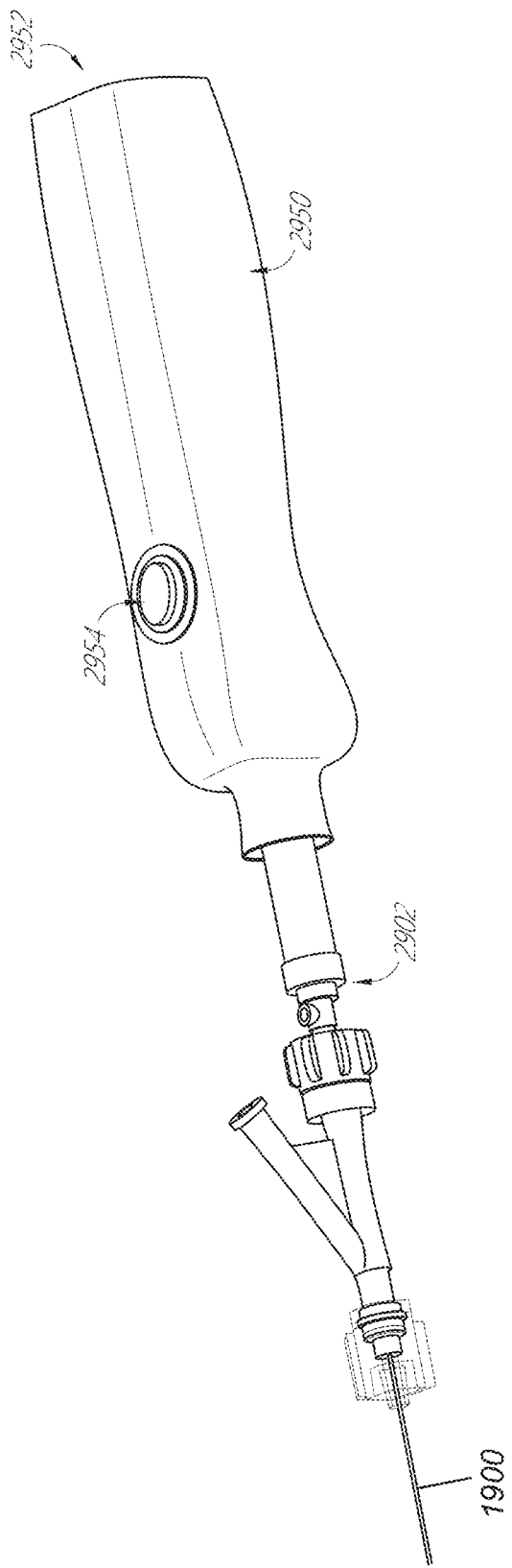
FIG. 29 depicts a perspective view of an agitator driver, a proximal drive assembly, and a rotating hemostasis valve.

Referring to FIG. 29, the driver 2950 is removably connected to the proximal end of the proximal drive assembly 2902 via the proximal drive connection 2604. The driver 2950 is configured to drive the agitator 1900. The driver 2950 is a motorized driver that is automatically controlled with respect to one or more factors such as direction (CCW/CW), speed, duration, etc. The driver 2950 comprises a control 2954 such as a button, which executes a preprogrammed series of steps when pushed. The driver 2954 may be under synchronized control, in which the driver 2954 drives the agitator 1900 in synchronization with aspiration and media injection, when the back of the driver 2950 is plugged into the synchronization port 2952.

The system for retrieving clots comprises the aspiration catheter; the agitator 1900 longitudinally extendable inside the lumen of the aspiration catheter; and the driver connectable to the proximal end of the agitator 1900 (e.g., via the rotating hemostasis valve or the proximal drive assembly) with or without a synchronization port. The system may allow impulse aspiration and/or impulse injection of media. The media may comprise water, saline solution, or media with an effective amount of drug (e.g., drug therapy such as heparin, plavix, tPA). The components may be manipulated individually or in a synchronized manner using predetermined operating parameters (e.g., for synchronized aspiration, injection, and rotation).

The method of retrieving a clot may comprise providing the aspiration catheter, the agitator longitudinally extending or positionable inside the lumen of the aspiration catheter; and the driver coupled to the proximal end of the agitator; placing the catheter adjacent to the clot; attempting to aspirate clot; if not successful, advancing an agitator distally through the catheter; activating the driver to rotate the agitator and loosen the clot; optionally injecting media through the agitator to lubricate the clot and/or create a media jet from the distal end of the agitator, configured to help aspirate the clot; transporting the clot proximally inside the lumen of the catheter by applying the vacuum at the proximal end of the catheter; and optionally pulsing the vacuum. As pieces of the clot separate, transport may be assisted by the rotating agitator and/or injection media.

In order to detach a more stubborn clot, aspiration, media injection, and/or rotation of the wire or hypo tube may be timed. Building up a surplus of media around the clot will form a plug. When aspiration is activated and/or pulsed, the vacuum can draw the "plug" proximally inside the lumen of the wire or hypo tube like a syringe plunger. A higher local vacuum around the clot is maintained, and more momentum is added to the "plug" as more media is added. Timing the rotation of the wire or hypo tube with aspiration and media injection may help wiggle or fatigue the clot and detach it out of the vasculature.

Any of the catheter shaft or sections of the catheter shaft or telescoping extensions in accordance with the present invention may comprise a multi-layer construct having a high degree of flexibility and sufficient push ability to reach deep into the cerebral vasculature, such as at least as deep as the petrous, cavernous, or cerebral segment of the internal carotid artery (ICA).

Figure 30:
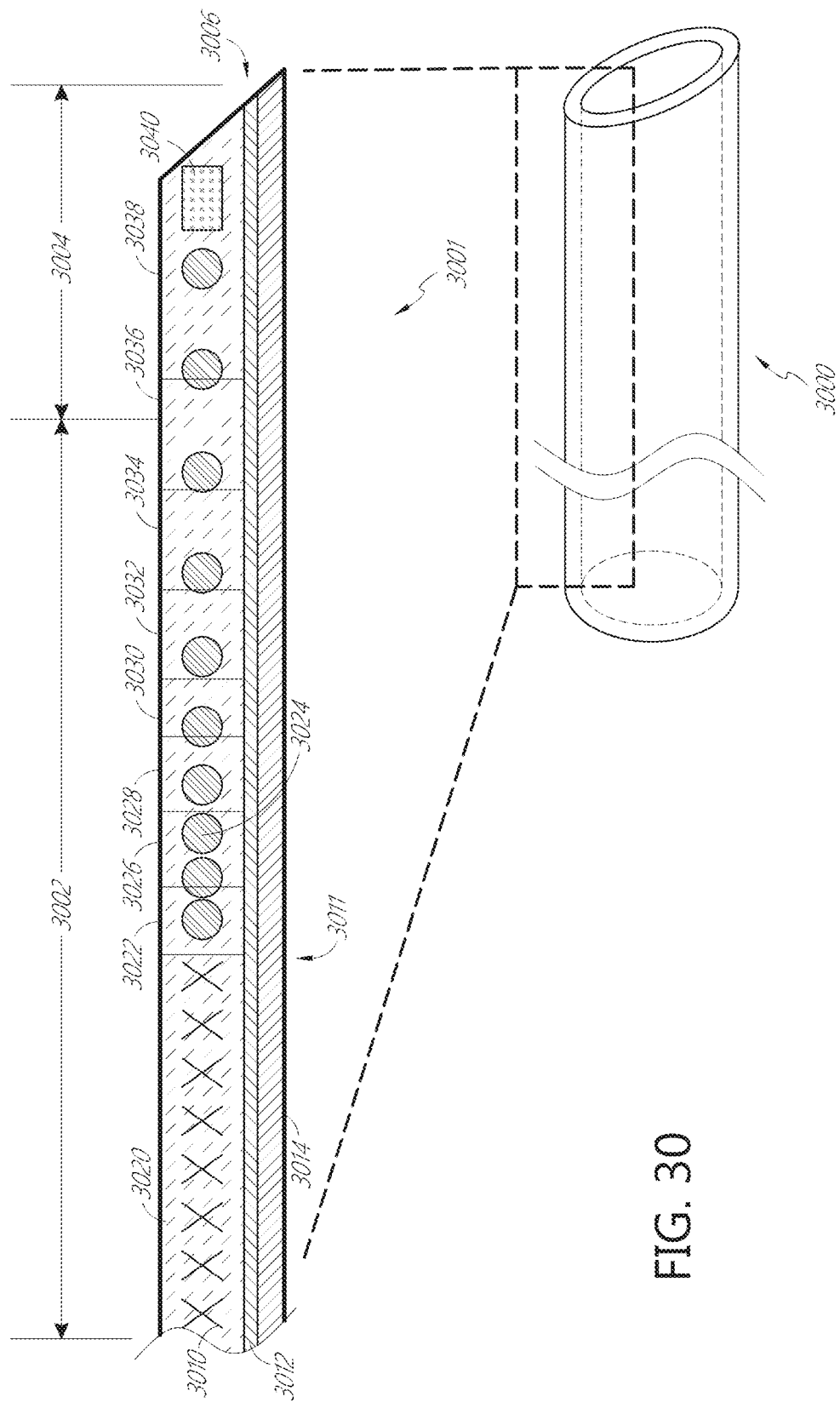
FIG. 30 illustrates a cross-sectional elevational view of a catheter wall according to an embodiment.

In one example, referring to FIG. 30, the catheter 3000 may have an effective length from the manifold to distal tip from about 70 cm to about 150 cm, from about 80 cm to about 140 cm, from about 90 cm to about 130 cm, from about 100 cm to about 120 cm, or from about 105 cm to about 115 cm. The outer diameter of the catheter 3000 may be from about 0.07 inches to about 0.15 inches, from about 0.08 inches to about 0.14 inches, from about 0.09 inches to about 0.13 inches, from about 0.1 inches to about 0.12 inches, or from about 0.105 inches to about 0.115 inches, and may be lower in a distal segment than in a proximal segment. The inner diameter 3108 of the catheter 3000 in a single central lumen 3001 embodiment may be greater than or equal to about 0.11 inches, greater than or equal to about 0.1 inches, greater than or equal to about 0.09 inches, greater than or equal to about 0.088 inches, greater than or equal to about 0.08 inches, greater than or equal to about 0.07 inches, greater than or equal to about 0.06 inches, or greater than or equal to about 0.05 inches. The inner diameter 3108 of the catheter 3000 in a single central lumen 3001 embodiment may be less than or equal to about 0.11 inches, less than or equal to about 0.1 inches, less than or equal to about 0.09 inches, less than or equal to about 0.088 inches, less than or equal to about 0.08 inches, less than or equal to about 0.07 inches, less than or equal to about 0.06 inches, or less than or equal to about 0.05 inches. Referring to FIG. 30, an inner liner 3014 may be formed by dip coating a mandrel (not shown) to provide a thin walled tubular inside layer of the catheter body 3000. The dip coating may be produced by coating a wire such as a silver coated copper wire in PTFE. The mandrel may thereafter be axially elongated to reduce diameter, and removed to leave the tubular inner liner. The outside surface of the tubular inner liner 3014 may thereafter be coated with a soft tie layer 3012 such as polyurethane (e.g., Tecoflex™), to produce a layer having a thickness of no more than about 0.005 inches, and in some implementations approximately 0.001 inches. The tie layer 3012 will generally extend along at least about the most distal 10 cm or 20 cm of the catheter shaft 3000 generally less than about 50 cm and may in one implementation extend approximately the distal 30 cm of the catheter shaft 3000, 3100.

A braid such as a 75 ppi stainless steel braid 3010 may thereafter be wrapped around the inner liner 3014 through a proximal zone up to a distal transition 3011. From the distal transition 3011 to the distal end of the catheter 3000, a coil 3024 comprising a shape memory material such as a Nitinol alloy may thereafter be wrapped around the inner liner 3014. In one implementation, the Nitinol coil has a transition temperature below body temperature so that the Nitinol reside in the austinsite (springy) state at body temperature. Adjacent loops or filars of the coil may be closely tightly wound in a proximal zone with a distal section having looser spacing between adjacent loops. In an embodiment having a coil section 3024 with an axial length of between about 20% and 30% of the overall catheter length, (e.g., 28 cm coil length in a 110 cm catheter shaft 3000), at least the distal 1 or 2 or 3 or 4 cm of the coil will have a spacing that is at least about 130%, and in some implementations at least about 150% or more than the spacing in the proximal coil section. In a 110 cm catheter shaft 3000 having a Nitinol coil the spacing in the proximal coil may be about 0.004 inches and in the distal section may be at least about 0.006 inches or 0.007 inches or more.

The distal end of the coil 3024 is spaced proximally from the distal end of the inner liner 3014 to provide room for an annular radiopaque marker 3040. In one embodiment, the distal end of the catheter 3000 is provided with a beveled distal surface 3006 residing on a plane having an angle of at least about 10° or 20° and in one embodiment about 30° with respect to a longitudinal axis of the catheter 3000. The radiopaque marker 3040 may reside in a plane that is transverse to the longitudinal axis. Alternatively, at least the distally facing edge of the annular radiopaque marker 3040 may be an ellipse, residing on a plane which is inclined with respect to the longitudinal axis to complement the bevel angle of the distal surface 3006.

After applying the proximal braid 3010, the distal coil 3024 and the RO marker 3040 an outer Jacket 3020 may be applied such as a shrink wrap tube to enclose the catheter body 3000. The outer shrink-wrapped sleeve 3020 may comprise any of a variety of materials, such as polyethylene, polyurethane, PEBAX, nylon or others known in the art. Sufficient heat is applied to cause the polymer to flow into and embed the proximal braid and distal coil.

In one implementation, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 3000 and provide a smooth continuous outer tubular body. The foregoing construction may extend a long at least the most distal 10 cm, and preferably at least about the most distal 20 or 25 cm of the catheter body 3000.

Figure 31A:
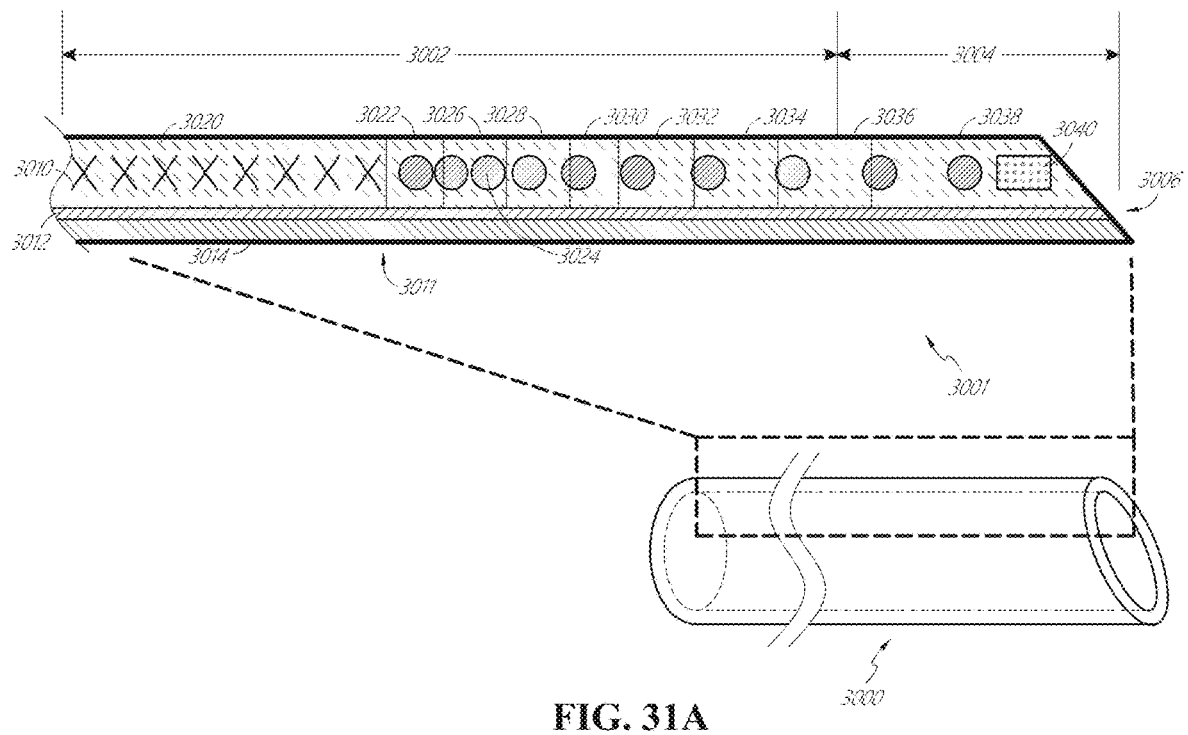
FIG. 31A illustrates a cross-sectional elevational view of a catheter wall according to another embodiment, showing one or more axially extending filaments.

The durometer of the outer wall segments may decrease in a distal direction. For example, proximal segments such as 3022 and 3026, may have a durometer of at least about 60 or 70 D, with gradual decrease in durometer of successive segments in a distal direction to a durometer of no more than about 35 D or 25 D or lower. A 25 cm section may have at least about 3 or 5 or 7 or more segments and the catheter 3000 overall may have at least about 6 or 8 or 10 or more distinct flexibility zones. The distal 1 or 2 or 4 or more segments 3036, 3038, may have a smaller OD following shrinking than the more proximal segments 3022-3034 within a larger OD section 3002, as illustrated in FIGS. 30 and 31A, to produce a step down in OD for the finished catheter body 3000. The length of the lower OD section 3004 may be within the range of from about 3 cm to about 15 cm and in some embodiments is within the range of from about 5 cm to about 10 cm such as about 7 or 8 cm, and may be accomplished by providing the distal segments 3036, 3038 with a lower wall thickness.

Figure 31B:
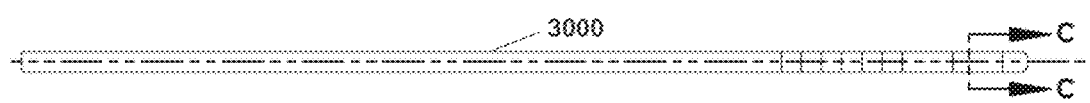
FIG. 31B describes a side elevational view of the catheter of FIG. 31A
Figure 31C:
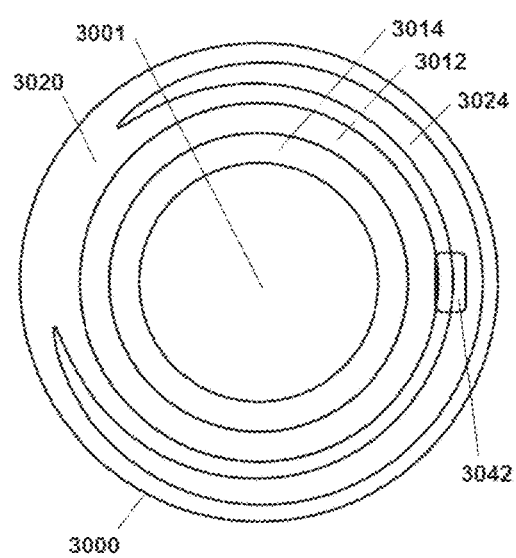
FIG. 31C illustrates a cross-sectional view taken along the line C-C of FIG. 31B, showing one or more axially extending filaments.

Referring to FIGS. 31A-31C, the catheter may further comprise a tension support for increasing the tension resistance in the distal zone. The tension support may comprise a filament and, more specifically, may comprise one or more axially extending filaments 3042. The one or more axially extending filaments 3042 may be axially placed inside the catheter wall near the distal end of the catheter. The one or more axially extending filaments 3042 serve as a tension support and resist elongation of the catheter wall under tension (e.g., when the catheter is being proximally retracted through tortuous vasculature). At least one of the one or more axially extending filaments 3042 may proximally extend along the length of the catheter wall from near the distal end of the catheter to less than about 5 cm from the distal end of the catheter, less than about 10 cm from the distal end of the catheter, less than about 15 cm from the distal end of the catheter, less than about 20 cm from the distal end of the catheter, less than about 25 cm from the distal end of the catheter, less than about 30 cm from the distal end of the catheter, less than about 35 cm from the distal end of the catheter, less than about 40 cm from the distal end of the catheter, or less than about 50 cm from the distal end of the catheter. The one or more axially extending filaments 3042 may have a length greater than or equal to about 50 cm, greater than or equal to about 40 cm, greater than or equal to about 35 cm, greater than or equal to about 30 cm, greater than or equal to about 25 cm, greater than or equal to about 20 cm, greater than or equal to about 15 cm, greater than or equal to about 10 cm, or greater than or equal to about 5 cm. At least one of the one or more axially extending filaments 3042 may have a length less than or equal to about 50 cm, less than or equal to about 40 cm, less than or equal to about 35 cm, less than or equal to about 30 cm, less than or equal to about 25 cm, less than or equal to about 20 cm, less than or equal to about 15 cm, less than or equal to about 10 cm, or less than or equal to about 5 cm. At least one of the one or more axially extending filaments 3042 may extend at least about the most distal 50 cm of the length of the catheter, at least about the most distal 40 cm of the length of the catheter, at least about the most distal 35 cm of the length of the catheter, at least about the most distal 30 cm of the length of the catheter, at least about the most distal 25 cm of the length of the catheter, at least about the most distal 20 cm of the length of the catheter, at least about the most distal 15 cm of the length of the catheter, at least about the most distal 10 cm of the length of the catheter, or at least about the most distal 5 cm of the length of the catheter.

The one or more axially extending filaments 3042 may be placed near or radially outside the tie layer 3012 or the inner liner 3014. The one or more axially extending filaments 3042 may be placed near or radially inside the braid 3010 and/or the coil 3024. The one or more axially extending filaments 3042 may be carried between the inner liner 3014 and the helical coil 3024.

When more than one axially extending filaments 3042 are placed in the catheter wall, the axially extending filaments 3042 may be placed in a radially symmetrical manner. For example, the angle between the two axially extending filaments 3042 with respect to the radial center of the catheter may be about 180 degree. Alternatively, depending on desired clinical performances (e.g., flexibility, trackability), the axially extending filaments 3042 may be placed in a radially asymmetrical manner. The angle between any two axially extending filaments 3042 with respect to the radial center of the catheter may be less than about 180 degree, less than or equal to about 165 degree, less than or equal to about 150 degree, less than or equal to about 135 degree, less than or equal to about 120 degree, less than or equal to about 105 degree, less than or equal to about 90 degree, less than or equal to about 75 degree, less than or equal to about 60 degree, less than or equal to about 45 degree, less than or equal to about 30 degree, less than or equal to about 15 degree, less than or equal to about 10 degree, or less than or equal to about 5 degree.

The one or more axially extending filaments 3042 may be made of materials such as Kevlar, Polyester, Meta-Para-Aramide, or any combinations thereof. At least one of the one or more axially extending filaments 3042 may comprise a single fiber or a multi-fiber bundle, and the fiber or bundle may have a round or rectangular cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more axially extending filaments 3042, as measured in the radial direction, may be no more than about 1%, 2%, 3%, 4%, 5%, 6%, 7%, 8%, 9%, 10%, 11%, 12%, 13%, 14%, 15%, 20%, 25%, or 30% of that of the catheter 3000. The cross-sectional dimension of the one or more axially extending filaments 3042, as measured in the radial direction, may be no more than about 0.001 inches, about 0.002 inches, about 0.003 inches, about 0.004 inches, about 0.005 inches, about 0.006 inches, about 0.007 inches, about 0.008 inches, about 0.009 inches, about 0.010 inches, about 0.015 inches, about 0.020 inches, about 0.025 inches, or about 0.030 inches.

The one or more axially extending filaments 3042 may increase the tensile strength of the distal zone of the catheter to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 32A:
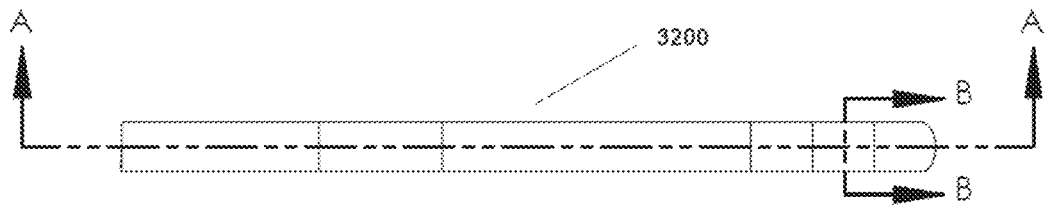
FIG. 32A depicts a side elevational view of a catheter according to one embodiment.
Figure 32B:
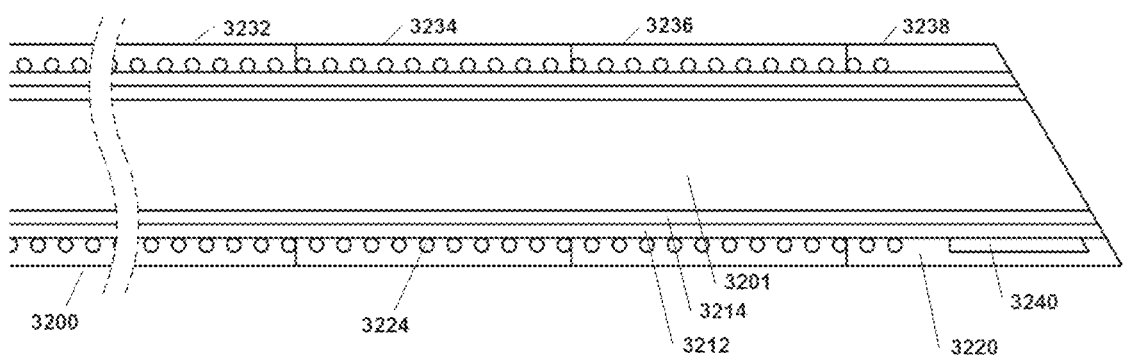
FIG. 32B describes a cross-sectional elevational view taken along the line A-A of FIG. 32A.
Figure 32C:
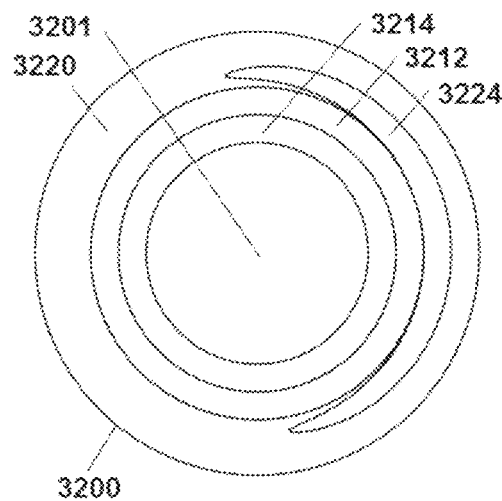
FIG. 32C illustrates a cross-sectional view taken along the line B-B of FIG. 32A.

Referring to FIGS. 32A-32C, depending on whether the catheter 3000 is able to navigate sufficiently distally to reach the target site, an intraluminal catheter 3200 such as a telescopic extension segment having a proximally extending control wire as has been described elsewhere herein (e.g., distal segment 34 in FIGS. 3A and 3B) may be inserted through the catheter 3000 from the proximal end of the catheter 3000. The intraluminal catheter 3200 is inserted such that the distal end of the intraluminal catheter 3200 reaches further distally beyond the distal end of the catheter 3000. The outer diameter of the intraluminal catheter 3200 is smaller than the inner diameter of the catheter 3000. This way, the intraluminal catheter 3200 can slide inside the lumen of the catheter 3000.

The intraluminal catheter 3200 incorporates characteristics of the side wall construction of the catheter 3000 described herein. For example, as illustrated in FIGS. 32A-32C, the intraluminal catheter may comprise a plurality of short tubular segments 3232, 3234, 3236, 3238; coil 3224; a central lumen 3201; an inner liner 3214; a tie layer 3212; an outer shrink wrap jacket 3220; and an annular radiopaque marker 3240. The axial length of the tubular extension segment may be less than about 50% and typically less than about 25% of the length of the catheter 3000. The axial length of the tubular extension segment will generally be at least about 10 cm or 15 cm or 20 cm or 25 cm or more but generally no more than about 70 cm or 50 cm or 30 cm.

Figure 33A:
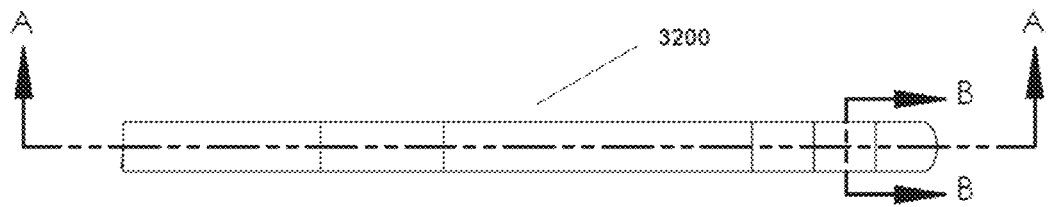
FIG. 33A depicts a side elevational view of a catheter according to another embodiment.
Figure 33B:
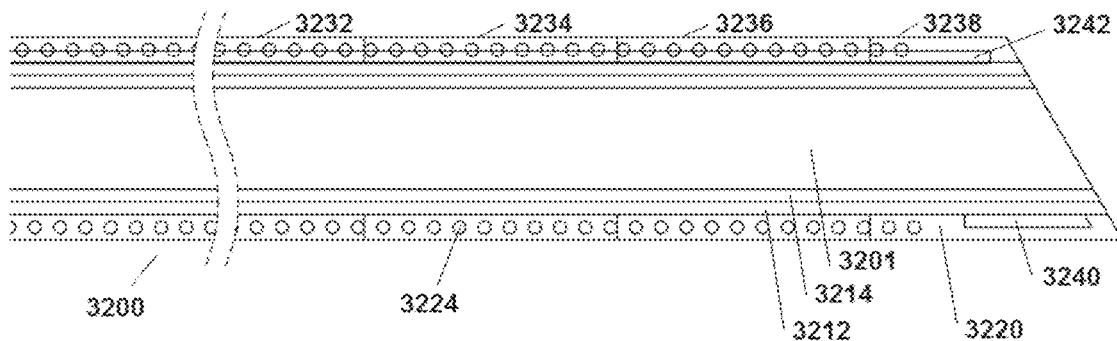
FIG. 33B describes a cross-sectional elevational view taken along the line A-A of FIG. 33A, showing one or more axially extending filaments.
Figure 33C:
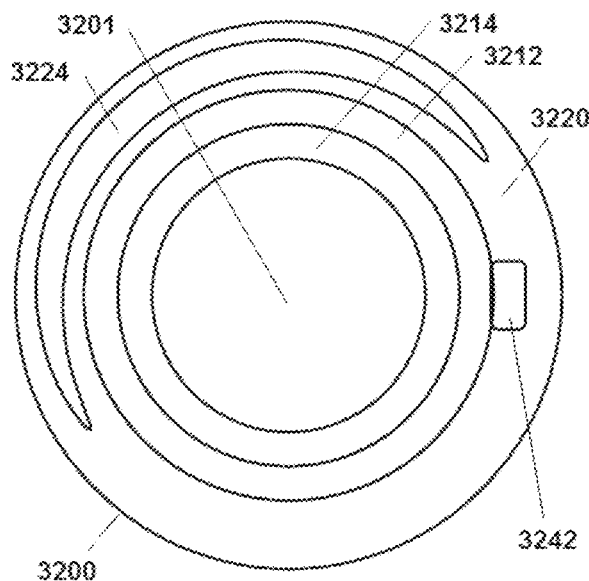
FIG. 33C illustrates a cross-sectional view taken along the line B-B of FIG. 33A, showing one or more axially extending filaments.

Referring to FIGS. 33A-33C, the intraluminal catheter 3200 may have one or more axially extending filaments 3242. The one or more axially extending filaments 3242 incorporate characteristics of the one or more axially extending filaments 3042 of the catheter 3000, except the cross-sectional dimension as measured in the radial direction of the one or more axially extending filaments 3242 of the intraluminal catheter 3200 may be less than the corresponding dimension of the filament 3042 in the catheter 3000.

Figure 34A:
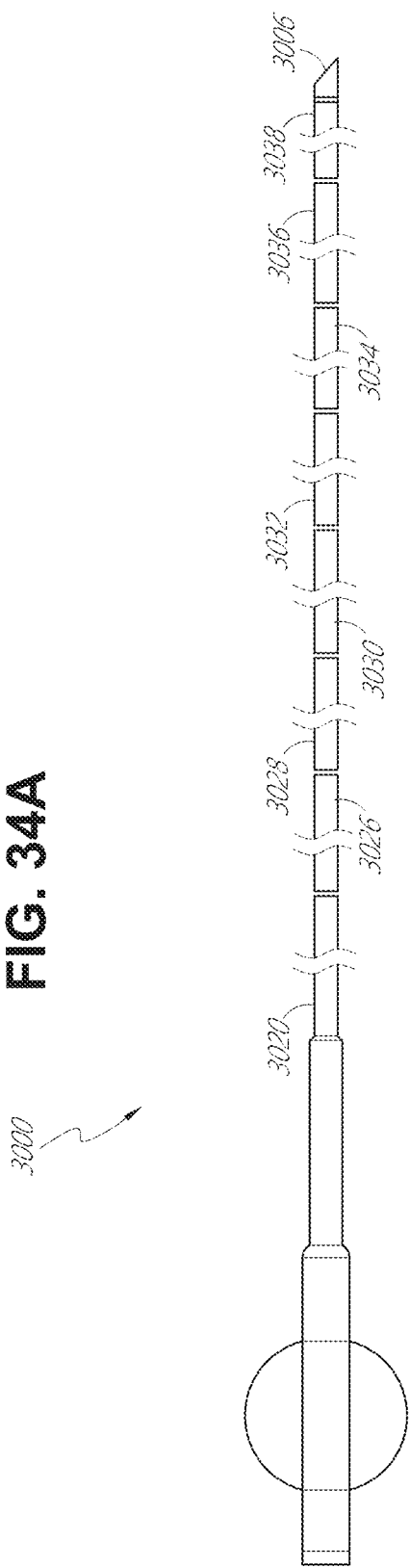
FIG. 34A illustrates a side elevational view of a progressively enhanced flexibility catheter according to an embodiment.
Figure 34B:
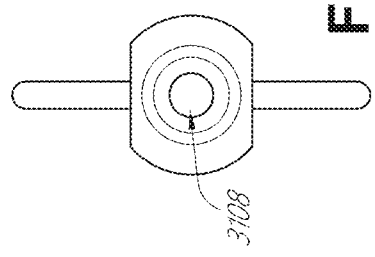
FIG. 34B is a proximal end view of the enhanced flexibility catheter of FIG. 34A.

Referring to FIGS. 34A-34B, there is illustrated one example of an outer jacket segment stacking pattern for a progressive flexibility catheter of the type discussed in connection with FIG. 30. A distal segment 3038 may have a length within the range of about 1-3 cm, and a durometer of less than about 35 D or 30 D. An adjacent proximal segment 3036 may have a length within the range of about 4-6 cm, and a durometer of less than about 35 D or 30 D. An adjacent proximal segment 3034 may have a length within the range of about 4-6 cm, and a durometer of about 35 D or less. An adjacent proximal segment 3032 may have a length within the range of about 1-3 cm, and a durometer within the range of from about 35 D to about 45 D (e.g., 40 D). An adjacent proximal segment 3030 may have a length within the range of about 1-3 cm, and a durometer within the range of from about 50 D to about 60 D (e.g., about 55 D). An adjacent proximal segment 3028 may have a length within the range of about 1-3 cm, and a durometer within the range of from about 35 D to about 50 D to about 60 D (e.g., about 55 D). An adjacent proximal segment 3026 may have a length within the range of about 1-3 cm, and a durometer of at least about 60 D and typically less than about 75 D. More proximal segments may have a durometer of at least about 65 D or 70 D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10 D, preferably at least about 20 D and in some implementations at least about 30 D or 40 D or more.

Figure 35:
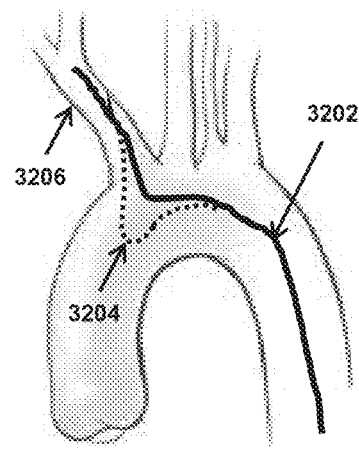
FIG. 35 illustrates back-up support of the catheter in accordance with the present invention.

Performance metrics of a catheter include back-up support, trackability, pushability, and kink resistance. Back-up support means ability of the catheter to remain in position within anatomy and provide a stable platform through which endoluminal devices may advance. Referring to FIG. 35, when the devices are pushed through the catheter 3202, if there is not enough back-up support in the catheter 3202, the distal portion 3204 of the catheter 3202 may prolapse, pull out, or back out of a vessel 3206 that branches out of a main blood vessel (e.g., brachiocephalic artery 82, common carotid artery 80, or subclavian artery 84). Back-up support for the catheter 3202 may be improved by providing a proximal region with high durometer or modulus and a distal region with low durometer or modulus. Durometer or modulus of the proximal region of the catheter 3202 may be improved by braid reinforcement. The region of the catheter at which durometer or modulus is strengthened may be placed near branching points at which the aortic arch 1114, 1214 branches into brachiocephalic artery 82, common carotid artery 80, or subclavian artery 84 or near other anatomical structures (i.e., branching points) at which a main vessel branches into one or more smaller vessels, providing an opportunity for a catheter with poor back-up support to prolapse. For example, the region of the catheter at which durometer or modulus is strengthened may be placed within about 0.5 cm, about 1 cm, about 2 cm, about 3 cm, about 4 cm, about 5 cm, or about 6 cm from a branching point at which a main vessel branches into one or more smaller vessels.

Trackability means ability of the catheter to track further distally than other catheters (e.g., to M1). For example, a catheter that can reach a cerebral segment of the internal carotid artery (ICA) has better trackability than a catheter that can reach a cavernous or petrous segment of the ICA. Trackability of the catheter may be improved by using a catheter wall with low durometer or modulus or by adding a coating (e.g., a hydrophilic coating) on at least a portion of the catheter wall. In one embodiment, the hydrophilic coating may be placed along the distal most region of the catheter. The hydrophilic coating on the catheter may extend to about 1 cm, about 5 cm, about 10 cm, about 15 cm, or about 20 cm from the distal end of the catheter. The region with lower durometer or modulus may locate at the distal most region of the catheter. The region with lower durometer or modulus may extend to about 1 cm, about 5 cm, about 10 cm, about 15 cm, or about 20 cm from the distal end of the catheter.

Pushability means rigidity of the catheter sufficient to push through anatomy without "buckling". Pushability of the catheter may be improved by increasing its durometer or modulus. Pushability of the catheter may also be improved by providing a proximal region with high durometer or modulus and a distal region with low durometer or modulus. A transition region of the catheter in which durometer or modulus changes along its longitudinal length (e.g., decreasing durometer or modulus from the proximal end to the distal end) may begin at about 50%, 60%, 70%, 75%, 80%, or more of the length of the catheter from its proximal end.

Kink resistance means resistance of the catheter to kinking. In addition, if the catheter does kink, kink resistance of the catheter helps it return to its original shape. Kink resistance is important in the distal segment of the catheter, which is more prone to kinking than the proximal segment. Kink resistance of the catheter may be improved by adding one or more NiTi coils (or a coil at least portion of which is Nitinol) to the catheter wall.

Figure 36:
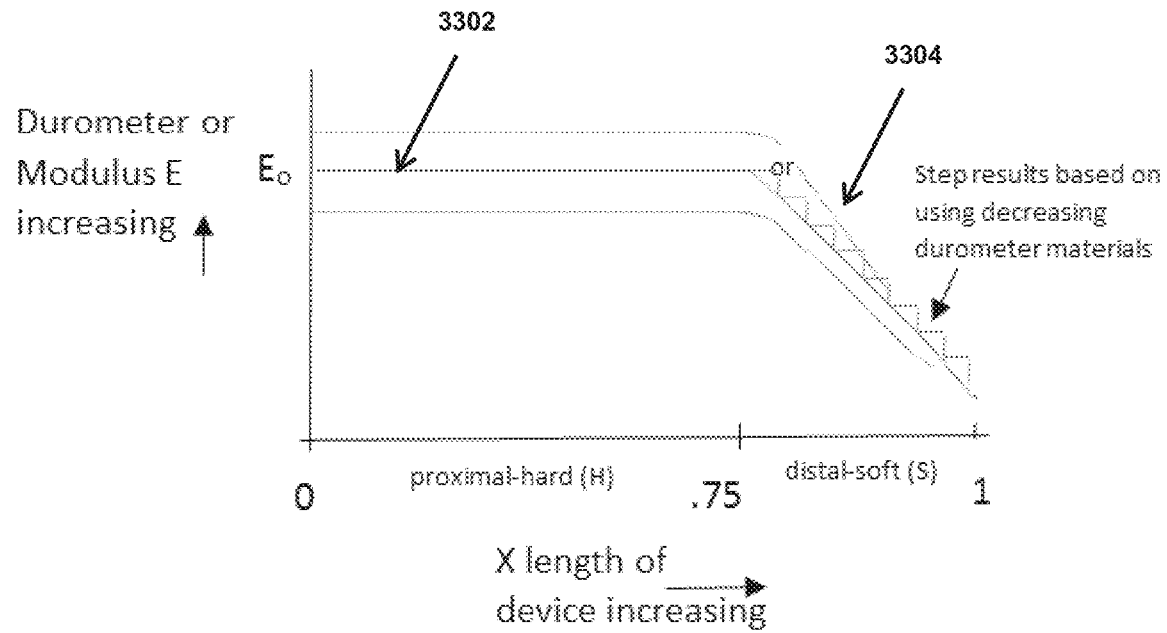
FIG. 36 depicts a graph of modulus or durometer of the catheter along the length of the catheter, from the proximal end to the distal end.

FIG. 36 describes a graph of durometer or modulus of a catheter in accordance with the present invention along the length of the catheter, from the proximal end (x=0) to the distal end (x=1). The catheter according to an embodiment may have a decreasing durometer or modulus (E) approaching its distal end. The proximal end of the catheter has higher durometer or modulus than that of the distal end of the catheter. High durometer or modulus near the proximal end provides superior back-up support of the catheter. Durometer or modulus of the catheter is substantially constant along its length near the proximal end 3302 of the catheter. Then, durometer or modulus of the catheter decreases near the distal end 3304 of the catheter. Durometer or modulus of the catheter may begin to decrease (i.e., transition region) at about 50%, 70%, 75%, 80%, or 90% of the length of the catheter from its proximal end. The catheter may have successively decreasing durometer or modulus near its distal end by using materials with less durometer or modulus or having a thinner catheter wall near the distal end. Decreased durometer or modulus near the distal end provides superior trackability of the catheter.

Figure 37:
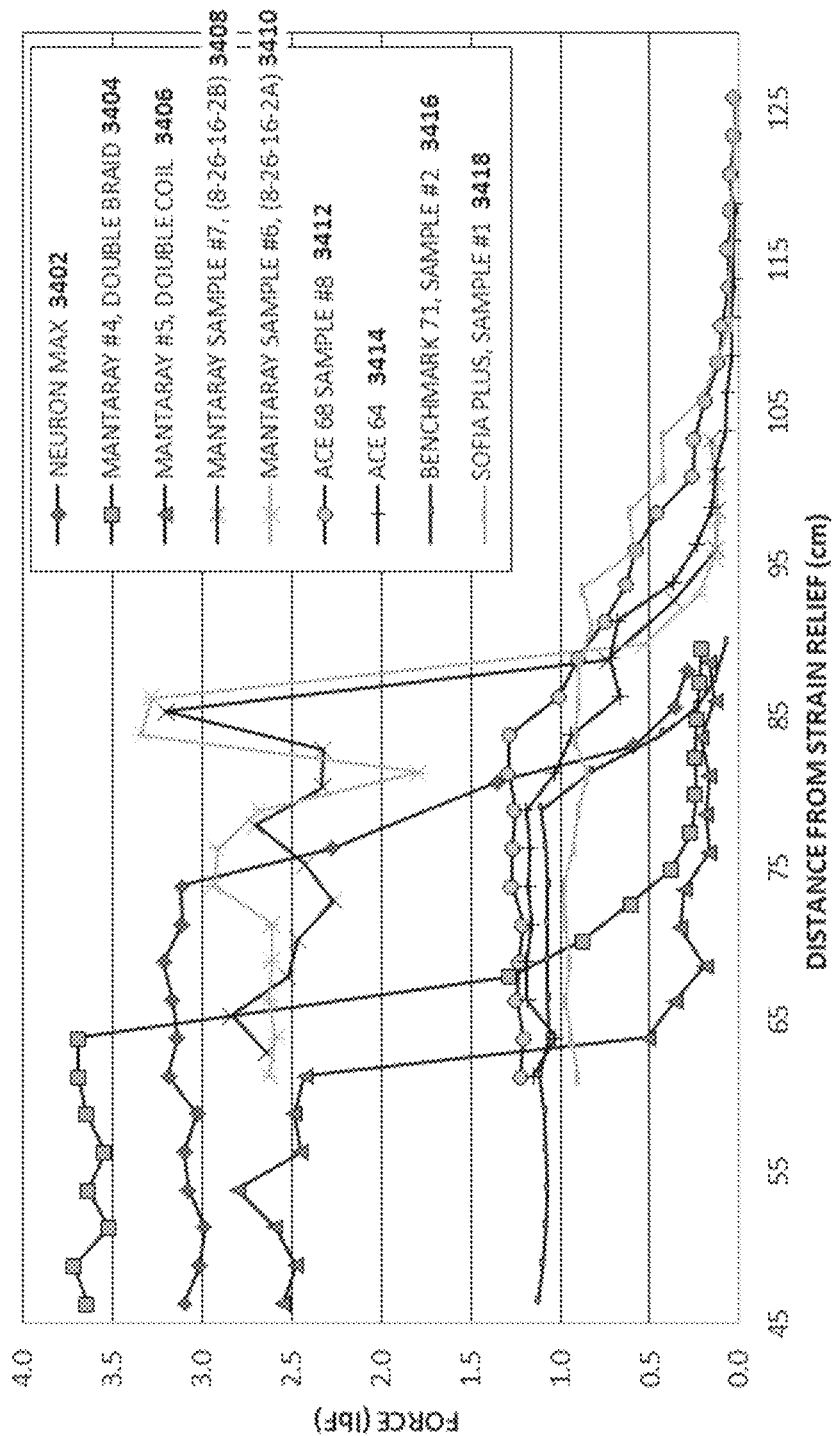
FIG. 37 depicts a graph of flexure test profiles of catheters in accordance with the present invention compared with conventional catheters.

FIG. 37 describes flexibility test profiles of catheters in accordance with the present invention compared with conventional catheters. Flexibility of a catheter was measured by the three point flexural test with a span of one inch and a displacement of 2 mm. In other words, FIG. 37 describes a force (i.e., flexural load) necessary to vertically displace an one-inch-long catheter segment by 2 mm with respect to distance from strain relief (i.e., proximal end of the catheter) to the point of force application. All catheters tested in FIG. 37 show modulus or flexibility profiles similar to one shown in FIG. 36. Modulus of the catheters stays substantially constant along its length near the proximal end and then gradually decreases near the distal end.

Catheters according to the present invention have a flexural load that is substantially constant along the longitudinal length near the proximal end and a rapidly decreasing flexural load near the distal end. In a catheter having a length of about 125 cm, the catheters may have a flexural load greater than or equal to about 1.0 lbF, about 1.5 lbF, about 2.0 lbF, about 2.5 lbF, about 3.0 lbF, or about 3.5 lbF at about 85 cm from the proximal end. The catheters may have a flexural load less than or equal to about 2.5 lbF, about 2.0 lbF, about 1.5 lbF, about 1.0 lbF, or about 0.5 lbF at about 95 cm from the proximal end. The catheters may have a flexural load less than or equal to about 1.5 lbF, about 1.0 lbF, about 0.75 lbF, about 0.5 lbF, about 0.25 lbF, or about 0.1 lbF at about 105 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 115 cm from the proximal end. For catheters having different lengths, the foregoing dimensions can be scaled from the distal end of the catheter as a percentage of catheter length.

In certain implementations constructed in accordance with FIG. 30, the flexural load is less than about 3.0 or 3.25 lbF at 65 cm from the proximal end and greater than about 2.25 or 2.5 lbF on average from 65 cm to 85 cm from the proximal end. Flexural load drops to no more than about 1.0 and preferably no more than about 0.5 lbF at about 95 cm from the proximal end. This provides enhanced backup support in the aorta while maintaining enhanced trackability into the distal vasculature.

In other embodiments, the catheters may have a flexural load greater than or equal to about 1.0 lbF, about 1.5 lbF, about 2.0 lbF, about 2.5 lbF, about 3.0 lbF, or about 3.5 lbF at about 60 cm from the proximal end. The catheters may have a flexural load less than or equal to about 2.0 lbF, about 1.5 lbF, about 1.0 lbF, or about 0.5 lbF at about 70 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 80 cm from the proximal end. The catheters may have a flexural load less than or equal to about 1.0 lbF, about 0.75 lbF, about 0.5 lbF, about 0.4 lbF, about 0.3 lbF, about 0.2 lbF, or about 0.1 lbF at about 90 cm from the proximal end.

The catheters may have a transition region, in which its flexural load changes by greater than or equal to about 1.0 lbF, about 1.5 lbF, about 2.0 lbF, about 2.5 lbF, about 3.0 lbF, or about 3.5 lbF. The longitudinal length of the transition region may be less than or equal to about 20 cm, about 15 cm, about 10 cm, about 5 cm, about 3 cm, or about 1 cm.

Compared to Neuron Max (Penumbra, Inc.) 3402, catheters according to the present invention (e.g., 3404, 3406, 3408, 3410) have comparable modulus near its proximal end. This way, the catheters according to the present invention provide back-up support comparable to that of Neuron Max. In addition, the catheters have modulus that falls more rapidly near the transition region (between the proximal end and the distal end) than that of Neuron Max.

Compared to Ace 68 catheter (Penumbra) 3412, Ace 64 catheter (Penumbra) 3414, Benchmark 71 catheter (Penumbra) 3416, and Sofia Plus (MicroVention) 3418, the catheters according to the present inventions have greater modulus near its proximal end and comparable modulus near its distal end. This way, the catheters according to the present invention provide superior back-up support with comparable trackability compared to conventional catheters. The catheters according to the present invention may achieve this modulus profile even when their inner diameters (and thus lumen volumes) are greater than or equal to those of Ace 68, Ace 64, Benchmark 71, and Sofia Plus, which range from 0.064 inch to 0.071 inch.

Referring to FIG. 38, there is illustrated a transformable access sheath 200. The access sheath 200 comprises an elongate flexible tubular body 202 extending between a proximal end 204 and a distal end 206. A proximal access port 208 is in communication with a distal port 210 on the distal end 206 by way of a central lumen 212. See FIG. 39.

At least one transition zone 214 is provided on the tubular body 202. Transition zone 214 is controllably transformable between a relatively stiff configuration and a relatively flexible configuration. The access sheath 200 may be distally advanced through tortuous anatomy with at least one transition zone 214 in a relatively stiff configuration as desired such as to provide column strength or to facilitate the introduction of instruments therethrough. The transition zone 214 may be controllably transformed to a relatively flexible configuration as desired, such as to navigate tight bends in the vasculature.

In the illustrated embodiment, three transition zones 214 are shown. However, one or two or three or four or more transition zones may be utilized, depending upon the desired clinical performance. The transition zone 214 may be from about 1 cm to about 20 or 30 cm or more in length. In certain embodiments, the transition zones will be within the range of from about 2 cm to about 10 cm in length. The length and location of the transition zones may depend upon the target anatomy for the access catheter, and can be located accordingly.

Referring to FIG. 39, there is illustrated a cross-sectional view taken along the lines 18-18 of FIG. 38, through a transition zone 214. The tubular body 202 comprises a sidewall 216 having at least one heating element 218 carried by or embedded within the sidewall 216. In the illustrated embodiment, the heater 218 may be an electrically conductive filament, such as a filar on an electrically conductive helical coil or braid. The electrically conductive filament may be placed within or laminated within an inner layer and an outer layer of the sidewall 216. In at least one embodiment, an inner layer of the sidewall 216 may comprise polytetrafluoroethylene (PTFE) for lubricity. In at least one embodiment, an outer layer of the sidewall 216 may comprise biocompatible material preferably with a glass transition temperature from about 40° C. to about 80° C.

Alternatively, an electrically conductive polymer may be utilized to form the sidewall 216. Electrically conductive coatings may alternatively be printed, laminated, embedded or otherwise applied to the outside, the inside, or laminated within an inner layer and an outer layer of the sidewall 216. In at least one embodiment, the resistance of the heater 218 may be calibrated to a specific heating temperature, such as 40-80° C., for a predetermined voltage level of the power source. This may eliminate the need for a thermocouple and prevent potential overheating.

One or more electrical conductors may extend between the transition zone 214 and a proximal activation port 215, adapted for coupling to a source of electricity from an external controller. In a mono polar construction, a single conductor for each transition zone 214 may extend proximally to the activation port 215. A second conductor may lead to or comprise an electrically conductive surface on the tubular body 202, for conducting electricity through the body of the patient to an external electrode as is understood in the art. Alternatively, in a bipolar embodiment, each transition zone 214 may be provided with at least two electrical conductors extending proximally to the activation port 215.

At least the transition zone comprises a biocompatible material that is relatively firm at body temperature (e.g., 37° C.) but transitions to a relatively soft, flexible material upon application of heat. Typical suitable materials have a relatively low melting point so as to be softenable at temperatures not so high as to damage living vessels. In any event the material will have a softening point or a glass transition temperature above body temperature, with a melting point significantly above body temperature and above the temperature reached by activating the heating element 218. In one embodiment, the biocompatible material preferably has a glass transition temperature from about 40° C. to about 80° C. Suitable materials may include polymers with a polymer chain orientation that causes the polymer to break when heated.

Examples of suitable biostable materials are polymers, typically thermoplastic polymers such as polyolefins and polyurethanes and most other biocompatible polymers. Typical suitable bioabsorbable materials include polyglycolide (PGA), poly(L-lactide) (PLLA), poly(.epsilon.-caprolactone) (PCL), and blends or combinations thereof. Polyglycolide for example has a glass transition temperature between 35-40° C., such having a considerably higher melting point.

Typical operating (softening) temperatures in this regard are on the order of between about 40 and 80° C., often between about 40° C. and 60° C. to cause a softening transition of the transition zone 214, and allow a transition back to a firm state upon removal of power and reversion of the transition zone 214 back to body temperature. A temperature higher than about 80° C. may be acceptable for a short period of time, depending upon the total energy delivered. Any temperature to which the heater 218 is elevated is limited by what the body of the patient can handle without causing damage to the vessel wall or causing thrombus to form. For this reason, it may be desirable to remain within the lower end of the temperature ranges illustrated above if the eligible polymers exhibit suitable flexibility at the softening point temperature and suitable firmness at the lower body temperature.

Upon being heated, the biocompatible energy-activated transition zone 214 softens so that it may be navigated through a tight bend for example. The material is to be softened enough by the energy application so that it increases in flexibility, but retains the structural integrity necessary for navigation and retains its shape so that upon interruption of the heat source it will harden back to its original configuration. To maintain the integrity of the tubular body, side wall 216 may be provided with flexible reinforcing structures such as a helically wrapped wire, ribbon or polymeric strand such as polyimide, or other braid or weave as is understood in the neurovascular catheter arts. A resistance coil or other resistance filaments may also provide the mechanical reinforcing function while the transition zone is in the softened state.

Heating may alternatively be provided by positioning a heat source such as a resistance heat element carried by a heater catheter within the central lumen 212. Once the catheter has reached its final position in the vasculature, the heater catheter may be proximally withdrawn from the central lumen 212, which is now available for aspiration or to receive a distal section 34 therethrough. In either heater configuration, a power source may be provided within or electrically coupled to a proximal manifold on the aspiration catheter or heater catheter.

Access for the catheter of the present invention can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery in emergency situations.

Avoiding a tight fit between the guidewire 40 and inside diameter of guidewire lumen 28 enhances the slidability of the catheter over the guidewire. In ultra small diameter catheter designs, it may be desirable to coat the outside surface of the guidewire 40 and/or the inside surface of the wall defining lumen 38 with a lubricous coating to minimize friction as the catheter 10 is axially moved with respect to the guidewire 40. A variety of coatings may be utilized, such as Paralene, Teflon, silicone, polyimide-polytetrafluoroethylene composite materials or others known in the art and suitable depending upon the material of the guidewire or inner tubular wall 38.

Aspiration catheters of the present invention which are adapted for intracranial applications generally have a total length in the range of from 60 cm to 250 cm, usually from about 135 cm to about 175 cm. The length of the proximal segment 33 will typically be from 20 cm to 220 cm, more typically from 100 cm to about 120 cm. The length of the distal segment 34 will typically be in the range from 10 cm to about 60 cm, usually from about 25 cm to about 40 cm.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

The proximal body segment will exhibit sufficient column strength to permit axial positioning of the catheter through a guide catheter with at least a portion of the proximal body segment 33 extending beyond the guide catheter and into the patient's vasculature. The proximal body segment may have a shore hardness in the range from 50 D to 100 D, often being about 70 D to 80 D. Usually, the proximal shaft will have a flexural modulus from 20,000 psi to 1,000,000 psi, preferably from 100,000 psi to 600,000 psi. The distal body segment 34 will be sufficiently flexible and supple so that it may navigate the patient's more narrow distal vasculature. In highly flexible embodiments, the shore hardness of the distal body segment 34 may be in the range of from about 20 A to about 100 A, and the flexural modulus for the distal segment 34 may be from about 50 psi to about 15,000 psi.

The catheter body may further comprise other components, such as radiopaque fillers; colorants; reinforcing materials; reinforcement layers, such as braids or helical reinforcement elements; or the like. In particular, the proximal body segment may be reinforced in order to enhance its column strength and torqueability (torque transmission) while preferably limiting its wall thickness and outside diameter.

Usually, radiopaque markers will be provided at least at the distal end 14 and the transition region 32 at the distal end of proximal segment 33. One radiopaque marker comprises a metal band which is fully recessed within or carried on the outside of the distal end of the proximal body segment 33. Suitable marker bands can be produced from a variety of materials, including platinum, gold, and tungsten/rhenium alloy. Preferably, the radiopaque marker band will be recessed in an annular channel to produce a smooth exterior surface.

The proximal section 33 of tubular body 16 may be produced in accordance with any of a variety of known techniques for manufacturing interventional catheter bodies, such as by extrusion of appropriate biocompatible polymeric materials. Alternatively, at least a proximal portion or all of the length of tubular body 16 may comprise a polymeric or metal spring coil, solid walled hypodermic needle tubing, or braided reinforced wall, as is known in the microcatheter arts.

In a catheter intended for neurovascular applications, the proximal section 33 of body 16 will typically have an outside diameter within the range of from about 0.117 inches to about 0.078 inches. In one implementation, proximal section 33 has an OD of about 0.104 inches and an ID of about 0.088 inches. The distal section 34 has an OD of about 0.085 inches and an ID of about 0.070 inches.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable minimum aspiration flow rate and collapse resistance.

Tubular body 16 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation, to assist in steering. The tubular body 16, and particularly the distal section 34, may be provided with any of a variety of torque and/or column strength enhancing structures. For example, axially extending stiffening wires, spiral wrapped support layers, braided or woven reinforcement filaments may be built into or layered on the tubular body 16. See, for example, U.S. Pat. No. 5,891,114 to Chien, et al., the disclosure of which is incorporated in its entirety herein by reference.

In many applications, the proximal section 33 will not be required to traverse particularly low profile or tortuous arteries. For example, the proximal section 33 will be mostly or entirely within the relatively large diameter guide catheter. The transition 32 can be located on the catheter shaft 16 to correspond approximately with or beyond the distal end of the guide catheter.

For certain applications, such as intracranial catheterizations, the distal section 34 is preferably at least about 5 cm or 10 cm long and small enough in diameter to pass through vessels as low as 3 mm or 2 mm or lower. The distal section may have a length of at least about 20 cm or 30 cm or 40 cm or more, depending upon the intended target vessel or treatment site.

The distal section, whether carried within the proximal section as an integrated device, or is a separate device to be inserted into the proximal section during a procedure, is substantially shorter than the proximal section. When the distal end of the distal section and the distal end of the proximal section are axially aligned, the proximal end of the distal section is spaced distally apart from the proximal end of the proximal section. The control element such as a control wire or tube spans the distance between the proximal end of the distal section and the proximal manifold or proximal control.

In the foregoing configuration, the proximal end of the distal section will generally be spaced apart distally from the proximal end of the proximal section by at least about 25%, and in some embodiments at least about 50% or 70% or more of the length of the proximal section.

In accordance with one aspect, there is provided a method of aspirating a vascular occlusion from a remote site, comprising the steps of: advancing a first elongate tubular body through a vascular access site and into a body vessel; thereafter advancing a second tubular body distally to extend beyond the first elongate tubular body to reach the remote site, the second tubular body having a lumen and a length that is shorter than the first elongate tubular body; and aspirating thrombus from the site into the lumen by applying pulsatile vacuum to the first elongate tubular body.

In one aspect of present disclosure, the aspirating step comprises biting the thrombus by changing the size of a distal opening on the catheter. The changing the size of the opening may be accomplished in response to application of intermittent vacuum to the lumen. In another aspect of present disclosure, the method of aspirating a vascular occlusion further comprises vibrating the first elongate tubular body during the advancing a first elongate tubular body step. In yet another aspect of present disclosure, the method of aspirating a vascular occlusion further comprises vibrating the second tubular body during the advancing a second tubular body step. In yet another aspect of present disclosure, the method of aspirating a vascular occlusion further comprises vibrating at least the distal section of the second tubular body during the aspirating step.

In one aspect of present disclosure, the second tubular body has a proximal opening, and the proximal opening is positioned within the first elongate tubular body within about 25 cm of the distal end of the first elongate tubular body following the advancing the second tubular body distally step. In another aspect of present disclosure, the second tubular body is introduced into the first elongate tubular body following the advancing the first elongate tubular body step. In yet another aspect of present disclosure, the second tubular body is carried within the first elongate tubular body during the advancing the first elongate tubular body step.

In one aspect of present disclosure, the method of aspirating a vascular occlusion may further comprise advancing an agitator into the second tubular body following the advancing a second tubular body step. The method of aspirating a vascular occlusion may further comprise rotating the agitator to assist the aspirating thrombus step. The method of aspirating a vascular occlusion may further comprise introducing a lubricant through the agitator to assist the aspirating thrombus step. More specifically, the method of aspirating a vascular occlusion may further comprise introducing polyethylene glycol through the agitator to assist the aspirating thrombus step.

In one aspect of present disclosure, the aspirating thrombus step comprises applying intermittent negative pressure to the first elongate tubular body. In another aspect of present disclosure, the aspirating thrombus step comprises applying alternating negative and positive pressure to the first elongate tubular body. In yet another aspect of present disclosure, the advancing a second tubular body distally step comprises distally advancing a control wire extending proximally from a proximal end of the second tubular body. The control wire may be tubular, and the method of aspirating a vascular occlusion may further comprise the step of advancing an agitator through the control wire such that a distal segment of the agitator is exposed beyond the control wire and within the second tubular body.

In accordance with one aspect, there is provided a system for aspirating a vascular occlusion from a remote site, comprising: an elongate, flexible tubular body, comprising at least one central lumen extending along its longitudinal length; an agitator extendable through the central lumen of the tubular body to position a distal end of the agitator near a distal end of the tubular body; a driver connectable to a proximal end of the agitator and configured to actuate the agitator; and a vacuum port near the proximal end of the tubular body and in fluid communication with the central lumen of the tubular body.

In one aspect of present disclosure, the agitator comprises an elongate tube. The agitator may comprise a wire extending through the elongate tube and having at least one bend near its distal end. In another aspect of present disclosure, the agitator comprises a proximal end, a distal end, and a loop at the distal end. In yet another aspect of present disclosure, the driver is configured to rotate the agitator cyclically in alternating directions.

In one aspect of present disclosure, the agitator comprises: at least one lumen along its longitudinal length, an influent port near its proximal end configured to allow fluid communication between the lumen of the agitator and a source of media, and at least one effluent port configured to allow fluid communication between the lumen of the agitator and the central lumen of the tubular body. The system for aspirating a vascular occlusion may further comprise a control, for expressing media from the effluent port of the agitator into the central lumen of the tubular body. The distal portion of the tubular body may be configured to vibrate in a transverse direction in response to the injection of media.

In one aspect of present disclosure, the system for aspirating a vascular occlusion further comprises a controller for applying a pulsatile vacuum cycle to the central lumen. In another aspect of present disclosure, the system for aspirating a vascular occlusion further comprises a rotating hemostasis valve coupled to the proximal end of the tubular body, the rotating hemostasis valve comprising: at least one main lumen along its longitudinal length, through which the proximal portion of the agitator is configured to pass, and an aspiration lumen bifurcating from the main lumen and provided with a vacuum port. In yet another aspect of present disclosure, the system further comprises a proximal drive assembly coupled to the proximal end of the tubular body, the proximal drive assembly comprising: at least one main lumen along its longitudinal length for receiving the agitator; a media injection port, into which media is injected, in fluid communication with the central lumen of the tubular body, and a proximal drive connection at the proximal end, which operably connects between the agitator and the driver.

In accordance with another aspect, there is provided a method of aspirating a vascular occlusion from a remote site, comprising: providing the system for aspirating a vascular occlusion; placing the tubular body adjacent to the occlusion; activating the driver to actuate the agitator and loosen the occlusion; and drawing occlusive material into the central lumen by applying vacuum to the central lumen. In one aspect of present disclosure, there is provided a method of aspirating a vascular occlusion from a remote site, comprising: providing the system for aspirating a vascular occlusion; placing the tubular body adjacent to the occlusion; activating the driver to cause the distal tip of the agitator to rotate; injecting media through the influent port; and aspirating occlusive material into the central lumen by applying vacuum to the central lumen. Actuation of the driver, aspiration, and media injection may be synchronized to facilitate the removal and/or aspiration of the occlusion.

In accordance with one aspect, there is provided a method of aspirating a vascular occlusion from a remote site, comprising: advancing a guidewire to a site at least as distal as the cavernous segment of the internal carotid artery; advancing a tubular body directly over the guidewire to a site at least as distal as the cavernous segment; removing the guidewire from the tubular body; and aspirating thrombus into the tubular body by applying vacuum to the tubular body. In one aspect of present disclosure, the method of aspirating a vascular occlusion comprises advancing the tubular body at least as distal as the cerebral segment of the internal carotid artery. In another aspect of present disclosure, the method of aspirating a vascular occlusion comprises advancing the guidewire at least as distal as the middle cerebral artery.

In yet another aspect of present disclosure, the method of aspirating a vascular occlusion further comprises providing sufficient back up support to the tubular body to resist prolapse of the tubular body into the aorta. In one aspect, the back up support may be provided by advancing the tubular body over a guidewire having a distal end positioned at least as distal as the cavernous segment of the internal carotid artery, and a diameter at the point the guidewire enters the brachiocephalic artery of at least about 0.030 inches. In another aspect, the back up support may be provided by advancing the tubular body over a guidewire having a distal end positioned at least as distal as the cavernous segment of the internal carotid artery, and a diameter at the point the guidewire enters the brachiocephalic artery of about 0.038 inches. The guidewire may be navigable to at least the cerebral segment of the internal carotid artery by having a distal segment having a diameter of no more than about 0.020 inches. The guidewire may be navigable to at least the cerebral segment of the internal carotid artery by having a distal segment having a diameter of about 0.016 inches. The distal segment may have a length of no more than about 25 cm. The distal segment may have a length of no more than about 20 cm.

In accordance with another aspect, there is provided a method of tracking an aspiration catheter from a femoral access site to at least as distal as the cavernous segment of the internal carotid artery, comprising the steps of: advancing a guidewire from the femoral access site to at least as distal as the cerebral segment of the internal carotid artery, the guidewire having a proximal section having a diameter of at least about 0.030 inches and a distal section having a length of no more than about 25 cm and a diameter of no more than about 0.020 inches; tracking an aspiration catheter directly over the guidewire and to a site at least as distal as the cavernous segment, the aspiration catheter having a distal end and a central lumen at the distal end with a diameter of at least about 0.080 inches and a beveled distal tip. In one aspect of present disclosure, the diameter of the proximal section of the guidewire is about 0.038 inches, and the diameter of the distal section is about 0.016 inches.

In another aspect of present disclosure, a distal segment of the catheter comprises a side wall defining the central lumen, the side wall comprising: a tubular inner liner; a soft tie layer separated from the lumen by the inner liner; a helical coil surrounding the tie layer, adjacent windings of the coil spaced progressively further apart in the distal direction; and an outer jacket surrounding the helical coil, the outer jacket formed from a plurality of tubular segments positioned coaxially about the coil; wherein a proximal one of the tubular segments has a durometer of at least about 60 D and a distal one of the tubular segments has a durometer of no more than about 35 D. The tubular liner may be formed by dip coating a removable mandrel and may comprise PTFE. The tie layer may comprise polyurethane. The tie layer may have a wall thickness of no more than about 0.005 inches and may extend along at least the most distal 20 cm of the flexible body. The coil may comprise a shape memory material.

In accordance with one aspect, there is provided an enhanced flexibility neurovascular catheter, comprising: an elongate flexible body, having a proximal end, a distal end and a side wall defining a central lumen, a distal zone of the side wall comprising: a tubular inner liner; a soft tie layer separated from the lumen by the inner liner; a helical coil surrounding the tie layer, adjacent windings of the coil spaced progressively further apart in the distal direction; and an outer jacket surrounding the helical coil, the outer jacket formed from a plurality of tubular segments positioned coaxially about the coil; wherein a proximal one of the tubular segments has a durometer of at least about 60 D and a distal one of the tubular segments has a durometer of no more than about 35 D. In one aspect of present disclosure, the tubular liner is formed by dip coating a removable mandrel. In another aspect of present disclosure, the tubular liner comprises PTFE.

In yet another aspect of present disclosure, the tie layer comprises polyurethane. The tie layer may have a wall thickness of no more than about 0.005 inches and may extend along at least the most distal 20 cm of the flexible body. In one aspect of present disclosure, the coil comprises a shape memory material. The coil may comprise Nitinol, and the Nitinol may comprise an Austenite state at body temperature.

In one aspect of present disclosure, the outer jacket is formed from at least five discrete tubular segments. The outer jacket may be formed from at least nine discrete tubular segments. The difference in durometer between a proximal one of the tubular segments and a distal one of the tubular segments may be at least about 20 D. The difference in durometer between a proximal one of the tubular segments and a distal one of the tubular segments may be at least about 30 D.

In another aspect of present disclosure, the enhanced flexibility neurovascular catheter, further comprises a tension support for increasing the tension resistance in the distal zone. The tension support may comprise a filament and may comprise an axially extending filament. The axially extending filament may be carried between the inner liner and the helical coil. The axially extending filament may increase the tensile strength to at least about 5 pounds.

In accordance with one aspect, there is provided an enhanced flexibility neurovascular catheter, comprising: an elongate flexible body, having a proximal end, a distal end and a side wall defining a central lumen, a distal zone of the side wall comprising: an outer jacket surrounding a helical coil, the outer jacket formed from a plurality of tubular segments positioned coaxially about the coil; wherein a proximal one of the tubular segments has a durometer of at least about 60 D and a distal one of the tubular segments has a durometer of no more than about 35 D; and an axially extending filament within the side wall, extending at least about the most distal 10 cm of the length of the catheter. The filament may extend at least about the most distal 15 cm of the length of the catheter. The filament may extend at least about the most distal 20 cm of the length of the catheter. The filament may comprise multiple fibers and may extend axially in between the coil and the inner liner.

In one aspect of present disclosure, the side wall further comprises: a tubular inner liner; a soft tie layer separated from the lumen by the inner liner; wherein the helical coil surrounds the tie layer, and adjacent windings of the coil are spaced progressively further apart in the distal direction. The tubular liner may be formed by dip coating a removable mandrel and may comprise PTFE. The tie layer may comprise polyurethane and may have a wall thickness of no more than about 0.005 inches. The tie layer may extend along at least the most distal 20 cm of the flexible body. The coil may comprise a shape memory material and may comprise Nitinol. The Nitinol may comprise an Austenite state at body temperature.

In one aspect of present disclosure, the outer jacket may be formed from at least five discrete tubular segments. In another aspect of present disclosure, the outer jacket may be formed from at least nine discrete tubular segments. The difference in durometer between a proximal one of the tubular segments and a distal one of the tubular segments may be at least about 20 D. The difference in durometer between a proximal one of the tubular segments and a distal one of the tubular segments may be at least about 30 D. In another aspect of present disclosure, the catheter can withstand at least about 3.5 pounds tension before failure. In yet another aspect, the catheter can withstand at least about 5 pounds tension before failure.

In accordance with one aspect, there is provided a method of making a high flexibility distal zone on a neurovascular catheter, comprising the steps of: dip coating a removable mandrel to form a tubular inner layer on the mandrel; coating the tubular inner layer with a soft tie layer; applying a helical coil to the outside of the tie layer; positioning a plurality of tubular segments on the helical coil; the plurality of segments having durometers that decrease in a distal direction; heating the tubular segments to form the high flexibility distal zone on the neurovascular catheter; and removing the mandrel. In one aspect of present disclosure, removing the mandrel step includes axially elongating the mandrel. In another aspect of present disclosure, the method of making a high flexibility distal zone on a neurovascular catheter comprises positioning at least seven segments on the helical coil. In yet another aspect of present disclosure, the method of making a high flexibility distal zone on a neurovascular catheter comprises positioning at least nine segments on the helical coil.

In one aspect of present disclosure, the difference in durometer between a proximal one of the tubular segments and a distal one of the tubular segments is at least about 20 D. The difference in durometer between a proximal one of the tubular segments and a distal one of the tubular segments may be at least about 30 D. The tubular inner layer may comprise PTFE. In another aspect of present disclosure, the tie layer comprises polyurethane. The tie layer may have a wall thickness of no more than about 0.005 inches. The tie layer may extend along at least the most distal 20 cm of the flexible body.

In one aspect of present disclosure, the coil comprises a shape memory material. The coil may comprise Nitinol. The Nitinol may comprise an Austenite state at body temperature. In another aspect of present disclosure, the method of making a high flexibility distal zone on a neurovascular catheter further comprises the step of positioning at least one tensile strength enhancing filament in between the coil and the tie layer prior to heat shrinking the tubular segments. The filament may extend along at least about the most distal 15 cm of the length of the catheter. The filament may extend along at least about the most distal 20 cm of the length of the catheter. The filament may comprise multiple fibers. In yet another aspect of present disclosure, the method of making a high flexibility distal zone on a neurovascular catheter further comprises the step of positioning at least one tensile strength enhancing filament over the tie layer before the applying a helical coil step.

In accordance with one aspect, there is provided a method of aspirating a vascular occlusion from a remote site, comprising the steps of: advancing an elongate tubular body through a vascular access site and into a body vessel, the tubular body comprising a proximal end, a distal end and a central lumen; positioning the distal end at least as far distally as the cavernous segment of the middle cerebral artery; applying vacuum to the lumen to draw thrombus into the lumen; and mechanically disrupting the thrombus to facilitate entry into the lumen.

In one aspect of present disclosure, the mechanically disrupting step comprises introducing vibration at the distal end of the tubular body. The vibration may be introduced by rotating an agitator within the tubular body. The method of aspirating a vascular occlusion may comprise rotating a wire within the tubular body. The method of aspirating a vascular occlusion may comprise rotating a tube within the tubular body and may further comprise the step of introducing media through the tube. The method of aspirating a vascular occlusion may comprise the step of introducing a lubricant through the tube to facilitate advancing thrombus through the lumen and may comprise the step of introducing polyethylene glycol through the tube.

In another aspect of present disclosure, the applying vacuum step comprises applying pulsatile vacuum. In yet another aspect of present disclosure, the advancing an elongate tubular body step is accomplished directly over a guidewire without any intervening tubular bodies. The method of aspirating a vascular occlusion may comprise advancing the tubular body at least as distal as the cavernous segment of the internal carotid artery. The method of aspirating a vascular occlusion may comprise advancing the tubular body at least as distal as the cerebral segment of the internal carotid artery. The method of aspirating a vascular occlusion may comprise advancing the guidewire at least as distal as the middle cerebral artery.

In one aspect of present disclosure, the method of aspirating a vascular occlusion further comprises providing sufficient back up support to the tubular body to resist prolapse of the tubular body into the aorta. The back up support may be provided to the tubular body by advancing the tubular body over a guidewire having a distal end positioned at least as distal as the cavernous segment of the internal carotid artery, and a diameter at the point the guidewire enters the brachiocephalic artery of at least about 0.030 inches. The back up support may be provided to the tubular body by advancing the tubular body over a guidewire having a distal end positioned at least as distal as the cavernous segment of the internal carotid artery, and a diameter at the point the guidewire enters the brachiocephalic artery of about 0.038 inches.

In one aspect of present disclosure, the guidewire is navigable to at least the cerebral segment of the internal carotid artery by having a distal segment having a diameter of no more than about 0.020 inches. The guidewire may be navigable to at least the cerebral segment of the internal carotid artery by having a distal segment having a diameter of about 0.016 inches. In yet another aspect of present disclosure, the method of aspirating a vascular occlusion further comprises the step of introducing an agitator into the tubular body subsequent to the positioning step. A proximal section of the agitator may extend through a constraint tube, and a distal section of the agitator may extend beyond a distal end of the constraint tube.

In accordance with one aspect, there is provided a method of aspirating a vascular occlusion from a remote site, comprising: advancing a guidewire through a vascular access point and transvascularly to a site at least as distal as the cavernous segment of the internal carotid artery; accessing a site at least as distal as the cavernous segment by advancing a combined access and aspiration catheter directly over the guidewire; removing the guidewire; and aspirating thrombus through the combined access and aspiration catheter. In one aspect of present disclosure, the method of aspirating a vascular occlusion comprises advancing the combined access and aspiration catheter at least as distal as the cerebral segment of the internal carotid artery. In another aspect of present disclosure, the method of aspirating a vascular occlusion comprises advancing the guidewire at least as distal as the middle cerebral artery.

In yet another aspect of present disclosure, the method of aspirating a vascular occlusion further comprises providing sufficient back up support to the combined access and aspiration catheter to resist prolapse of the catheter into the aorta. The back up support may be provided to the combined access and aspiration catheter by advancing the combined access and aspiration catheter over a guidewire having a distal end positioned at least as distal as the cavernous segment of the internal carotid artery, and a diameter at the point the guidewire enters the brachiocephalic artery of at least about 0.030 inches. The back up support is provided to the combined access and aspiration catheter by advancing the combined access and aspiration catheter over a guidewire having a distal end positioned at least as distal as the cavernous segment of the internal carotid artery, and a diameter at the point the guidewire enters the brachiocephalic artery of about 0.038 inches.

In one aspect of present disclosure, the guidewire is navigable to at least the cerebral segment of the internal carotid artery by having a distal segment having a diameter of no more than about 0.020 inches. The guidewire may be navigable to at least the cerebral segment of the internal carotid artery by having a distal segment having a diameter of about 0.016 inches. The diameter of the proximal section of the guidewire may be about 0.038 inches, and the diameter of the distal section may be about 0.016 inches.

In another aspect of present disclosure, a distal segment of the combined access and aspiration catheter comprises a side wall defining a central lumen, the side wall comprising: a tubular inner liner; a tie layer separated from the lumen by the inner liner; a helical coil surrounding the tie layer, adjacent windings of the coil spaced progressively further apart in the distal direction; and an outer jacket surrounding the helical coil, the outer jacket formed from a plurality of tubular segments positioned coaxially about the coil; wherein a proximal one of the tubular segments has a durometer of at least about 60 D and a distal one of the tubular segments has a durometer of no more than about 35 D. The tubular liner may be formed by dip coating a removable mandrel. The tubular liner may comprise PTFE. The tie layer may comprise polyurethane, and may have a wall thickness of no more than about 0.005 inches. The tie layer may extend along at least the most distal 20 cm of the flexible body.

In one aspect of present disclosure, the coil comprises a shape memory material. In another aspect of present disclosure, the method of aspirating a vascular occlusion further comprises introducing an agitator into the combined access and aspiration catheter. The method of aspirating a vascular occlusion may further comprise vibrating a distal portion of the agitator during the aspirating step. The method of aspirating a vascular occlusion may further comprise introducing a fluid media through the agitator during the aspirating step. The method of aspirating a vascular occlusion may further comprise introducing polyethylene glycol through the agitator during the aspirating step.

In accordance with one aspect, there is provided a neurovascular catheter, comprising: an elongate flexible tubular body, having a proximal end, a distal end and a side wall defining a central lumen, a distal zone of the tubular body comprising: a tubular inner liner; a tie layer separated from the lumen by the inner liner; a helical coil surrounding the tie layer, adjacent windings of the coil spaced progressively further apart in the distal direction; an outer jacket surrounding the helical coil, and an opening at the distal end which is enlargeable from a first inside diameter for transluminal navigation to a second, larger inside diameter to facilitate aspiration of thrombus into the lumen. In one aspect of present disclosure, the distal opening is enlargeable in response to exposure to blood. In another aspect of present disclosure, the distal opening is enlargeable in response to exposure to body temperature. In yet another aspect of present disclosure, the distal opening is enlargeable in response to removal of a constraint. The constraint may comprise a polymer having a structural integrity that decreases in the intravascular environment.

In one aspect of present disclosure, the catheter body adjacent the distal opening comprises a radially outwardly biased embedded support. The catheter body adjacent the distal opening may comprise an embedded Nitinol frame. The support may comprise a wire mesh. The support may comprise a stent. In another aspect of present disclosure, the catheter body adjacent the distal opening comprises a hydrophilic blend. In yet another aspect of present disclosure, the tubular liner is formed by dip coating a removable mandrel. The tubular liner may comprise PTFE.

In one aspect of present disclosure, the tie layer comprises polyurethane. The tie layer may have a wall thickness of no more than about 0.005 inches. The tie layer may extend along at least the most distal 20 cm of the flexible body. In another aspect of present disclosure, the coil comprises a shape memory material. The coil may comprise Nitinol. The Nitinol may comprise an Austenite state at body temperature. In one aspect of present disclosure, the outer jacket is formed from at least five discrete tubular segments. The outer jacket may be formed from at least nine discrete tubular segments. The difference in durometer between a proximal one of the tubular segments and a distal one of the tubular segments may be at least about 20 D. The difference in durometer between a proximal one of the tubular segments and a distal one of the tubular segments may be at least about 30 D.

In accordance with one aspect, there is provided a neurovascular catheter extension segment, comprising: an elongate flexible control wire, having a proximal end and a distal end; a tubular extension segment having a side wall defining a central lumen carried by the distal end of the control wire, the side wall comprising: a tubular inner liner; a tie layer separated from the lumen by the inner liner; a helical coil surrounding the tie layer; and an outer jacket surrounding the helical coil. In one aspect of present disclosure, the outer jacket is formed from a plurality of tubular segments positioned coaxially about the coil. A proximal one of the tubular segments may have a durometer of at least about 60 D, and a distal one of the tubular segments may have a durometer of no more than about 35 D.

In another aspect of present disclosure, the tubular liner is formed by dip coating a removable mandrel. The tubular liner may comprise PTFE. In yet another aspect of present disclosure, the tie layer comprises polyurethane. The tie layer may have a wall thickness of no more than about 0.005 inches. The tie layer may extend along at least the most distal 20 cm of the tubular extension segment. In one aspect of present disclosure, the coil comprises a shape memory material. The coil may comprise Nitinol. The Nitinol may comprise an Austenite state at body temperature.

In one aspect of present disclosure, the outer jacket is formed from at least five discrete tubular segments. The outer jacket may be formed from at least nine discrete tubular segments. The difference in durometer between a proximal one of the tubular segments and a distal one of the tubular segments may be at least about 20 D. The difference in durometer between a proximal one of the tubular segments and a distal one of the tubular segments may be at least about 30 D. In another aspect of present disclosure, the control wire comprises a central lumen. The control wire central lumen may be in communication with the central lumen of the tubular extension segment. In yet another aspect of present disclosure, the inside diameter of the neurovascular catheter extension segment is at least 2× the inside diameter of the control wire central lumen. The inside diameter of the neurovascular catheter extension segment may be at least 3× the inside diameter of the control wire central lumen.

In accordance with another aspect, there is provided a neurovascular catheter extension segment system, comprising the neurovascular catheter extension segment described above and an agitator configured to extend through the control wire central lumen and into the central lumen of the tubular extension segment.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

What is claimed is:

1. A telescoping catheter comprising:
   an elongate, flexible tubular body comprising a proximal section having at least one lumen and a distal section axially movably positioned within the at least one lumen, the distal section being advanceable from a first, proximally retracted position within the proximal section to a second, extended position extending distally beyond the proximal section; and
   an active tip on a distal end of the distal section, the active tip comprising a distal opening that is movable between a smaller configuration and a larger configuration,
   wherein the active tip is naturally biased toward the larger configuration,
   wherein the active tip is configured to be retained in the smaller configuration by application of a negative pressure within the distal section,
   wherein application of a pulsatile vacuum comprising two or more pressure pulses oscillating between the negative pressure and at least one of a second negative pressure, a positive pressure, or a neutral pressure causes the distal opening of the active tip to reciprocate between the smaller configuration and the larger configuration to perform repeated biting motions in response to application of the pulsatile vacuum, and
   wherein the distal opening of the active tip is configured to reciprocate between the smaller configuration and the larger configuration at least when the distal opening is empty.

2. A telescoping catheter as in claim 1, further comprising a pull wire extending through the proximal section for advancing the distal section between the first, proximally retracted position and the second, extended position.

3. A telescoping catheter as in claim 1, wherein the distal section is distally advanceable to extend beyond the proximal section for a distance of at least about 10 cm.

4. A telescoping catheter as in claim 1, wherein the distal section is distally advanceable to extend beyond the proximal section for a distance of at least about 25 cm.

5. A telescoping catheter as in claim 1, wherein the distal opening is movable in response to movement of a control wire.

6. A telescoping catheter as in claim 1, wherein the active tip is configured to transition between the smaller configuration and the larger configuration by lateral movement of a side wall on the distal section.

7. A telescoping catheter as in claim 1, wherein the distal opening comprises at least one movable jaw.

8. A telescoping catheter as in claim 1, wherein the distal end of the distal section comprises a duck bill valve configuration.

9. A telescoping catheter as in claim 1, further comprising a controller for applying the pulsatile vacuum to the at least one lumen.

10. A telescoping catheter as in claim 9, wherein the pulsatile vacuum oscillates between the negative pressure and the neutral pressure.

11. A telescoping catheter as in claim 9, wherein the pulsatile vacuum oscillates between the negative pressure and the second negative pressure, and wherein the second negative pressure is less than the negative pressure.

12. A telescoping catheter as in claim 1, wherein the active tip comprises a funnel shape in the larger configuration and a substantially cylindrical shape in the smaller configuration.

13. A telescoping catheter as in claim 1, wherein a diameter of the distal opening is at least about 10% larger in the larger configuration than in the smaller configuration.

14. A telescoping catheter as in claim 1, wherein a diameter of the distal opening is at least about 25% larger in the larger configuration than in the smaller configuration.

15. A telescoping catheter as in claim 1, wherein a diameter of the distal opening is at least about 45% larger in the larger configuration than in the smaller configuration.

* * * * *